(12) United States Patent
Park et al.

(10) Patent No.: US 8,828,992 B2
(45) Date of Patent: Sep. 9, 2014

(54) SUBSTITUTED AZOLE DERIVATIVES, PHARMACEUTICAL COMPOSITION CONTAINING THE DERIVATIVES, AND METHOD FOR TREATING PARKINSON'S DISEASE USING THE SAME

(75) Inventors: Cheol-Hyoung Park, Daejeon (KR); Hye-Kyung Min, Daejeon (KR); Mi-Jung Lim, Daejeon (KR); Ji-Won Lee, Daejeon (KR); Jin-Yong Chung, Daejeon (KR); Choon-Ho Ryu, Daejeon (KR); Yeo-Jin Yoon, Daejeon (KR); Mi-Kyung Ji, Seoul (KR); Joo-Young Park, Daejeon (KR)

(73) Assignee: SK Biopharmaceuticals Co., Ltd., Seoul (KR)

(*) Notice: Subject to any disclaimer, the term of this patent is extended or adjusted under 35 U.S.C. 154(b) by 0 days.

(21) Appl. No.: 13/202,449

(22) PCT Filed: Feb. 25, 2010

(86) PCT No.: PCT/KR2010/001186
§ 371 (c)(1),
(2), (4) Date: Aug. 19, 2011

(87) PCT Pub. No.: WO2010/098600
PCT Pub. Date: Sep. 2, 2010

(65) Prior Publication Data
US 2011/0301150 A1    Dec. 8, 2011

(30) Foreign Application Priority Data

Feb. 25, 2009  (KR) .................. 10-2009-0015856
Feb. 24, 2010  (KR) .................. 10-2010-0016686

(51) Int. Cl.
| A61K 31/551 | (2006.01) |
| A61K 31/5377 | (2006.01) |
| A61K 31/4439 | (2006.01) |
| A61K 31/42 | (2006.01) |
| C07D 413/06 | (2006.01) |
| C07D 413/12 | (2006.01) |
| C07D 261/08 | (2006.01) |
| C07D 263/32 | (2006.01) |
| C07D 277/02 | (2006.01) |
| A61K 45/06 | (2006.01) |
| C07D 249/10 | (2006.01) |
| A61K 31/554 | (2006.01) |
| A61K 31/16 | (2006.01) |
| A61K 31/198 | (2006.01) |

(52) U.S. Cl.
CPC ............. *C07D 277/02* (2013.01); *A61K 45/06* (2013.01); *C07D 249/10* (2013.01); *A61K 31/554* (2013.01); *A61K 31/16* (2013.01); *A61K 31/198* (2013.01)

USPC .......... 514/218; 514/236.8; 514/340; 514/378; 514/324; 540/575; 544/137; 546/272.1; 548/247; 548/235

(58) Field of Classification Search
USPC .......... 514/218, 378, 364, 372, 361, 367, 340, 514/314, 326, 236.8, 254.04; 548/247, 131, 548/214, 128, 180; 546/272.1, 174, 209; 540/575; 544/137, 367
See application file for complete search history.

(56) References Cited

U.S. PATENT DOCUMENTS

| 3,245,989 A | 4/1966 | Palazzo ...................... 260/247.2 |
| 6,818,774 B2 | 11/2004 | Cesura et al. |
| 7,173,023 B2 | 2/2007 | Jolidon et al. |
| 7,291,641 B2 | 11/2007 | Chabrier De Lassauniere |
| 8,288,560 B2 | 10/2012 | Chabrier De Lassauniere et al. ... 548/205 |
| 2003/0225122 A1 | 12/2003 | Cesura et al. .................. 514/309 |
| 2005/0030887 A1 | 2/2005 | Jacobsen et al. .............. 370/208 |
| 2005/0171358 A1 | 8/2005 | Shimozono et al. .......... 548/247 |
| 2007/0066630 A1 | 3/2007 | Palani et al. ................ 514/260.1 |

FOREIGN PATENT DOCUMENTS

| CN | 1369492 | 9/2002 | ................ A61P 9/12 |
| CN | 1391474 | 1/2003 | ........... A61K 31/426 |
| CN | 1649844 | 8/2005 | ........... C07D 217/24 |
| DE | 248589 | 1/1912 | |
| DE | 263 987 | 1/1989 | ........... C67D 271/06 |
| EP | 0 504 574 | 9/1992 | ........... C07D 271/06 |
| EP | 1 935 892 | 6/2008 | ........... C07D 407/04 |
| FR | 1386543 | 12/1963 | |
| GB | 924608 | 4/1963 | |
| GB | 965925 | 8/1964 | |
| GB | 969813 | 9/1964 | |
| GB | 1065889 | 4/1967 | ............. C07D 85/22 |
| JP | S42-9145 | 5/1967 | .................... 16/E342 |

(Continued)

OTHER PUBLICATIONS

Kano et al., Isoxazoles. XVIII. Synthesis and Pharmacological Properties of 5-Aminoalkyl- and 3-Aminoalkylisoxazoles and Related Derivatives, 1967, Journal of Medicinal Chemistry, 10(3), 411-418.*

(Continued)

*Primary Examiner* — Nobel Jarrell
(74) *Attorney, Agent, or Firm* — Harness, Dickey & Pierce, P.L.C.

(57) ABSTRACT

Provided are a substituted azole derivative and pharmaceutically acceptable salts thereof, a pharmaceutical composition including an effective amount of the derivative, and a method for treating Parkinson's disease in a mammal including administering an effective amount of the compound to the mammal. The azole derivative of the following Formula (I) and pharmaceutically useful salts thereof have an efficacy against Parkinson's disease from inhibitory effects of the activity of MAO-B.

27 Claims, No Drawings

(56) References Cited

FOREIGN PATENT DOCUMENTS

| | | | |
|---|---|---|---|
| JP | S42-9146 | 5/1967 | ............ 16/E342 |
| JP | 04-295470 | 10/1992 | ........ C07D 271/06 |
| JP | 2007-518720 | 7/2007 | ........ C07D 471/04 |
| KR | 10-0681585 | 2/2007 | |
| KR | 10-0731698 | 6/2007 | |
| KR | 10-0856141 | 9/2008 | |
| WO | WO 98/15541 | 4/1998 | ........ C07D 261/04 |
| WO | WO 03/074501 | 9/2003 | ........ C07D 261/08 |
| WO | 2004026826 | 4/2004 | |
| WO | 2006013049 | 2/2006 | |
| WO | WO 2006/033703 | 3/2006 | ........ C07D 473/00 |
| WO | WO 2007/061923 | 5/2007 | |
| WO | WO 2008/076356 | 6/2008 | ........ A01N 43/82 |
| WO | WO 2009/010479 | 1/2009 | ........ C07D 413/06 |
| WO | WO 2009/011787 | 1/2009 | ........ C07D 487/04 |

OTHER PUBLICATIONS

The International Search Report and Written Opinion issued on Nov. 11, 2010, in the related PCT Application No. PCT/KR2010/001186.

Bezard et al., "Adaptive changes in the nigrostriatal pathway in response to increased 1-methyl-4-phenyl-1,2,3,6-tetrahydropyridine-induced neurodegeneration in the mouse," European Journal of Neuroscience vol. 12, Issue 8, pp. 2892-2900, Aug. 2000.

Breidert et al., "Protective action of the peroxisome proliferator-activated receptor-gamma agonist pioglitazone in a mouse model of Parkinson's disease,"J Neurochem. Aug. 2002;82(3):615-24.

Khaldy et al., "Synergistic effects of melatonin and deprenyl against MPTP-induced mitochondrial damage and DA depletion," Neurobiology of Aging 24 (2003) 491-500.

Muramatsu et al., "Therapeutic Effect of Neuronal Nitric Oxide Synthase Inhibitor (7-Nitroindazole) against MPTP Neurotoxicity in Mice," Metabolic Brain Disease, vol. 17, No. 3, Sep. 2002.

Putterman et al., "Evaluation of levodopa dose and magnitude of dopamine depletion as risk factors for levodopa-induced dyskinesia in a rat model of Parkinson's disease," The Journal of pharmacology and experimental therapeutics Oct. 2007; 323; (1):277-84.

Yang et al., "Minocycline Enhances MPTP Toxicity to Dopaminergic Neurons," Journal of Neuroscience Research 74:278-285 (2003).

Yeung et al., "A base-catalyzed, direct synthesis of 3,5-disubstituted 1,2,4-triazoles from nitriles and hydrazides," Tetrahedron Letters, vol. 46, Issue 19, May 9, 2005, pp. 3429-3432.

Office Action issued in Chinese Patent Application No. 201080009749.2 dated Sep. 22, 2013.

Antunes, et al. (1998) "New phthalimide derivatives with potent analgesic activity: II." *Bioorganic & Medicinal Chemistry Letters* 8:3071-3076.

Dannhardt, et al. (1993) "Hypertensive effects and structure-activity relationships of 5-omega-aminoalkyl isoxazoles." Arzneim. Forsch., Drug Res. 43(4) 1 Kamiaru:441-444.

Katritzky, et al. (2000) "Efficient synthesis of 3,5-functionalized isoxazoles and isoxazolines via 1,3-dipolar cycloaddition reactions of 1-propargyl- and 1-allylbenzotriazoles." *J. Heterocyclic. Chem.* 37:1505-1510.

Skacani, et al. (1991) "The preparation and fungicidal activity of a series of 1-[(3-arylisoxazolin- or isoxazol-5-yl)methyl]-1H-1,2,4-triazoles." *Chem. Papers* 45(6):807-815.

Supplementary European Search Report (ESR) in EP Application No. 10746439.8 dated Oct. 25, 2012.

Communication of amended entries concerning the representative (R. 143(1)(h) EPC) in EP Application No. 10746439.8 dated Jun. 11, 2013.

Office Action, dated in Jan. 24, 2014 issued in Russian Patent lApplication No. 2011134423, with English language translation.

Braga, et al. (2004) "One-pot synthesis of chiral n-protected α-amino acid-derived 1,2,4-oxadiazoles." *Synthesis* 10:1589-1594.

Gfesser, et al. (2004) "Structure-activity relationships of non-imidazole $H_3$ receptor ligands. Part 3: 5-substituted 3-phenyl-1,2,4-oxadiazoles as potent antagonists." *Bioorg. Med. Chem. Lett.* 14(3):673-676.

Japanese Office Action, mailed Apr. 2, 2014 issued in Japanese Patent Application No. 2011-551984, with English language translation.

Palazzo, et al. (1962) "Ricerche nel campo dell'1,2,4-oxadiazolo." *Boll. Chim. Farm.* 101:251-258.

Patra, et al. (2003) "Isoxazole-based derivatives from Baylis-Hillman Chemistry: assessment of preliminary hypolipidemic activity." *Bioorg. Med. Chem.* 11(10):2269-2276.

Pätzel, et al. (1991) "5-(ω-aminoalkyl)-1,2,4-oxadiazoles by ring-transformations of 3-methylthio-2-aza-3-propeniminium salts." *Arch. Pharm (Weinheim)* 324(12):963-965.

Scicinski, et al. (2001) "Solid-phase development of a 1-hydroxybenzotriazole linker for heterocycle synthesis using analytical constructs." *J. Comb. Chem.* 3(4):387-396.

Virmani, et al. (1979) "Chemistry of lactam acetals: part II-synthesis of pyrazoles & isoxazoles." *Indian Journal of Chemistry* 17B(5):472-477.

\* cited by examiner

SUBSTITUTED AZOLE DERIVATIVES, PHARMACEUTICAL COMPOSITION CONTAINING THE DERIVATIVES, AND METHOD FOR TREATING PARKINSON'S DISEASE USING THE SAME

TECHNICAL FIELD

The present disclosure relates to a substituted azole derivative represented by the Formula (I) showing efficacy against Parkinson's disease, a pharmaceutical composition containing an effective amount of the derivative, and a method for treating Parkinson's disease by administering the same to mammals.

BACKGROUND ART

Parkinson's disease is a difficult-to-treat, progressive disorder which is the second most common neurodegenerative disease, and is socially and economically problematic because its incidence rate continues to rise as the population of seniors increases. Currently, about 4 million people worldwide are known to have the disease, and it is understood that the number of new cases per year is growing by about 50 thousand in U.S. alone. The incidence rate of one in 1,000 is more prevalent-in older age groups. The disorder is known to be mostly associated with aging, environmental factors such as neurotoxin accumulation from agricultural chemicals, etc., active oxygen, genetic factors (about 5% to about 10%), etc are known to have effects on the incidence. However, the exact cause of incidence is unknown. As for genetic factors, gene mutations such as α-synuclein, Parkin, PINK-1, UCH-L1, DJ-1, etc. are known to be associated with incidence.

Anatomical studies show that Parkinson's disease is associated with a broad range of degeneration of dopaminergic substantia nigra neurons located in the basal ganglia of the brain. When about 60% to about 80% of the amount of dopamine produced by substantia nigra neurons is damaged, it can no longer facilitate the movement of the extrapyramidal tract system, thereby resulting in Parkinson's symptoms.

Because the exact cause of Parkinson's disease has not been determined, treatment methods for ameliorating symptoms are usually used, rather than fundamental cures. Therapeutic agents currently used or under development are as follows. Drugs which are predominantly developed and used include dopamine precursors such as Levodopa as a dopamine supplement and dopamine receptor agonists such as Fenofibrate. In addition, COMT inhibitors which maintain the dopamine concentration in the brain by inhibiting dopamine metabolism and MAO-B (monoamine oxidase B) inhibitors are being used. As a neurotransmitter enhancing drug besides dopamine, antimuscarinics and NMDA antagonists are developed and used, and continuous efforts are being made to use or develop neuronal protective agents, antioxidants, inhibitors of neuronal apoptosis, and agonists for brain function as therapeutic agents. Surgical therapies such as deep brain stimulation are applied to terminal stage patients who can no longer benefit from drug therapies.

Selegiline (Deprenyl) as a MAO-B inhibitor has been used as a drug for treating Parkinson's disease and is considered a gold standard. However, its use has many limitations due to hepatotoxicity and production of metamphetamine as a metabolite. Azilect (Rasagiline) was first commercially introduced in Europe in 2005 and approved by the US FDA in 2006 as a new MAO-B inhibitor, and emerged as a new therapeutic agent for Parkinson's disease that overcomes the disadvantages of Selegiline. If clinical tests can verify that Azilect has neuronal protective effects that other current therapeutic agents lack, the value of the drug as a new therapeutic agent will be greatly enhanced.

However, because both Selegiline and Rasagiline are irreversible MAO-B inhibitors, they may inhibit the activity of MAO-B until new MAO-B is produced in vivo, thereby increasing the possibility of unpredictable side effects. As an alternative to make up for these shortcomings, a new drug to show potent enzyme inhibitory activity in a reversible manner is expected to be superior to conventional irreversible inhibitors in terms of safety and efficacy. While a reversible MAO-B inhibitor called Safinamide has been developed and is under clinical testing (Phase III), an exceptional reversible MAO-B inhibitor has not been developed yet.

DISCLOSURE OF INVENTION

Technical Problem

Thus, an aspect of the present invention provides compositions having efficacy against Parkinson's disease and pharmaceutically acceptable salts thereof.

An aspect of the present invention also provides a pharmaceutical composition for treatment of Parkinson's disease.

Another aspect of the present invention further provides a method for treating Parkinson's disease in a mammal by administering an effective amount of the compound to the mammal.

Solution to Problem

According to an aspect of the present invention, there are provided substituted azole derivatives represented by Formula (I) having efficacy against Parkinson's disease and pharmaceutically acceptable salts thereof:

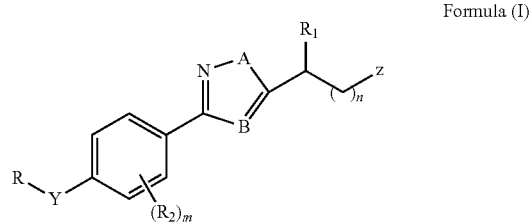

Formula (I)

According to another aspect of the present invention, there are provided pharmaceutical compositions for treatment of Parkinson's disease, including an effective amount of the substituted azole derivative.

According to still another aspect of the present invention, there are provided methods for treating Parkinson's disease in a mammal by administering an effective amount of the substituted azole derivative to the mammal.

According to still another aspect of the present invention provides a use of an effective amount of a compound of Formula (I) or a pharmaceutically acceptable salt thereof for treatment of Parkinson's disease, and a use of an effective amount of a compound of Formula (I) or a pharmaceutically acceptable salt thereof for preparation of a medicament suitable for treating Parkinson's disease.

The details of one or more embodiments are set forth in the accompanying drawings and the description below. Other features will be apparent from the description and drawings, and from the claims.

Advantageous Effects of Invention

The compound of Formula (I) may be used as a pharmaceutical composition for treatment of Parkinson's disease by inhibiting the activity of MAO-B.

BEST MODE FOR CARRYING OUT THE INVENTION

Reference will now be made in detail to the embodiments of the present disclosure, examples of which are illustrated in the accompanying drawings.

One embodiment of the present disclosure relates to substituted azole derivatives represented by Formula (I) and pharmaceutically acceptable salts thereof:

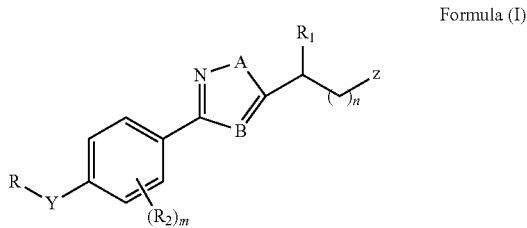

Formula (I)

wherein, R is selected from the group consisting of substituted or unsubstituted $C_4$-$C_{15}$ arylalkyl and $C_4$-$C_{15}$ heteroarylalkyl; and substituted or unsubstituted linear, branched or cyclic $C_1$-$C_{10}$ alkyl;

Y is selected from the group consisting of O and —N—$R_1$;

$R_1$ is at least one selected from the group consisting of H and linear or branched $C_1$-$C_3$ alkyl;

$R_2$ is selected from the group consisting of H and halogen;

A is selected from the group consisting of N, O, and S;

B is selected from the group consisting of C and N;

Z is selected from the group consisting of substituted or unsubstituted heterocyclic ring; carbamate; —OC(=O)NR$_3$R$_4$; NH$_2$; NR$_5$R$_6$; NC(=NH)NH$_2$; and —NC(=O)NH$_2$;

each of and $R_4$ is independently selected from the group consisting of H; $C_1$-$C_5$ alkyl unsubstituted or substituted by at least one selected from the group consisting of NH$_2$, and NR$_7$R$_8$; heterocyclic ring unsubstituted or substituted by $C_1$-$C_3$ alkyl; or $R_3$ and $R_4$ together may form a 5- or 7-membered heterocyclic ring unsubstituted or substituted by $C_1$-$C_3$ alkyl;

each of $R_5$ and $R_6$ is independently selected from the group consisting of H; $C_2$-$C_3$ alkene; $C_2$-$C_3$ alkyne; and linear or branched $C_1$-$C_7$ alkyl unsubstituted or substituted by at least one selected from the group consisting of —OH, —C(O)NH$_2$, $C_1$-$C_3$ alkoxy, and carbamate, or $R_5$ and $R_6$ together may form a substituted or unsubstituted aliphatic cyclic amine or aromatic cyclic amine;

each of $R_7$ and $R_8$ is at least one independently selected from the group consisting of H and linear or branched $C_1$-$C_3$ alkyl;

m is an integer of 0 to 4; and n is an integer of 0 to 5.

More specifically, a preferred compound is an azole derivative and a pharmaceutically acceptable salt thereof: wherein, R is selected from the group consisting of $C_4$-$C_{15}$ arylalkyl unsubstituted or substituted by at least one selected from the group consisting of halogen, trifluoromethyl, trifluoroalkoxy, —NO$_2$, C(=O)OCH$_3$, linear or branched $C_1$-$C_6$ alkyl, $C_1$-$C_6$ alkoxy, phenyl, phenyloxy, benzyloxy, —C(=O)H, —OH, and —C=N—OH; $C_4$-$C_{15}$heteroarylalkyl unsubstituted or substituted by at least one selected from the group consisting of halogen, C(=O)OCH$_3$, linear or branched $C_1$-$C_6$ alkyl, $C_1$-$C_6$ alkoxy, phenyl, phenyloxy, benzyloxy, —C(=O)H; linear, branched, or cyclic $C_1$-$C_{10}$ alkyl unsubstituted or substituted by at least one selected from the group consisting of unsubstituted or substituted $C_4$-$C_{15}$heteroarylalkyl, $C_1$-$C_3$alkyloxy, $C_1$-$C_3$ alkylthio, carbamate, (—OC(=O)NH$_2$), tert-butyl-OC(=O)NH—, —NH$_3^+$, —NH$_2$, —OH, —C(=O)OCH$_2$CH$_3$, —NHC(=O)NH$_2$, trifluoromethylsufanyl, trifluoromethyl, and —CN; if R is $C_4$-$C_{15}$ heteroarylalkyl, wherein the heteroaryl group is selected from the group consisting of imidazole, chlorothiophen, naphthalene, benzothiazole, pyridine, quinoline, benzotriazole, isoxazole, furan, N-oxopyridine, N-methylpyridine and benzo[1,3]dioxole; and if R is $C_4$-$C_{15}$arylalkyl, wherein the aryl group is selected from the group consisting of phenyl, phenyloxy, benzyloxy and naphthalene.

Z is selected from the group consisting of imidazole, piperidine, pyrrolidine, triazole, and tetrazole unsubstituted or substituted by at least one substituent selected from the group consisting of OH, carbamate, linear or branched $C_1$-$C_4$ alkyl, halogen, —NO$_2$, —NH$_2$, —CF$_3$, —CN, and phenyl; carbamate; —OC(=O)NR$_3$R$_4$; NH$_2$; NR$_5$R$_6$; NC(=NH)NH$_2$, and —NC(=O)NH$_2$;

each of $R_3$ and $R_4$ is independently selected from the group consisting of H; $C_1$-$C_5$ alkyl unsubstituted or substituted by at least one selected from the group consisting of NH$_2$, and NR$_7$R$_8$; and piperidine, piperazine, and diazepane unsubstituted or substituted by $C_1$-$C_3$ alkyl, or $R_3$ and $R_4$ together may form piperidine, piperazine, imidazole, pyrrolidine, triazole, tetrazole, diazepane or morpholine unsubstituted or substituted by $C_1$-$C_3$ alkyl;

each of $R_5$ and $R_6$ is independently selected from the group consisting of H; $C_2$-$C_3$ alkene; $C_2$-$C_3$ alkyne; and linear or branched $C_1$-$C_4$ alkyl unsubstituted or substituted by at least one selected from the group consisting of —OH, —C(O)NH$_2$, $C_1$-$C_3$ alkoxy, and carbamate, or $R_5$ and $R_6$ together may form piperidine, piperazine, imidazole, tetrazole, triazole, pyrrolidine or morpholine substistuted or unsubstituted by at least one selected from the group consisting of OH, carbamate, $C_1$-$C_3$ alkyl, halogen, phenyl, and —NO$_2$;

each of $R_7$ and $R_8$ is at least one independently selected from the group consisting of H and linear or branched $C_1$-$C_3$ alkyl;

B is C or N;

m and n are independently 0 or 1; and

Y, $R_1$, A, and $R_2$ are as defined above.

Compounds well known to those skilled in the art, which may be easily prepared there from azole derivatives, may be used to prepare an azole derivative of Formula (1). Thus, it is to be understood that the following description related to a preparation method of the azole derivative is only illustrative of the present invention and is not meant to limit the scope of the present invention as modifications may be selectively made on the sequence of the unit operation if necessary.

Scheme 1: Synthesis of azole

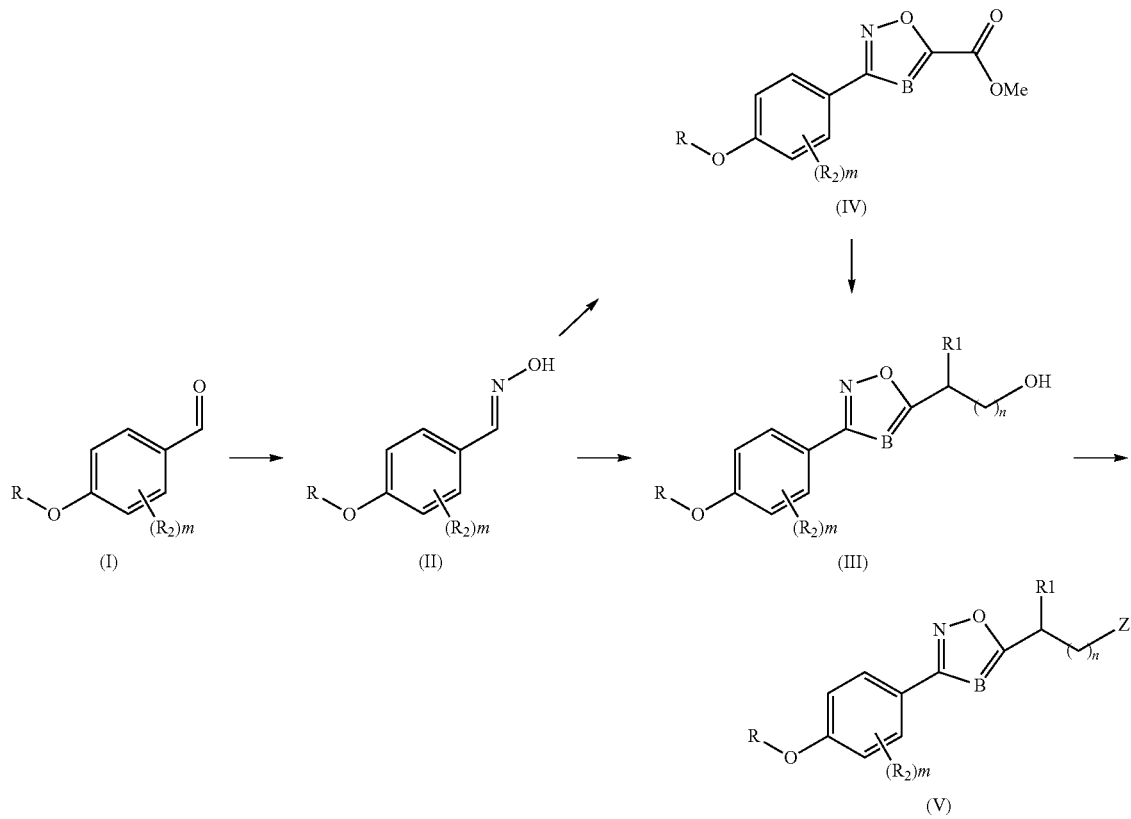

R is preferably a benzyl group, and $R_1$, $R_2$, Z, B, m, and n are as mentioned above. A general synthetic method is as follows: An aldehyde (I) as a starting material may be used to obtain an oxime (II). Subsequently, a [3+2] cycloaddition of the obtained oxime compound with alkyne or nitrile may be performed under the NaOCl conditions to obtain an azole compound (III or IV), followed by introduction of a desired functional group to obtain a final compound (V).

Scheme 2: Synthesis of thiazole

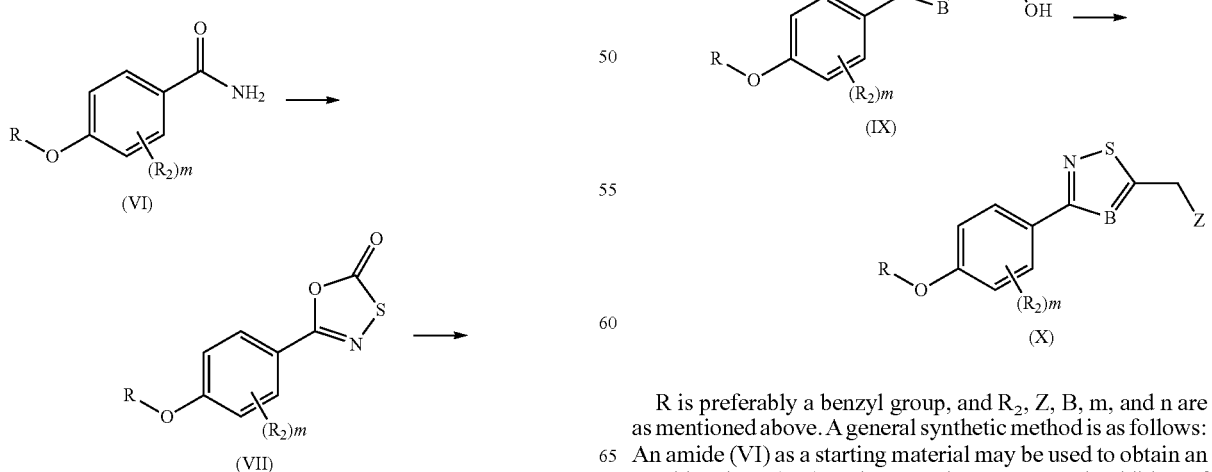

R is preferably a benzyl group, and $R_2$, Z, B, m, and n are as mentioned above. A general synthetic method is as follows: An amide (VI) as a starting material may be used to obtain an oxathiazolone (VII). Subsequently, a [3+2] cycloaddition of the obtained oxathiazolone compound with alkyne or nitrile may be performed under the NaOCl conditions to obtain a thiazole compound (VIII), followed by reduction of this compound and introduction of a functional group to obtain a final compound (X).

Scheme 3

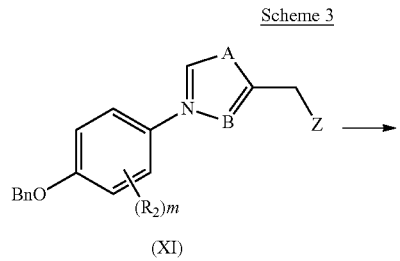

(XI)

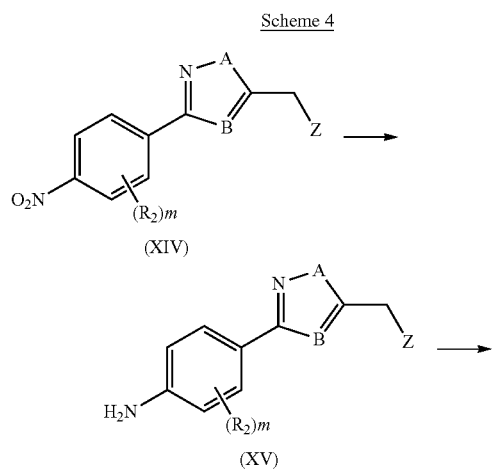

R, R$_2$, Z, A, m, and B are as mentioned above. A general synthetic method is as follows: A debenzylation of a compound (XI) as a starting material may be performed to obtain a hydroxyphenyl derivative (XII), followed by introduction of a desired functional group to obtain a final compound (XIII).

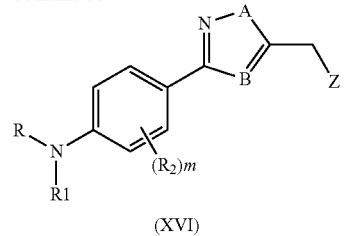

(XVI)

R, R$_1$, R$_2$, Z, A, m, and B are as mentioned above. A general synthetic method is as follows: A reduction of a nitrophenyl derivative (XIV) as a starting material may be performed to synthesize an aminophenyl derivative (XV), followed by reductive amination with a desired aldehyde to obtain a final compound (XVI).

In addition, the azole derivative includes a compound represented by Formula (I) as well as pharmaceutically acceptable acids or base addition salts thereof and stereochemically isomeric forms thereof. The salts include anything as long as they maintain the activity of a parent compound in a subject to be administered and do not cause any adverse effect.

Examples of such salts include, but are not specifically limited to, inorganic and organic salts, and salts of the following acids are preferably selected. More specifically, they include acetic, nitric, aspartic, sulfonic, sulfuric, maleic, glutamic, formic, succinic, phosphoric, phthalic, tannic, tartaric, hydrobromic, propionic, benzenesulfonic, benzoic, stearic, esyl, lactic, bicarbonic, bisulfuric, bitartaric, oxalic, butyric, calcium edetate, camsylic, carbonic, chlorobenzoic, citric, edetic, toluenesulfonic, edisylic, esylic, fumaric, gluceptic, pamoic, gluconic, glycollylarsanilic, methylnitric, polygalactouronic, hexylresorcinoic, malonic, hydrabamic, hydrochloric, hydroiodic, hydroxynaphthoic, isethionic, lactobionic, mandelic, estolic, methylsulfuric, mucic, napsylic, muconic, p-nitromethanesulfonic, hexamic, pantothenic, monohyrogen phosphoric, dihyrogen phosphoric, salicylic, sulfamic, sulfanilic, methanesulfonic, teoclic acids, etc.

In addition, the base salt forms include, for example, ammonium salts, alkal and alkaline earth salts, e.g. lithium, sodium potassium, magnesium, and calcium salts, salts with organic base, e.g. benzathine, N-methyl-D-glucamine, hydrabamine salts, and salts with amino acids such as, for example, arginine, lysine, etc.

Conversely, the salt forms may be converted by treatment with an appropriate base or acid into the free base or acid form.

The term "addition salt" as used herein includes the solvates which the compounds of formula (I) as well as the salts thereof are able to form. Such solvates are, for example, hydrates, alcoholates, etc.

Furthermore, the term "stereochemically isomeric forms" of the compounds of Formula (I) as used herein defines all the possible different compounds which the compounds of Formula (I) may possess. Unless otherwise mentioned or indicated, the chemical designation of compounds denotes the mixture of all possible stereochemically isomeric forms, the mixtures containing all diastereomers and enantiomers of the basic molecular structure.

In particular, stereogenic centers may have an R- or S-configuration; substituents on bivalent cyclic (partially) saturated radicals may have either a cis- or trans-configuration. Compounds including double bonds can have an E or Z-stereochemistry at the double bond. Stereochemically isomeric forms of the compounds represented by Formula (I) are obviously intended to be embraced within the scope of this invention As defined in Formula (I), examples of preferred azole derivatives are as follows.

Examples of the compound, in which Y is O; Z is carbamate; and R, $R_1$-$R_8$, A, B, m, and n are as described above, include carbamic acid 3-(4-benzyloxy-phenyl)-isoxazol-5-ylmethyl ester, carbamic acid 3-(4-benzyloxy-phenyl)-[1,2,4]oxadiazol-5-ylmethyl ester, carbamic acid 3-(4-benzyloxy-phenyl)-isothiazol-5-ylmethyl ester, carbamic acid 3-(4-benzyloxy-phenyl)-[1,2,4]thiadiazol-5-ylmethyl ester, carbamic acid 3-(4-benzyloxy-2-chloro-phenyl)-isoxazol-5-ylmethyl ester, carbamic acid 3-(4-benzyloxy-3-chloro-phenyl)-isoxazol-5-ylmethyl ester, carbamic acid 3-(4-benzyloxy-3-bromo-phenyl)-isoxazol-5-ylmethyl ester, carbamic acid 3-(4-benzyloxy-3-fluoro-phenyl)-isoxazol-5-ylmethyl ester, carbamic acid 3-(4-benzyloxy-3,5-dimethyl-phenyl)-isoxazol-5-ylmethyl ester, carbamic acid 3-[4-(1-phenyl-ethoxy)-phenyl]-isoxazol-5-ylmethyl ester, carbamic acid 3-[4-(2-fluoro-benzyloxy)-phenyl]-isoxazol-5-ylmethyl ester, carbamic acid 3-[4-(3-fluoro-benzyloxy)-phenyl]-isoxazol-5-ylmethyl ester, carbamic acid 3-[4-(4-fluoro-benzyloxy)-phenyl]-isoxazol-5-ylmethyl ester, carbamic acid 3-[4-(2,6-difluoro-benzyloxy)-phenyl]-isoxazol-5-ylmethyl ester, carbamic acid 3-[4-(2,3-difluoro-benzyloxy)-phenyl]-isoxazol-5-ylmethyl ester, carbamic acid 3-[4-(3,5-difluoro-benzyloxy)-phenyl]-isoxazol-5-ylmethyl ester, carbamic acid 3-[4-(3,4-difluoro-benzyloxy)-phenyl]-isoxazol-5-ylmethyl ester, carbamic acid 3-[4-(2,4,6-trifluoro-benzyloxy)-phenyl]-isoxazol-5-ylmethyl ester, carbamic acid 3-[4-(3-trifluoromethyl-benzyloxy)-phenyl]-isoxazol-5-ylmethyl ester, carbamic acid 3-[4-(3-chloro-benzyloxy)-phenyl]-isoxazol-5-ylmethyl ester, carbamic acid 3-[4-(2-chloro-benzyloxy)-phenyl]-isoxazol-5-ylmethyl ester, carbamic acid 3-[4-(4-chloro-benzyloxy)-phenyl]-isoxazol-5-ylmethyl ester, carbamic acid 3-[4-(2,6-dichloro-benzyloxy)-phenyl]-isoxazol-5-ylmethyl ester, carbamic acid 3-[4-(2,5-dichloro-benzyloxy)-phenyl]-isoxazol-5-ylmethyl ester, carbamic acid 3-[4-(2-chloro-5-fluoro-benzyloxy)-phenyl]-isoxazol-5-ylmethyl ester, carbamic acid 3-[4-(3-nitro-benzyloxy)-phenyl]-isoxazol-5-ylmethyl ester, 4-[4-(5-carbamoyloxymethyl-isoxazol-3-yl)-phenoxymethyl]-benzoic acid methyl ester, carbamic acid 3-[4-(4-methyl-benzyloxy)-phenyl]-isoxazol-5-ylmethyl ester, carbamic acid 3-[4-(2-methyl-benzyloxy)-phenyl]-isoxazol-5-ylmethyl ester, carbamic acid 3-[4-(3-methoxy-benzyloxy)-phenyl]-isoxazol-5-ylmethyl ester, 3-[4-(3-trifluoromethyl-benzyloxy)-phenyl]-isoxazol-5-ylmethyl ester, carbamic acid 3-[4-(4-isopropyl-benzyloxy)-phenyl]-isoxazol-5-ylmethyl ester, carbamic acid 3-[4-(4-tert-butyl-benzyloxy)-phenyl]-isoxazol-5-ylmethyl ester, carbamic acid 3-[4-(biphenyl-4-ylmethoxy)-phenyl]-isoxazol-5-ylmethyl ester, carbamic acid 3-[4-(3-formyl-benzyloxy)-phenyl]-isoxazol-5-ylmethyl ester, carbamic acid 3-[4-(4-formyl-benzyloxy)-phenyl]-isoxazol-5-ylmethyl ester, carbamic acid 3-{4-[4-(hydroxyimino-methyl)-benzyloxy]-phenyl}-isoxazol-5-ylmethyl ester, carbamic acid 3-{4-[3-(hydroxyimino-methyl)-benzyloxy]-phenyl}-isoxazol-5-ylmethyl ester, carbamic acid 3-(4-methoxy-phenyl)-isoxazol-5-ylmethyl ester, carbamic acid 3-(4-ethoxy-phenyl)-isoxazol-5-ylmethyl ester, carbamic acid 3-(4-prop-2-ynyloxy-phenyl)-isoxazol-5-ylmethyl ester, carbamic acid 3-(4-propoxy-phenyl)-isoxazol-5-ylmethyl ester, carbamic acid 3-(4-butoxy-phenyl)-isoxazol-5-ylmethyl ester, carbamic acid 3-(4-pentoxy-phenyl)-isoxazol-5-ylmethyl ester, carbamic acid 3-(4-hexyloxy-phenyl)-isoxazol-5-ylmethyl ester, carbamic acid 3-(4-cyclohexylmethoxy-phenyl)-isoxazol-5-ylmethyl ester, [4-(5-carbamoyloxymethyl-isoxazol-3-yl)-phenoxy]-acetic acid ethyl ester, carbamic acid 3-(4-methylsulfanylmethoxy-phenyl)-isoxazol-5-ylmethyl ester, carbamic acid 3-(4-methoxymethoxy-phenyl)-isoxazol-5-ylmethyl ester, {3-[4-(5-carbamoyloxymethyl-isoxazol-3-yl)-phenoxy]-propyl}-carbamic acid tert-butyl ester, carbamic acid 3-[4-(3-ureido-propoxy)-phenyl]-isoxazol-5-ylmethyl ester, carbamic acid 3-[4-(5-carbamoyloxymethyl-isoxazol-3-yl)-phenoxy]-propyl ester, 4-[4-(5-carbamoyloxymethyl-isoxazol-3-yl)-phenoxy]-butyric acid ethyl ester, carbamic acid 3-[4-(3-amino-propoxy)-phenyl]-isoxazol-5-ylmethyl ester, carbamic acid 3-[4-(2-hydroxy-ethoxy)-phenyl]-isoxazol-5-ylmethyl ester, carbamic acid 2-[4-(5-carbamoyloxymethyl-isoxazol-3-yl)-phenoxy]-ethyl ester, carbamic acid 3-[4-(4-hydroxy-butoxy)-phenyl]-isoxazol-5-ylmethyl ester, carbamic acid 3-(4-trifluoromethylsulfanylmethoxy-phenyl)-isoxazol-5-ylmethyl ester, carbamic acid 3-[4-(4,4,4-trifluorobutoxy)-phenyl]-isoxazol-5-ylmethyl ester, carbamic acid 3-[4-(3-cyano-propoxy)-phenyl]-isoxazol-5-ylmethyl ester, carbamic acid 3-[4-(2-imidazol-1-yl-ethoxy)-phenyl]-isoxazol-5-ylmethyl ester, carbamic acid 3-[4-(5-chloro-thiophen-2-ylmethoxy)-phenyl]-isoxazol-5-ylmethyl ester, carbamic acid 3-[4-(naphthalen-2-ylmethoxy)-phenyl]-isoxazol-5-ylmethyl ester, carbamic acid 3-[4-(benzothiazol-2-ylmethoxy)-phenyl]-isoxazol-5-ylmethyl ester, carbamic acid 3-[4-(pyridin-2-ylmethoxy)-phenyl]-isoxazol-5-ylmethyl ester, carbamic acid 3-[4-(pyridin-3-ylmethoxy)-phenyl]-isoxazol-5-ylmethyl ester, carbamic acid 3-[4-(pyridin-4-ylmethoxy)-phenyl]-isoxazol-5-ylmethyl ester, carbamic acid 3-[4-(5-methoxy-4,6-dimethyl-pyridin-2-ylmethoxy)-phenyl]-isoxazol-5-ylmethyl ester, carbamic acid 3-[4-(3,5-dichloro-pyridin-4-ylmethoxy)-phenyl]-isoxazol-5-ylmethyl ester, carbamic acid 3-[4-(quinolin-2-ylmethoxy)-phenyl]-isoxazol-5-ylmethyl ester, carbamic acid 3-[4-(benzotriazol-1-ylmethoxy)-phenyl]-isoxazol-5-ylmethyl ester, carbamic acid 3-[4-(3,5-dimethyl-isoxazol-4-ylmethoxy)-phenyl]-isoxazol-5-ylmethyl ester, 5-[4-(5-carbamoyloxymethyl-isoxazol-3-yl)-phenoxymethyl]-furan-2-carboxylic acid methyl ester, carbamic acid 1-[3-(4-benzyloxy-phenyl)-isoxazol-5-yl]-ethyl ester, carbamic acid 2-[3-(4-benzyloxy-phenyl)-isoxazol-5-yl]-ethyl ester, carbamic acid 3-[4-(1-oxy-pyridin-2-ylmethoxy)-phenyl]-isoxazol-5-ylmethyl ester, carbamic acid 1-[3-(4-benzyloxy-phenyl)-isoxazol-5-yl]-1-methyl-ethyl ester, carbamic acid 1-{3-[4-(pyridin-2-ylmethoxy)-phenyl]-isoxazol-5-yl}-ethyl ester, 2-[4-(5-carbamoyloxymethyl-isoxazol-3-yl)-phenoxymethyl]-1-methyl-pyridinium iodide, carbamic acid 3-(4-cyclopentylmethoxy-phenyl)-isoxazol-5-ylmethyl ester, carbamic acid 3-[4-(2,4-difluoro-benzyloxy)-phenyl]-isoxazol-5-ylmethyl ester, carbamic acid 3-[4-(2,5-difluoro-benzyloxy)-phenyl]-isoxazol-5-ylmethyl ester, carbamic acid 3-[4-(2,4-dichloro-benzyloxy)-phenyl]-isoxazol-5-ylmethyl ester, carbamic acid 3-[4-(2-chloro-6-fluorobenzyloxy)-phenyl]-isoxazol-5-ylmethyl ester, carbamic acid 3-[4-(3-methyl-benzyloxy)-phenyl]-isoxazol-5-ylmethyl ester, carbamic acid 3-[4-(2-trifluoromethyl-benzyloxy)-phenyl]-isoxazol-5-ylmethyl ester, carbamic acid 3-[4-(4-trifluoromethyl-benzyloxy)-phenyl]-isoxazol-5-ylmethyl ester, carbamic acid 3-[4-(benzo[1,3]dioxol-5-ylmethoxy)-phenyl]-isoxazol-5-ylmethyl ester, and carbamic acid 3-{4-[3-(t-butylnitronyl)-benzyloxy]-phenyl}-isoxazol-5-ylmethyl ester.

Examples of the compound, in which Y is N—$R_1$; Z is carbamate; and R, $R_1$-$R_8$, A, B, m, and n are as described above, include carbamic acid 3-(4-benzylamino-phenyl)-isoxazol-5-ylmethyl ester, carbamic acid 3-[4-(benzyl-methyl-amino)-phenyl]-isoxazol-5-ylmethyl ester, carbamic acid 3-[4-(4-fluoro-benzylamino)-phenyl]-isoxazol-5-ylmethyl ester, carbamic acid 3-[4-(3-fluoro-benzylamino)-phenyl]-isoxazol-5-ylmethyl ester, carbamic acid 3-[4-(2-fluoro-benzylamino)-phenyl]-isoxazol-5-ylmethyl ester, carbamic acid 3-[4-(2,6-difluoro-benzylamino)-phenyl]-isoxazol-5-ylmethyl ester, carbamic acid 3-[4-(2,3-difluoro-benzylamino)-phenyl]-isoxazol-5-ylmethyl ester, carbamic acid 3-[4-(2,4-difluoro-benzylamino)-phenyl]-isoxazol-5-ylmethyl ester, carbamic acid 3-[4-(3,5-difluoro-benzylamino)-phenyl]-isoxazol-5-ylmethyl ester, carbamic acid 3-[4-(3,4-difluoro-benzylamino)-phenyl]-isoxazol-5-ylmethyl ester, carbamic acid 3-[4-(2,5-difluoro-benzylamino)-phenyl]-isoxazol-5-ylmethyl ester, carbamic acid 3-[4-(3-chloro-benzylamino)-phenyl]-isoxazol-5-ylmethyl ester, carbamic acid 3-[4-(2-chloro-benzylamino)-phenyl]-isoxazol-5-ylmethyl ester, carbamic acid 3-[4-(4-chloro-benzylamino)-phenyl]-isoxazol-5-ylmethyl ester, carbamic acid 3-[4-(2,3-dichloro-benzylamino)-phenyl]-isoxazol-5-ylmethyl ester, carbamic acid 3-[4-(2,4-dichloro-benzylamino)-phenyl]-isoxazol-5-ylmethyl ester, carbamic acid 3-[4-(2,5-dichloro-benzylamino)-phenyl]-isoxazol-5-ylmethyl ester, carbamic acid 3-[4-(2,6-dichloro-benzylamino)-phenyl]-isoxazol-5-ylmethyl ester, carbamic acid 3-[4-(3,4-dichloro-benzylamino)-phenyl]-isoxazol-5-ylmethyl ester, carbamic acid 3-[4-(3,5-dichloro-benzylamino)-phenyl]-isoxazol-5-ylmethyl ester, carbamic acid 3-[4-(2,3,5-trichloro-benzylamino)-phenyl]-isoxazol-5-ylmethyl ester, carbamic acid 3-[4-(2,3,6-trichloro-benzylamino)-phenyl]-isoxazol-5-ylmethyl ester, carbamic acid 3-[4-(3-trifluoromethyl-benzylamino)-phenyl]-isoxazol-5-ylmethyl ester, carbamic acid 3-[4-(4-trifluoromethyl-benzylamino)-phenyl]-isoxazol-5-ylmethyl ester, carbamic acid 3-[4-(3,5-bis-trifluoromethyl-benzylamino)-phenyl]-isoxazol-5-ylmethyl ester, carbamic acid 3-[4-(2-methyl-benzylamino)-phenyl]-isoxazol-5-ylmethyl ester, carbamic acid 3-[4-(3-methyl-benzylamino)-phenyl]-isoxazol-5-ylmethyl ester, carbamic acid 3-[4-(4-methyl-benzylamino)-phenyl]-isoxazol-5-ylmethyl ester, carbamic acid 3-[4-(4-isopropyl-benzylamino)-phenyl]-isoxazol-5-ylmethyl ester, carbamic acid 3-[4-(2,4-dimethyl-benzylamino)-phenyl]-isoxazol-5-ylmethyl ester, carbamic acid 3-[4-(2-methoxy-benzylamino)-phenyl]-isoxazol-5-ylmethyl ester, carbamic acid 3-[4-(3-methoxy-benzylamino)-phenyl]-isoxazol-5-ylmethyl ester, carbamic acid 3-[4-(4-methoxy-benzylamino)-phenyl]-isoxazol-5-ylmethyl ester, carbamic acid 3-[4-(4-phenoxy-benzylamino)-phenyl]-isoxazol-5-ylmethyl ester, carbamic acid 3-[4-(4-benzyloxy-benzylamino)-phenyl]-isoxazol-5-ylmethyl ester, carbamic acid 3-{4-[(5-phenyl-isoxazol-3-ylmethyl)-amino]-phenyl}-isoxazol-5-ylmethyl ester, carbamic acid 3-{4-[(thiophen-2-ylmethyl)-amino]-phenyl}-isoxazol-5-ylmethyl ester, carbamic acid 3-{4-[(furan-3-ylmethyl)-amino]-phenyl}-isoxazol-5-ylmethyl ester, carbamic acid 3-{4-[(3,5-dimethyl-isoxazol-4-ylmethyl)-amino]-phenyl}-isoxazol-5-ylmethyl ester, carbamic acid 3-[4-(3,5-di-tert-butyl-4-hydroxy-benzylamino)-phenyl]-isoxazol-5-ylmethyl ester, carbamic acid 3-[4-(3,5-dimethyl-4-hydroxy-benzylamino)-phenyl]-isoxazol-5-ylmethyl ester, carbamic acid 3-[4-(3,5-di-tert-butyl-benzylamino)-phenyl]-isoxazol-5-ylmethyl ester, carbamic acid 3-[4-(3,4,5-trihydroxy-benzylamino)-phenyl]-isoxazol-5-ylmethyl ester, carbamic acid 3-[4-(benzyl-ethyl-amino)-phenyl]-isoxazol-5-ylmethyl ester, and carbamic acid 3-[4-(benzyl-propyl-amino)-phenyl]-isoxazol-5-ylmethyl ester.

Examples of the compound, in which Y is O; Z is O—C(=O)NR$_3$R$_4$; and R, R$_1$-R$_8$, A, B, m, and n are as described above, include imidazole-1-carboxylic acid 3-(4-benzyloxy-phenyl)-isoxazol-5-ylmethyl ester, methyl-carbamic acid 3-(4-benzyloxy-phenyl)-isoxazol-5-ylmethyl ester, dimethyl-carbamic acid 3-(4-benzyloxy-phenyl)-isoxazol-5-ylmethyl ester, diethyl-carbamic acid 3-(4-benzyloxy-phenyl)-isoxazol-5-ylmethyl ester, ethyl-methyl-carbamic acid 3-(4-benzyloxy-phenyl)-isoxazol-5-ylmethyl ester, pyrrolidine-1-carboxylic acid 3-(4-benzyloxy-phenyl)-isoxazol-5-ylmethyl ester, piperidine-1-carboxylic acid 3-(4-benzyloxy-phenyl)-isoxazol-5-ylmethyl ester, morpholine-4-carboxylic acid 3-(4-benzyloxy-phenyl)-isoxazol-5-ylmethyl ester, piperazine-1-carboxylic acid 3-(4-benzyloxy-phenyl)-isoxazol-5-ylmethyl ester, N',N'-dimethyl-hydrazinecarboxylic acid 3-(4-benzyloxy-phenyl)-isoxazol-5-ylmethyl ester, (3-amino-propyl)-carbamic acid 3-(4-benzyloxy-phenyl)-isoxazol-5-ylmethyl ester, (2-amino-ethyl)-carbamic acid 3-(4-benzyloxy-phenyl)-isoxazol-5-ylmethyl ester, piperidine-1-yl-carbamic acid 3-(4-benzyloxy-phenyl)-isoxazol-5-ylmethyl ester, (4-methyl-piperazin-1-yl)-carbamic acid 3-(4-benzyloxy-phenyl)-isoxazol-5-ylmethyl ester, 4-methyl-piperazin-1-carboxylic acid 3-(4-benzyloxy-phenyl)-isoxazol-5-ylmethyl ester, piperidine-4-yl-carbamic acid 3-(4-benzyloxy-phenyl)-isoxazol-5-ylmethyl ester, and 4-[3-(4-benzyloxy-phenyl)-isoxazol-5-ylmethoxycarbonyl]-[1,4]diazepan-1-ium chloride.

Examples of the compound, in which Y is O; Z is —NR$_5$R$_6$; and R, R$_1$-R$_8$, A, B, m, and n are as described above, include [3-(4-benzyloxy-phenyl)-isoxazol-5-ylmethyl]-prop-2-ynyl-amine, 1-[3-(4-benzyloxy-phenyl)-isoxazol-5-ylmethyl]-piperidin-4-ol, carbamic acid 1-[3-(4-benzyloxy-phenyl)-isoxazol-5-ylmethyl]-piperidin-4-yl ester, 3-(4-benzyloxy-phenyl)-5-imidazol-1-ylmethyl-isoxazole, 3-(4-benzyloxy-phenyl)-5-(2-methyl-imidazol-1-ylmethyl)-isoxazole, 3-(4-benzyloxy-phenyl)-5-(4-methyl-imidazol-1-ylmethyl)-isoxazole, 3-[4-(3-fluoro-benzyloxy)-phenyl]-5-imidazol-1-ylmethyl-isoxazole, 3-[4-(2,6-difluoro-benzyloxy)-phenyl]-5-imidazol-1-ylmethyl-isoxazole, 1-[3-(4-benzyloxy-phenyl)-isoxazol-5-ylmethyl]-1H-[1,2,4]triazole, 1-[3-(4-benzyloxy-phenyl)-isoxazol-5-ylmethyl]-1H-[1,2,3]triazole, 2-[3-(4-benzyloxy-phenyl)-isoxazol-5-ylmethyl]-2H-tetrazole, 1-[3-(4-benzyloxy-phenyl)-isoxazol-5-ylmethyl]-2H-tetrazole, 3-[4-(2,4-difluoro-benzyloxy)-phenyl]-5-imidazol-1-ylmethyl-isoxazole, 5-imidazol-1-ylmethyl-3-[4-(2,4,6-trifluoro-benzyloxy)-phenyl]-isoxazole, 3-[4-(4-fluoro-benzyloxy)-phenyl]-5-imidazol-1-ylmethyl-isoxazole, 3-[4-(4-chloro-benzyloxy)-phenyl]-5-imidazol-1-ylmethyl-isoxazole, 3-[4-(4-fluoro-benzyloxy)-phenyl]-5-(4-methyl-imidazol-1-ylmethyl)-isoxazole, 3-[4-(3-fluoro-benzyloxy)-phenyl]-5-(4-methyl-imidazol-1-ylmethyl)-isoxazole, 3-[4-(2,4-difluoro-benzyloxy)-phenyl]-5-(4-methyl-imidazol-1-ylmethyl)-isoxazole, 3-(4-benzyloxy-phenyl)-5-pyrrolidin-1-ylmethyl-isoxazole, 1-[3-(4-benzyloxy-phenyl)-isoxazol-5-ylmethyl]-piperidine, [3-(4-benzyloxy-phenyl)-isoxazol-5-ylmethyl]-dimethyl-amine, [3-(4-benzyloxy-phenyl)-isoxazol-5-ylmethyl]-diethyl-amine, [3-(4-benzyloxy-phenyl)-isoxazol-5-ylmethyl]-urea, N-[3-(4-benzyloxy-phenyl)-isoxazol-5-ylmethyl]-guanidine, 2-{[3-(4-benzyloxy-phenyl)-isoxazol-5-ylmethyl]-amino}-acetamide, 2-{[3-(4-benzyloxy-phenyl)-isoxazol-5-ylmethyl]-amino}-propionamide, 2-{[3-(4-benzyloxy-phenyl)-isoxazol-5-ylmethyl]-amino}-2-methyl-propionamide, carbamic acid 2-{[3-(4-benzyloxy-phenyl)-isoxazol-5-ylmethyl]-amino}-propyl ester hydrochloride, 2-{[3-(4-benzyloxy-phenyl)-isoxazol-5-ylmethyl]-amino}-3-hydroxy-propionamide, 2-{[3-(4-benzyloxy-phenyl)-isoxazol-5-ylmethyl]-amino}-ethanol, 2-{[3-(4-benzyloxy-phenyl)-isoxazol-5-ylmethyl]-amino}-propan-1-ol, 2-{[3-(4-benzyloxy-phenyl)-isoxazol-5-ylmethyl]-amino}-butan-1-ol, 2-{[3-(4-benzyloxyphenyl)-isoxazol-5-ylmethyl]-amino}-2-methyl-propan-1-ol, 2-{[3-(4-benzyloxy-phenyl)-isoxazol-5-ylmethyl]-amino}-3-methyl-butan-1-ol, 2-{[3-(4-benzyloxy-phenyl)-isoxazol-5-ylmethyl]-amino}-propan-1,3-diol, [3-(4-benzyloxy-phenyl)-isoxazol-5-ylmethyl]-(2-methoxy-ethyl)-amine, allyl-[3-(4-benzyloxy-phenyl)-isoxazol-5-ylmethyl]-amine, carbamic acid 2-{[3-(4-benzyloxy-phenyl)-isoxazol-5-ylmethyl]-amino}-ethyl ester, [3-(4-benzyloxy-phenyl)-isoxazol-5-ylmethyl]-methyl-prop-2-ynyl-amine, 3-(4-benzyloxy-phenyl)-5-(2-isopropyl-imidazol-1-ylmethyl)-isoxazole, 3-(4-benzyloxy-phenyl)-5-(4-bromo-imidazol-1-ylmethyl)-isoxazole, 3-(4-benzyloxy-phenyl)-5-(4,5-dichloro-imidazol-1-ylmethyl)-isoxazole, 3-(4-benzyloxy-phenyl)-5-(2-methyl-4,5-dichloro-imidazol-1-ylmethyl)-isoxazole, 3-(4-benzyloxy-phenyl)-5-(2-nitro-imidazol-1-ylmethyl)-isoxazole, 3-(4-benzyloxy-phenyl)-5-(4-phenyl-imidazol-1-ylmethyl)-isoxazole, 3-(4-benzyloxy-phenyl)-5-(4-nitro-imidazol-1-ylmethyl)-isoxazole, 3-(4-benzyloxy-phenyl)-5-(2-ethyl-4-methyl-imidazol-1-ylmethyl)-isoxazole, 3-(4-benzyloxy-phenyl)-5-(2-chloroimidazol-1-ylmethyl)-isoxazole, 3-(4-benzyloxy-phenyl)-5-(2-bromoimidazol-1-ylmethyl)-isoxazole, 3-(4-benzyloxy-phenyl)-5-(2-bromo-4,5-dichloroimidazol-1-ylmethyl)-isoxazole, 3-(4-benzyloxy-phenyl)-5-(2,4,5-tribromo-imidazol-1-ylmethyl)-isoxazole, and 3-(4-benzyloxy-phenyl)-5-(2-ethyl-imidazol-1-ylmethyl)-isoxazole.

One embodiment of the present invention provides pharmaceutical compositions for treatment of Parkinson's disease containing the substituted azole derivative as an active ingredient and a pharmaceutically acceptable carrier.

In preparation of the pharmaceutical compositions, a carrier may be selected according to a formulation for preparation and may be mixed with the azole derivative of Formula (I) as an active ingredient in an appropriate ratio for formulation.

The carrier is typically used in preparation, and includes, but is not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxy-benzoate, talc, magnesium stearate, and mineral oil.

It is found that the MAO enzyme is involved in dopamine degradation, resulting in oxidative damage which contributes to the cause of degenerative brain disease such as Alzheimer's and Parkinson's disease. More specifically, it is known that MAO-A and MAO-B overexpressed in glial cells and astrocytes of the brain of a patient with dementia respectively are responsible for the oxidative damage.

As confirmed in Table 1 in the following Example 205, the azole derivatives of

Formula (I) and pharmaceutically useful salts thereof have potent inhibition of MAO-B activity, and thus the compound of Formula (I) may be used alone or in combination with pharmaceutically acceptable carriers, as a therapeutic agent for brain disease, including Parkinson's disease.

The pharmaceutical compositions may be specifically formulated for administration by any suitable route such as the oral, rectal, nasal, pulmonary, topical, transdermal, intracisternal, intraperitoneal, vaginal and parenteral (including subcutaneous, intramuscular, intrathecal, intravenous and intradermal) route, the oral route being preferred. When the oral preparation is prepared, conventional pharmaceutical carriers may be used. For oral liquid dosage forms such as suspensions, syrups, elixirs and solutions, acceptable carriers may include, for example, water, glycol, oil, alcohol, etc. For solid oral dosage forms such as powders, pills, capsules, and tablets, carriers may include starch, sugar, kaolin, lubricants, binders, disintegrating agents, etc. The preferred route will depend on the general condition and age of the subject to be treated, the nature of the condition to be treated, and the active ingredient chosen. For easy administration and uniform dosage, it is preferably prepared in unit dosage form.

The pharmaceutical compositions to be prepared according to one embodiment of the present invention may be administered by any suitable route, for example orally in the form of tablets, capsules, powders, granules, pellets, troches, dragees, pills or lozenges, solutions or suspensions in aqueous or non-aqueous liquids, or oil-in-water or water-in-oil liquid emulsions, elixirs, syrups, etc., or parenterally in the form of solutions for injection. Other pharmaceutical compositions for parenteral administration include dispersions, suspensions or emulsions as well as sterile powders to be reconstituted in sterile injectable solutions or dispersions prior to use. Depot injectable formulations are also considered as being within the scope of the present invention. Other suitable administration forms include suppositories, sprays, ointments, creams, gels, inhalants, dermal patches, etc. For preparing such compositions, methods well known in the art may be used, and any pharmaceutically acceptable carriers, diluents, excipients or other additives normally used in the art may be used.

One embodiment of the present invention provides a method for treating Parkinson's disease in a mammal by administering an effective amount of the substituted azole derivative to the mammal.

The term "effective amount" means an amount of active ingredient effective to alleviate or reduce symptoms of a disease requiring treatment, or to reduce or retard the onset of clinical markers or symptoms of a disease in need of prevention. The therapeutically effective amount may be empirically determined by experimenting with compounds of interest in known in vivo and in vitro model systems for a disease requiring treatment.

When the active ingredient of the composition, specifically the azole derivative of Formula (I), is administered for clinical purpose, the active ingredient is typically administered in unit dosage form or divided dosage form, containing an amount of about 0.01 mg to about 100 mg of the active ingredient. The total daily dosage is about 0.01 mg to about 100 mg per kg of body weight and preferably about 0.1 mg to about 10 mg per kg of body weight. However, assessing the conditions of a patient thoroughly and considering the activity of the drug to be administered, a specific dosage which is not included in the range may be administered.

In addition, when the azole derivative of Formula (I) is administered in combination with Levodopa, the derivative shows efficacy at lower dosage than when it is solely administered. Thus, the azole derivative may be administered along with Levodopa. Levodopa, a precursor of dopamine, functions to supplement low levels of dopamine in the substantia nigra and thus has been used as a therapeutic agent for Parkinson's disease. Levadopa is preferably administered with a DOPA decarboxylase inhibitor as a supplement to maintain the mobility of Levodopa by preventing Levodopa from being absorbed in the peripheral zone and increase the bioavailability of Levodopa. The DOPA decarboxylase inhibitor may include, but is not limited to, preferably benserazide, carbidopa, etc.

When the azole derivative of Formula (I) is administered in combination with Levodopa, preferably the Levodopa is administered with DOPA decarboxylase inhibitor. Thus, a group which is administered Levodopa with DOPA decarboxylase inhibitor can be called 'a Levodopa goup' for convenience in the present detailed description. That is 'a Levodopa goup' means administering Levodopa with DOPA decarboxylase inhibitor.

When the azole derivative of Formula (I) is administered in combination with Levodopa, the azole derivative may be administered in unit dosage form containing an amount of about 0.001 mg to about 100 mg of azole derivative per kg of body weight in combination with about 0.5 mg to about 100 mg of Levodopa per kg of body weight and about 0.1 mg to about 10 mg of DOPA decarboxylase inhibitor per kg of body weight. When administered to a human subject, the ratio of the Levodopa to the DOPA decarboxylase inhibitor is preferably about 4:1, and the ratio of the azole derivative of Formula (I) to the Levodopa is preferably about 1:50-1:5000, but is not limited to the range.

In the combinatorial administration, it is preferred that the azole derivative of Formula (I), benserazide, and DOPA carboxylase inhibitor are orally administered, and the azole derivative may be orally administered and benserazide and DOPA decarboxylase inhibitor may be intraperitoneally administered. However, the administration route is not limited thereto. It is preferred that the azole derivative, benserazide, and DOPA decarboxylase inhibitor is simultaneously administered. However, the azole derivative may be administered in advance about 30 to about 60 minutes prior to the administration of Levodopa and DOPA decarboxylase inhibitor in order to sufficiently deliver the absorbed compound after the compound is administered. Levodopa may be also administered about 30 to about 60 minutes after DOPA decarboxylase inhibitor is administered in order to block the absorption of Levodopa in the peripheral nervous system and help in the delivery of Levodopa to the central nervous system. The combinatorial administration may decrease the dose of Levodopa to minimize side effects which may be caused by administration in large doses for a prolonged period.

The daily dosage of the azole derivative is preferably administered once to twice a day. When the azole derivative is administered with Levodopa group as confirmed in Examples for treatment of Parkinson's disease, it can be confirmed that the administration of the azole derivative of Formula (I) in combination with Levodopa group shows better behavior improvement effects than in a single administration group.

It is known that prolonged administration of Levodopa, typically used in treatment of Parkinson's disease, results in reduced efficacy and occurrence of tremors and involuntary hand tremors, and it is also known that when the administration of Levodopa is stopped, an adverse side effect known as "OFF-time" aggravates the symptoms of Parkinson's disease to a more significant level than before the drug was administered (Daniel B. Putterman, et al 2007).

The specific dosage for a specific patient must be empirically determined in determining an optimal dosage under a specific circumstance according to the specific compound to be used, body weight of the patient, sex, health condition, diet, time or method of administration, excretion rate, mixing ratio of the medicine, severity of the disease, etc.

Depending on the situation, the azole derivative of Formula (I) may be used in the form of a prodrug thereof in formulation of an active pharmaceutical composition.

The azole derivative of Formula (I) may be administered in one or several times, in combination with pharmaceutically acceptable carriers or excipients. The pharmaceutical compositions according to one embodiment of the present invention may be formulated as pharmaceutically acceptable carriers or diluents as well as any other known adjuvants and excipients in accordance with conventional techniques. For convenience, the formulation may be present in unit dosage form according to methods known to those skilled in the art of pharmaceutics.

Other ingredients, which do not inhibit the action of an active ingredient or help the action of the active ingredient, may be further added to the composition according to one embodiment of the present invention, and may be formulated in various forms known to those skilled in other arts.

Furthermore, the present invention provides a use of an effective amount of a compound of Formula (I) or a pharmaceutically acceptable salt thereof for treatment of Parkinson's disease, and a use of an effective amount of a compound of Formula (I) or a pharmaceutically acceptable salt thereof for preparation of a medicament suitable for treating Parkinson's disease.

In the use, the effective amount of the compound of Formula (I) or a pharmaceutically acceptable salt thereof is preferably administered to a mammal in combination with Levodopa and DOPA decarboxylase inhibitor.

The compound of Formula (I) or a pharmaceutically acceptable salt thereof is administered in unit dosage form containing about 0.01 mg to about 10 mg, preferably with the total daily dosage of about 0.1 mg to about 10 mg per kg of body weight.

The DOPA decarboxylase may be benserazide or carbidopa.

Hereinafter, the present invention will be described in more detail with reference to the following Examples. However, the Examples are provided only for a better understanding of the present invention and the scope of the present invention should not be construed to be limited thereby in any manner.

MODE FOR THE INVENTION

Example 1

Synthesis of carbamic acid
3-(4-benzyloxy-phenyl)-isoxazole-5-ylmethyl ester 1.1 Synthesis of 4-benzyloxy-benzaldehyde oxime 4-benzyloxybenzaldehyde (4.24 g, 20 mmol) was dissolved with stirring in a mixed solution of ethanol and water (3:1, 100 ml) at 0.2 M. To this added were NH2OH.HCl (2.78 g, 40 mmol) and sodium acetate (2.46 g, 30 mmol,) and the mixture was stirred at room temperature for about 30 minutes. The completion of the reaction was confirmed by liquid chromatography, and then water and ethanol were distilled under reduced pressure to obtain a pale yellow solid compound. The solid compound was extracted three times with water and ethyl acetate, the organic solvent layer was distilled off under reduced pressure, and then a crude compound was recrystallized from ethyl acetate/hexane (1:10) to obtain a white solid compound. The following reaction was performed on the thus-obtained solid without further purification.

1.2 Synthesis of
[3-(4-benzyloxy-phenyl)-isoxazol-5-yl]-methanol 4-benzyloxy-benzaldehyde oxime (2.27 g, 10 mmol-a compound of 92% purity) was dissolved in methylene chloride (40 ml, 0.25 M), to which solution was added propargyl alcohol (1.77 ml, 30 mmol). To the resulting solution was very slowly dropwise added 10% NaOCl (13.7 ml, 20 mmol) at 0° C., using a dropping funnel. After the addition of NaOCl was completed, the mixture was stirred for about 5 hours while increasing the temperature slowly to room temperature.

The completion of the reaction was confirmed by liquid chromatography, and the mixture was distilled under reduced pressure to remove the methylene chloride. Water (200 ml) was added to the residue and the resulting solid was filtered off. The filtered compound was washed with excess of water and finally washed with diethyl ether. The thus-obtained solid compound was recrystallized from ethyl acetate/hexane (1:2) to obtain 2.50 g of [3-(4-benzyloxy-phenyl)-isoxazol-5-yl]-methanol as a white solid.

1H-NMR (CDCl3, 200 MHz) δ 7.7 (d, 2H), 7.4 (m, 4H), 7.1 (d, 2H), 6.5 (s, 1H), 5.1 (s, 2H), 4.8 (s, 2H)

1.3 Synthesis of carbamic acid 3-(4-benzyloxy-phenyl)-isoxazol-5-ylmethyl ester 1.04 ml of chlorosulfonyl isocyanate (12 mmol) was slowly added to [3-(4-benzyloxy-phenyl)-isoxazol-5-yl]-methanol (2.813 g, 10 mmol) in THF (50 ml, 0.2 M) in a 250 ml-flask at −78° C. The consumption of all the starting materials was confirmed by liquid chromatography, and then water was added to the reaction mixture. After 1 hour, the THF was distilled off under reduced pressure, and the resulting solid after addition of 100 ml of water to the mixture was filtered off. The filtered solid was each washed with 100 ml of water and a solution of ethyl acetate/hexane (1/2) and then dried to obtain 3.4 g of a crude product (95.9% pure). The crude compound was recrystallized from an ethyl acetate/hexane/methylene chloride (1/4/1) solution containing 1% MeOH to obtain 2.743 g of carbamic acid 3-(4-benzyloxy-phenyl)-isoxazol-5-ylmethyl ester of 99% purity.

1H-NMR (CDCl3, 200 MHz) δ 7.7 (d, 2H), 7.4 (m, 4H), 7.1 (d, 2H), 6.6 (s, 1H), 5.2 (s, 2H), 5.1 (s, 2H), 4.8 (brs, 2H)

Example 2

Synthesis of carbamic acid 3-(4-benzyloxy-phenyl)-[1,2,4]oxadiazol-5-ylmethyl ester An experiment was performed in the same manner as in Example 1, using ethyl cyanoformate instead of propargyl alcohol.

1H-NMR (CDCl3, 200 MHz) δ 8.1 (d, 2H), 7.5 (m, 4H), 7.1 (d, 2H), 6.6 (s, 1H), 5.2 (s, 2H), 5.0 (s, 2H)

Example 3

Synthesis of carbamic acid 3-(4-benzyloxy-phenyl)-isothiazol-5-ylmethyl ester 3.1 Synthesis of 5-(4-benzyloxy-phenyl)-[1,3,4]oxathiazol-2-one 4-benzyloxybenzamide (0.66 g, 2.98 mmol) and 0.26 ml of chlorocarbonyl sulfenyl chloride were dissolved in 10 ml of benzene, refluxed for 3 hours, and stirred at 50° C. for 12 hours. The organic solvent was distilled off under reduced pressure, and the resulting solid was washed with n-hexane to obtain 0.78 g of 5-(4-benzyloxy-phenyl)-[1,3,4]oxathiazol-2-one.

3.2 Synthesis of 3-(4-benzyloxy-phenyl)-isothiazol-5-carboxylic acid methyl ester 5-(4-benzyloxy-phenyl)-[1,3,4]oxathiazol-2-one (0.4 g, 1.4 mmol) and 0.23 ml of methyl propionate were dissolved in 10 ml of chlorobenzene and then refluxed overnight. The solvent was distilled off under reduced pressure and the obtained crude compound was purified by silica gel column chromatography to obtain 3-(4-benzyloxy-phenyl)-isothiazol-5-carboxylic acid methyl ester as a desired compound.

3.3 Synthesis of carbamic acid 3-(4-benzyloxy-phenyl)-isothiazol-5-ylmethyl ester The 3-(4-benzyloxy-phenyl)-isothiazol-5-carboxylic acid methyl ester obtained above was reduced to alcohol using NaBH4, and then the same procedure as in Example 1-3 was performed to obtain carbamic acid 3-(4-benzyloxy-phenyl)-isothiazol-5-ylmethyl ester as a desired compound.

1H-NMR (CDCl3, 200 MHz) δ 7.8 (d, 2H), 7.3 (m, 4H), 7.0 (d, 2H), 5.3 (s, 2H), 5.1 (s, 2H), 3.7 (s, 1H), 3.6 (brs, 2H)

Example 4

Synthesis of carbamic acid 3-(4-benzyloxy-phenyl)-[1,2,4]thiadiazol-5-ylmethyl ester An experiment was performed in the same manner as in Example 3, using ethyl cyanoformate instead of methyl propionate.

1H-NMR (CDCl3, 200 MHz) δ 8.2 (d, 2H), 7.4 (m, 4H), 7.0 (d, 2H), 5.5 (s, 2H), 5.1 (s, 2H)

Example 5

Synthesis of carbamic acid 3-(4-benzyloxy-2-chloro-phenyl)-isoxazol-5-ylmethyl ester 5.1 Synthesis of 4-benzyloxy-2-chloro-benzaldehyde 3-chloro-4-hydroxybenzaldehyde (1.0 g, 6.3 mmol), potassium carbonate (1.7 g, 12.3 mmol), and t-butylammonium iodide (1.0 g, 2.7 mmol) were dissolved in acetonitrile (40 ml, 0.16 M), to which solution was slowly added dropwise benzyl bromide (1.2 ml, 9.4 mmol), and reacted at room temperature overnight. The completion of the reaction was confirmed by liquid chromatography, and then acetonitrile was distilled under reduced pressure. A crude solid compound was extracted with ethyl acetate and the solvent was distilled under reduced pressure to obtain a white solid compound. This was recrystallized from ethyl acetate/hexane (1:9) to obtain 1.4 g of 4-benzyloxy-2-chloro-benzaldehyde as a white solid compound.

5.2 Synthesis of carbamic acid 3-(4-benzyloxy-2-chloro-phenyl)-isoxazol-5-ylmethyl ester Instead of 4-benzyloxybenzaldehyde, the 4-benzyloxy-2-chloro-benzaldehyde obtained above was used in the same manners as in Examples 1-1, 1-2, and 1-3 to obtain carbamic acid 3-(4-benzyloxy-2-chloro-phenyl)-isoxazol-5-ylmethyl ester as a desired compound.

1H-NMR (CDCl3, 200 MHz) δ 7.7 (d, 1H), 7.4 (m, 5H), 7.1 (d, 1H), 6.98 (dd, 1H), 6.78 (s, 1H), 5.24 (s, 2H), 5.11 (s, 2H), 4.84 (brs, 2H)

Example 6

Synthesis of carbamic acid 3-(4-benzyloxy-3-bromo-phenyl)-isoxazol-5-ylmethyl ester An experiment was performed in the same manner as in Example 5, using 3-bromo-4-hydroxybenzaldehyde instead of 4-benzyloxy-2-chloro-benzaldehyde.

1H-NMR (CDCl3, 200 MHz) δ 8.03 (s, 1H), 7.67 (d, 1H), 7.4 (m, 5H), 7.02 (d, 1H), 6.58 (s, 1H), 5.22 (s, 4H), 4.76 (brs, 2H)

Example 7

Synthesis of carbamic acid 3-(4-benzyloxy-3-chloro-phenyl)-isoxazol-5-ylmethyl ester An experiment was performed in the same manner as in Example 5, using 2-chloro-4-hydroxybenzaldehyde.
1H-NMR (CDCl3, 200 MHz) δ 7.85 (d, 1H), 7.66 (d, 1H), 7.41 (m, 5H), 7.03 (d, 1H), 6.58 (s, 1H), 5.22 (s, 4H), 4.79 (brs, 2H)

Example 8

Synthesis of carbamic acid 3-(4-benzyloxy-3-fluoro-phenyl)-isoxazol-5-ylmethyl ester An experiment was performed in the same manner as in Example 5, using 2-fluoro-4-hydroxybenzaldehyde.
1H-NMR (CDCl3, 200 MHz) δ 7.57 (d, 1H), 7.40 (m, 6H), 7.08 (t, 1H), 6.56 (s, 1H), 5.21 (s, 4H), 4.77 (brs, 2H)

Example 9

Synthesis of carbamic acid 3-(4-benzyloxy-3,5-dimethyl-phenyl)-isoxazol-5-ylmethyl ester An experiment was performed in the same manner as in Example 5, using 3,5-dimethyl-4-hydroxybenzaldehyde.
1H-NMR (CDCl3, 200 MHz) δ 7.42 (m, 7H), 6.60 (s, 1H), 5.21 (s, 4H), 4.77 (brs, 2H)

Example 10

Synthesis of carbamic acid 3-[4-(1-phenyl-ethoxy)-phenyl]-isoxazol-5-ylmethyl ester 10.1 Synthesis of carbamic acid 3-(4-hydroxy-phenyl)-isoxazol-5-ylmethyl ester Carbamic acid 3-(4-benzyloxy-phenyl)-isoxazol-5-ylmethyl ester was obtained in the same manners as in Examples 1-1, 1-2, and 1-3 in Example 1. The compound was dissolved in MeOH, and underwent a hydrogenation using 10 wt % Pd/C to synthesize carbamic acid 3-(4-hydroxy-phenyl)-isoxazol-5-ylmethyl ester.

10.2 Synthesis of carbamic acid 3-[4-(1-phenyl-ethoxy)-phenyl]-isoxazol-5-ylmethyl ester Carbamic acid 3-(4-hydroxy-phenyl)-isoxazol-5-ylmethyl ester (150 mg, 0.64 mmol) and potassium carbonate (180 mg, 1.28 mmol) were dissolved in 10 ml of acetonitrile, to which was added dropwise (1-bromoethyl)benzene (131 μl, 0.96 mmol), and reacted at room temperature overnight. The completion of the reaction was confirmed by liquid chromatography, and then acetonitrile was distilled under reduced pressure. A crude solid compound was extracted with ethyl acetate and the solvent was distilled under reduced pressure to obtain a white solid compound. This was recrystallized from methylene chloride:MeOH (9:1) to obtain carbamic acid 3-[4-(1-phenyl-ethoxy)-phenyl]-isoxazol-5-ylmethyl ester as a white solid compound.

1H-NMR (CDCl3, 200 MHz) δ 7.65 (d, 2H), 7.35 (m, 5H), 6.94 (d, 2H), 6.53 (d, 2H), 5.38 (s, 1H), 5.19 (s, 2H), 4.84 (brs, 2H), 1.67 (s, 3H)

Example 11

Synthesis of carbamic acid 3-[4-(2-fluoro-benzyloxy)-phenyl]-isoxazol-5-ylmethyl ester The compound was synthesized using 2-fluorobenzyl bromide in the same manner as in Example 10.
1H-NMR (CDCl3, 200 MHz) δ 7.76 (d, 2H), 7.52 (t, 1H), 7.15 (m, 3H), 7.07 (d, 2H), 5.23 (s, 2H), 5.20 (s, 2H) 4.82 (brs, 2H)

Example 12

Synthesis of carbamic acid 3-[4-(3-fluoro-benzyloxy)-phenyl]-isoxazol-5-ylmethyl ester The compound was synthesized using 3-fluorobenzyl bromide in the same manner as in Example 10.
1H-NMR (DMSO, 200 MHz) δ 7.79 (d, 2H), 7.52 (m, 4H), 7.14 (d, 2H), 6.99 (s, 1H), 5.20 (s, 2H), 5.12 (s, 2H)

Example 13

Synthesis of carbamic acid 3-[4-(4-fluoro-benzyloxy)-phenyl]-isoxazol-5-ylmethyl ester The compound was synthesized using 4-fluorobenzyl bromide in the same manner as in Example 10.
1H-NMR (CDCl3, 200 MHz) δ 7.76 (d, 2H), 7.43 (t, 2H), 7.10 (m, 4H), 6.60 (s, 1H), 5.23 (s, 2H), 4.78 (brs, 2H)

Example 14

Synthesis of carbamic acid 3-[4-(2,6-difluoro-benzyloxy)-phenyl]-isoxazol-5-ylmethyl ester The compound was synthesized using 2,6-di-fluorobenzyl bromide in the same manner as in Example 10.
1H-NMR (CDCl3, 200 MHz) δ 7.75 (d, 2H), 7.30 (m, 1H), 7.07 (d, 2H), 6.94 (t, 2H), 6.57 (s, 1H), 5.20 (s, 2H), 5.16 (s, 2H), 4.91 (brs, 2H)

Example 15

Synthesis of carbamic acid 3-[4-(2,3-difluoro-benzyloxy)-phenyl]-isoxazol-5-ylmethyl ester The compound was synthesized using 2,3-di-fluorobenzyl bromide in the same manner as in Example 10.
1H-NMR (CDCl3, 200 MHz) δ 7.70 (d, 2H), 6.96 (m, 3H), 6.72 (d, 2H), 6.55 (s, 1H), 5.18 (s, 2H), 5.06 (s, 2H), 4.77 (brs, 2H)

Example 16

Synthesis of carbamic acid 3-[4-(3,5-difluoro-benzyloxy)-phenyl]-isoxazol-5-ylmethyl ester The compound was synthesized using 2,6-di-fluorobenzyl bromide in the same manner as in Example 10.
1H-NMR (CDCl3, 200 MHz) δ 7.76 (d, 2H), 7.20 (m, 3H), 7.03 (d, 2H), 6.60 (s, 1H), 5.23 (s, 2H), 5.08 (s, 2H), 4.84 (brs, 2H)

Example 17

Synthesis of carbamic acid 3-[4-(3,4-difluoro-benzyloxy)-phenyl]-isoxazol-5-ylmethyl ester The compound was synthesized using 3,4-di-fluorobenzyl bromide in the same manner as in Example 10.

1H-NMR (CDCl3, 200 MHz) δ 7.77 (d, 2H), 7.01 (m, 4H), 6.79 (t, 1H), 6.60 (s, 1H), 5.23 (s, 2H), 5.11 (s, 2H), 4.84 (brs, 2H)

Example 18

Synthesis of carbamic acid 3-[4-(2,4,6-trifluoro-benzyloxy)-phenyl]-isoxazol-5-ylmethyl ester The compound was synthesized using 2,4,6-tri-fluorobenzyl bromide in the same manner as in Example 10.

1H-NMR (CDCl3, 200 MHz) δ 7.54 (d, 2H), 6.86 (d, 2H), 6.56 (t, 2H), 6.45 (s, 1H), 4.98 (s, 2H), 4.91 (s, 2H)

Example 19

Synthesis of carbamic acid 3-[4-(3-trifluoromethyl-benzyloxy)-phenyl]-isoxazol-5-ylmethyl ester The compound was synthesized using 3-trifluoromethyl-benzyl bromide in the same manner as in Example 10.

1H-NMR (CDCl3, 200 MHz) δ 7.74 (d, 2H), 7.58 (d, 2H), 6.58 (1, 1H), 5.20 (s, 1H), 5.15 (s, 2H), 4.70 brs, 2H)

Example 20

Synthesis of 3-[4-(3-chloro-benzyloxy)-phenyl]-isoxazol-5-ylmethyl ester

The compound was synthesized using 3-chlorobenzyl bromide in the same manner as in Example 10.

1H-NMR (CDCl3, 200 MHz) δ 7.74 (d, 2H), 7.44 (s, 1H), 7.30 (m, 3H), 7.03 (d, 2H), 6.58 (s, 1H), 5.21 (s, 2H), 5.09 (s, 2H), 4.78 (brs, 2H)

Example 21

Synthesis of carbamic acid 3-[4-(2-chloro-benzyloxy)-phenyl]-isoxazol-5-ylmethyl ester The compound was synthesized using 2-chlorobenzyl bromide in the same manner as in Example 10.

1H-NMR (CDCl3, 200 MHz) δ 7.74 (d, 2H), 7.44 (s, 1H), 7.30 (m, 3H), 7.03 (d, 2H), 6.58 (s, 1H), 5.21 (s, 2H), 5.09 (s, 2H), 4.78 (brs, 2H)

Example 22

Synthesis of carbamic acid 3-[4-(4-chloro-benzyloxy)-phenyl]-isoxazol-5-ylmethyl ester The compound was synthesized using 4-chlorobenzyl bromide in the same manner as in Example 10.

1H-NMR (DMSO, 200 MHz) δ 7.80 (d, 2H), 7.48 (m, 4H), 7.13 (d, 2H), 7.78 (brs, 2H), 6.99 (s, 1H), 5.18 (s, 2H), 5.12 (s, 2H)

Example 23

Synthesis of carbamic acid 3-[4-(2,6-dichlorobenzyloxy)-phenyl]-isoxazol-5-ylmethyl ester The compound was synthesized using 2,6-dichlorobenzylbromide in the same manner as in Example 10.

1H-NMR (CDCl3, 200 MHz) δ 7.78 (d, 2H), 7.38 (m, 3H), 7.11 (d, 2H), 6.61 (s, 1H), 5.34 (s, 2H), 5.24 (s, 2H), 4.79 (brs, 2H)

Example 24

Synthesis of carbamic acid 3-[4-(2,5-di-chloro-benzyloxy)-phenyl]-isoxazol-5-ylmethyl ester The compound was synthesized using 2,5-dichlorobenzyl bromide in the same manner as in Example 10.

1H-NMR (CDCl3, 200 MHz) δ 7.79 (d, 2H), 7.60 (s, 1H), 7.32 (m, 2H), 7.08 (d, 2H), 6.61 (s, 1H), 5.24 (s, 2H), 5.19 (s, 2H), 4.79 (brs, 2H)

Example 25

Synthesis of carbamic acid 3-[4-(2-chloro-5-fluoro-benzyloxy)-phenyl]-isoxazol-5-ylmethyl ester The compound was synthesized using 2-chloro-5-fluorobenzyl bromide in the same manner as in Example 10.

1H-NMR (CDCl3, 200 MHz) δ 7.78 (d, 2H), 7.29 (m, 3H), 7.10 (d, 2H), 6.61 (s, 1H), 5.24 (s, 4H), 4.82 (brs, 2H)

Example 26

Synthesis of carbamic acid 3-[4-(3-nitro-benzyloxy)-phenyl]-isoxazol-5-ylmethyl ester The compound was synthesized using 3-nitrobenzyl bromide in the same manner as in Example 10.

1H-NMR (CDCl3, 200 MHz) δ 8.4 (s, 1H), 8.2 (d, 1H), 7.8 (d, 2H), 7.6 (t, 1H), 7.1 (d, 2H), 6.6 (s, 1H), 5.2 (s, 4H)

Example 27

Synthesis of 4-[4-(5-carbamoyloxymethyl-isoxazol-3-yl)-phenoxymethyl]-benzoic acid methyl ester The compound was synthesized using methyl 4-(bromomethyl)benzoate in the same manner as in Example 10.

1H-NMR (CDCl3, 200 MHz) δ 8.1 (d, 2H), 7.8 (d, 2H), 7.6 (d, 2H), 7.1 (d, 2H), 6.6 (s, 1H), 5.3 (s, 2H), 5.2 (s, 2H), 4.0 (s, 3H)

Example 28

Synthesis of 3-[4-(4-methyl-benzyloxy)-phenyl]-isoxazol-5-ylmethyl ester

The compound was synthesized using 4-methylbezyl bromide in the same manner as in Example 10.

1H-NMR (CDCl3, 200 MHz) δ 7.5 (d, 2H), 7.1 (d, 2H), 7.0 (d, 2H), 6.8 (d, 2H), 6.5 (s, 1H), 5.0 (s, 2H), 4.9 (s, 2H), 2.2 (s, 3H)

Example 29

Synthesis of carbamic acid 3-[4-(2-methyl-benzyloxy)-phenyl]-isoxazol-5-ylmethyl ester The compound was synthesized using 2-methylbezyl bromide in the same manner as in Example 10.
1H-NMR (CDCl3, 200 MHz) δ 7.6 (d, 2H), 7.3 (s, 1H), 7.1 (m, 3H), 7.0 (d, 2H), 6.5 (s, 1H), 5.1 (s, 2H), 5.0 (s, 2H), 2.2 (s, 3H)

Example 30

Carbamic acid 3-[4-(3-methoxy-benzyloxy)-phenyl]-isoxazol-5-ylmethyl ester

The compound was synthesized using 2-methoxybenzyl bromide in the same manner as in Example 10.
1H-NMR (DMSO, 200 MHz) δ 7.81 (d, 2H), 7.30 (t, 1H), 7.13 (d, 2H), 6.98 (m, 6H), 5.16 (s, 2H), 5.13 (s, 2H), 3.77 (s, 3H)

Example 31

Carbamic acid 3-[4-(3-trifluoromethyl-benzyloxy)-phenyl]-isoxazol-5-ylmethyl ester The compound was synthesized using 3-trifluoromethyl-benzyl bromide in the same manner as in Example 10.
1H-NMR (CDCl3, 200 MHz) δ 7.74 (d, 2H), 7.52 (m, 4H), 7.07 (d, 2H), 6.59 (s, 1H), 5.33 (s, 2H), 5.22 (s, 2H), 4.76 (brs, 2H)

Example 32

Carbamic acid 3-[4-(4-isopropyl-benzyloxy)-phenyl]-isoxazol-5-ylmethyl ester

The compound was synthesized using 4-isopropylbenzyl bromide in the same manner as in Example 10.
1H-NMR (CDCl3, 200 MHz) δ 7.74 (d, 2H), 7.32 (dd, 4H), 7.05 (d, 2H), 6.58 (s, 1H), 5.21 (s, 2H), 5.08 (s, 2H), 4.92 (brs, 2H), 2.98 (m, 1H), 1.25 (d, 6H)

Example 33

Carbamic acid 3-[4-(4-tert-butyl-benzyloxy)-phenyl]-isoxazol-5-ylmethyl ester

The compound was synthesized using 4-tert-butyl-benzyl bromide in the same manner as in Example 10.
1H-NMR (CDCl3, 200 MHz) δ 7.74 (d, 2H), 7.40 (m, 4H), 7.05 (d, 2H), 6.59 (s, 1H), 5.20 (s, 2H), 5.08 (s, 2H), 4.78 (brs, 2H), 1.32 (s, 9H)

Example 34

Carbamic acid 3-[4-(biphenyl-4-ylmethoxy)-phenyl]-isoxazol-5-ylmethyl ester

The compound was synthesized using 4-(bromomethyl) biphenyl in the same manner as in Example 10.
1H-NMR (CDCl3, 200 MHz) δ 7.70 (d, 2H), 7.48 (m, 9H), 7.01 (d, 2H), 6.57 (s, 1H), 5.14 (s, 2H), 5.11 (s, 2H)

Example 35

Synthesis of carbamic acid 3-[4-(3-formyl-benzyloxy)-phenyl]-isoxazol-5-ylmethyl ester The compound was synthesized using 3-(bromomethyl) benzaldehyde in the same manner as in Example 10.
1H-NMR (CDCl3, 200 MHz) δ 10.1 (s, 1H), 8.1 (s, 1H), 7.9 (d, 1H), 7.8 (m, 3H), 7.6 (t, 1H), 7.0 (d, 2H), 6.6 (s, 1H), 5.23 (s, 4H), 5.2 (s, 2H), 4.8 (brs, 2H)

Example 36

Synthesis of carbamic acid 3-[4-(4-formyl-benzyloxy)-phenyl]-isoxazol-5-ylmethyl ester The compound was synthesized using 4-(bromomethyl) benzaldehyde in the same manner as in Example 10.
1H-NMR (CDCl3, 200 MHz) δ 10.0 (s, 1H), 7.9 (d, 2H), 7.8 (d, 2H), 7.6 (d, 2H), 7.0 (d, 2H), 6.6 (s, 1H), 5.2 (s, 4H), 4.8 (brs, 2H)

Example 37

Synthesis of carbamic acid 3-{4-[4-(hydroxyimino-methyl)-benzyloxy]-phenyl}-isoxazol-5-ylmethyl ester 4-carbamic acid 3-[4-(4-formyl-benzyloxy)-phenyl]-isoxazol-5-ylmethyl ester was synthesized, and then a formation of oxime was performed in the same manner as in Example 1-1 to obtain carbamic acid 3-{4-[4-(hydroxyimino-methyl)-benzyloxy]-phenyl}-isoxazol-5-ylmethyl ester as a desired compound.
1H-NMR (CDCl3, 200 MHz) δ 8.0 (s, 1H), 7.7 (d, 2H), 7.5 (d, 2H), 7.3 (d, 2H), 6.9 (d, 2H), 6.5 (s, 1H), 5.1 (s, 2H), 5.0 (s, 2H)

Example 38

Synthesis of carbamic acid 3-{4-[3-(hydroxyimino-methyl)-benzyloxy]-phenyl}-isoxazol-5-ylmethyl ester 4-carbamic 3-[4-(3-formyl-benzylxoy)-phenyl]-isoxazol-5-ylmethyl ester was synthesized, and then a synthesis was performed in the same manner as in Example 36.
1H-NMR (CDCl3, 200 MHz) δ 8.1 (s, 1H), 7.7 (d, 2H), 7.5 (s, 1H), 7.4 (m, 3H), 7.0 (d, 2H), 6.6 (s, 1H), 5.2 (s, 2H), 5.1 (s, 2H)

Example 39

Synthesis of carbamic acid 3-(4-methoxy-phenyl}-isoxazol-5-ylmethyl ester

The compound was synthesized using iodomethane in the same manner as in Example 10.

1H-NMR (CD3OD, 200 MHz) δ 7.8 (d, 2H), 7.0 (d, 2H), 6.8 (s, 1H), 5.2 (s, 2H), 3.9 (s, 3H)

Example 40

Synthesis of carbamic acid 3-(4-ethoxy-phenyl}-isoxazol-5-ylmethyl ester

The compound was synthesized using iodoethane in the same manner as in Example 10.
1H-NMR (CD3OD, 200 MHz) δ 7.8 (d, 2H), 7.0 (d, 2H), 6.8 (s, 1H), 5.2 (s, 2H), 4.1 (q, 2H), 1.4 (t, 3H)

Example 41

Synthesis of carbamic acid 3-(4-prop-2-ynyloxy-phenyl)-isoxazol-5-ylmethyl ester The compound was synthesized using propargyl bromide in the same manner as in Example 10.
1H-NMR (CD3OD, 200 MHz) δ 7.8 (d, 2H), 7.1 (d, 2H), 6.6 (s, 1H), 5.2 (s, 2H), 2.6 (t, 1H)

Example 42

Synthesis of carbamic acid 3-(4-propoxy-phenyl)-isoxazol-5-ylmethyl ester

The compound was synthesized using iodopropane in the same manner as in Example 10.
1H-NMR (CD3OD, 200 MHz) δ 7.7 (d, 2H), 7.0 (d, 2H), 6.7 (s, 1H), 5.2 (s, 2H), 4.0 (t, 2H), 1.8 (m, 2H), 1.1 (t, 3H)

Example 43

Synthesis of carbamic acid 3-(4-butoxy-phenyl)-isoxazol-5-ylmethyl ester

The compound was synthesized using iodobutane in the same manner as in Example 10.
1H-NMR (CDCl3, 200 MHz) δ 7.7 (d, 2H), 7.0 (d, 2H), 6.6 (s, 1H), 5.3 (s, 2H), 4.8 (brs, 2H), 4.0 (t, 2H), 1.8 (m, 2H), 1.5 (m, 2H), 1.1 (t, 3H)

Example 44

Synthesis of carbamic acid 3-(4-pentoxy-phenyl)-isoxazol-5-ylmethyl ester

The compound was synthesized using iodopentane in the same manner as in Example 10.
1H-NMR (CDCl3, 200 MHz) δ 7.7 (d, 2H), 7.0 (d, 2H), 6.6 (s, 1H), 5.3 (s, 2H), 4.8 (brs, 2H), 4.0 (t, 2H), 1.8 (m, 2H), 1.4 (m, 4H), 1.1 (t, 3H)

Example 45

Synthesis of carbamic acid 3-(4-hexyloxy-phenyl)-isoxazol-5-ylmethyl ester

The compound was synthesized using iodohexane in the same manner as in Example 10.
1H-NMR (CDCl3, 200 MHz) δ 7.7 (d, 2H), 7.0 (d, 2H), 6.6 (s, 1H), 5.3 (s, 2H), 4.8 (brs, 2H), 4.0 (t, 2H), 1.8 (m, 2H), 1.4 (m, 6H), 1.1 (t, 3H)

Example 46

Synthesis of carbamic acid 3-(4-cyclohexylmethoxy-phenyl)-isoxazol-5-ylmethyl ester The compound was synthesized using (bromomethyl)cyclohexane in the same manner as in Example 10.
1H-NMR (CDCl3, 200 MHz) δ 7.7 (d, 2H), 7.0 (d, 2H), 6.6 (s, 1H), 5.2 (s, 2H), 4.8 (brs, 2H), 3.8 (d, 2H), 1.8 (m, 6H), 1.2 (m, 5H)

Example 47

Synthesis of [4-(5-carbamoyloxymethyl-isoxazol-3-yl)-phenoxy]-acetic acid ethyl ester The compound was synthesized using ethyl bromoacetate in the same manner as in Example 10.
1H-NMR (CDCl3, 200 MHz) δ 7.7 (d, 2H), 7.0 (d, 2H), 6.6 (s, 1H), 5.2 (s, 2H), 4.8 (brs, 2H), 4.7 (s, 2H), 4.3 (q, 2H), 1.3 (t, 3H)

Example 48

Synthesis of [carbamic acid 3-(4-methylsulfanyl-methoxy-phenyl)-isoxazol-5-ylmethyl ethyl ester The compound was synthesized using chloromethyl methyl sulfide in the same manner as in Example 10.
1H-NMR (CDCl3, 200 MHz) δ 7.8 (d, 2H), 7.0 (d, 2H), 6.6 (s, 1H), 5.2 (s, 2H), 5.20 (s, 2H), 4.9 (brs, 2H), 2.3 (s, 3H)

Example 49

Synthesis of carbamic acid 3-(4-methoxymethoxy-phenyl)-isoxazol-5-ylmethyl ethyl ester The compound was synthesized using chloromethyl methyl ether in the same manner as in Example 10.
1H-NMR (CDCl3, 200 MHz) δ 7.8 (d, 2H), 7.1 (d, 2H), 6.6 (s, 1H), 5.2 (s, 4H), 4.9 (brs, 2H), 3.5 (s, 3H)

Example 50

Synthesis of carbamic acid {3-[4-(5-carbamoyloxymethyl-isoxazol-3-yl)-phenoxy]-propyl}-carbamic acid tert-butyl ester The compound was synthesized using N-boc-3-bromopropylamine in the same manner as in Example 10.
1H-NMR (CDCl3, 200 MHz) δ 7.7 (d, 2H), 7.0 (d, 2H), 6.6 (s, 1H), 5.2 (s, 2H), 4.8 (brs, 2H), 4.1 (t, 2H), 3.4 (m, 2H), 2.0 (t, 2H), 1.5 (s, 9H)

Example 51

Synthesis of carbamic acid 3-[4-(3-amino-propoxy)-phenyl]-isoxazol-5-ylmethyl ester hydrochloride The compound in Example 50 was stirred in 1M HCl in ethyl acetate solution for 4 hours, and then the obtained solid was filtered to obtain carbamic acid 3-[4-(3-amino-propoxy)-phenyl]-isoxazol-5-ylmethyl ester hydrochloride as a desired compound.

1H-NMR (DMSO-d6, 200 MHz) δ 8.0 (brs, 3H), 7.8 (d, 2H), 7.1 (d, 2H), 7.0 (s, 1H), 5.1 (s, 2H), 4.1 (t, 2H), 3.0 (m, 2H), 2.0 (t, 2H)

Example 52

Synthesis of carbamic acid 3-[4-(5-carbamoyloxymethyl-isoxazol-3-yl)-phenoxy]-propyl ester 4-(5-hydroxymethyl-isoxazol-3-yl)-phenol and 3-bromo-1-propanol were used to synthesize 3-[4-(5-hydroxymethyl-isoxazol-3-yl)-phenoxy]-propan-1-ol in the same manner as in Example 10, and then a carbamoylation of the compound was performed in the same manner as in Example 1-3 to obtain carbamic acid 3-[4-(5-carbamoyloxymethyl-isoxazol-3-yl)-phenoxy]-propyl ester as a desired compound.

1H-NMR (CDCl3, 200 MHz) δ 7.6 (d, 2H), 6.9 (d, 2H), 6.5 (s, 1H), 5.1 (s, 2H), 4.2 (t, 2H), 4.0 (t, 2H), 2.0 (m, 2H)

Example 53

Synthesis of 4-[4-(5-carbamoyloxymethyl-isoxazol-3-yl)-phenoxy]-butyric acid ethyl ester The compound was synthesized using ethyl bromobutyrate in the same manner as in Example 10.
1H-NMR (CDCl3, 200 MHz) δ 7.7 (d, 2H), 6.9 (d, 2H), 6.6 (s, 1H), 5.2 (s, 2H), 4.8 (brs, 2H), 4.2 (q, 2H), 4.1 (t, 2H), 2.5 (t, 2H), 2.1 (m, 2H), 1.3 (t, 3H)

Example 54

Synthesis of carbamic acid 3-[4-(3-ureido-propoxy)-phenyl]-isoxazol-5-ylmethyl ester A carbamoylation of the compound carbamic acid 3-[4-(3-amino-propoxy)-phenyl]-isoxazol-5-ylmethyl hydrochloride in Example 51 was performed to obtain carbamic acid 3-[4-(3-ureido-propoxy)-phenyl]-isoxazol-5-ylmethyl ester as a desired compound.

1H-NMR (DMSO-d6, 200 MHz) δ 7.8 (d, 2H), 7.05 (d, 2H), 7.0 (s, 1H), 6.8 (brs, 2H), 6.0 (brs, 1H), 5.4 (s, 2H), 5.1 (s, 2H), 4.1 (t, 2H), 3.1 (m, 2H), 1.8 (t, 2H)

Example 55

Synthesis of carbamic acid 3-[4-(2-hydroxy-ethoxy)-phenyl]-isoxazol-5-ylmethyl ester 5 equivalents of NaBH4 was added to 200 mg of the compound [4-(5-carbamoyloxymethyl-isoxazol-3-yl)-phenoxy]-acetic acid ethyl ester in Example 47 while stirring in the presence of a 10 ml THF/5 ml water solvent. After stirring for 12 hours, the solvent was distilled off under reduced pressure and 20 ml of 1-N HCl solution was added to the reactants, followed by extraction three times with 20 ml of ethyl acetate. The obtained organic layer was put under reduced pressure to obtain carbamic acid 3-[4-(2-hydroxy-ethoxy)-phenyl]-isoxazol-5-ylmethyl ester as a desired compound.

1H-NMR (DMSO-d6, 200 MHz) δ 7.8 (d, 2H), 7.1 (d, 2H), 7.0 (s, 1H), 6.8 (brs, 2H), 5.2 (s, 2H), 4.0 (t, 2H), 3.7 (t, 2H)

Example 56

Synthesis of carbamic acid 2-[4-(5-carbamoyloxymethyl-isoxazol-3-yl)-phenoxy]-ethyl ester A carbamoylation of the compound carbamic acid 3-[4-(2-hydroxy-ethoxy)-phenyl]-isoxazol-5-ylmethyl ester in Example 55 was performed in the same manner as in Example 1-3 to obtain carbamic acid 2-[4-(5-carbamoyloxymethyl-isoxazol-3-yl)-phenoxy]-ethyl ester as a desired compound.

1H-NMR (DMSO-d6, 200 MHz) δ 7.8 (d, 2H), 7.1 (d, 2H), 7.0 (s, 1H), 6.7 (brs, 2H), 5.1 (s, 2H), 4.2 (t, 2H), 3.4 (m, 2H)

Example 57

Synthesis of carbamic acid 3-[4-(4-hydroxy-butoxy)-phenyl]-isoxazol-5-ylmethyl ester A reduction of the compound 4-[(4-(5-carbamoyloxymethyl-isoxazol-3-yl)-phenoxy]-butyric acid ethyl ester in Example 53 was performed in the same manner as in Example 55 to obtain 3-[4-(4-hydroxy-butoxy)-phenyl]-isoxazol-5-ylmethyl ester as a desired compound.

1H-NMR (DMSO-d6, 200 MHz) δ 7.8 (d, 2H), 7.05 (d, 2H), 7.0 (s, 1H), 6.8 (brs, 2H), 5.1 (s, 2H), 4.0 (t, 2H), 3.4 (t, 2H), 1.7 (m, 2H), 1.6 (m, 2H)

Example 58

Synthesis of carbamic acid 3-(4-trifluoromethylsulfanylmethoxy-phenyl)-isoxazol-5-ylmethyl ester The compound was synthesized using chloromethyl trifluoromethyl sulfide in the same manner as in Example 10.
1H-NMR (CDCl3, 200 MHz) δ 7.8 (d, 2H), 7.0 (d, 2H), 6.6 (s, 1H), 5.6 (s, 2H), 5.2 (s, 2H), 4.8 (brs, 1H)

Example 59

Synthesis of carbamic acid 3-[4-(4,4,4-trifluoro-butoxy)-phenyl]-isoxazol-5-ylmethyl ester The compound was synthesized using 1,1,1-trifluoro-4-bromobutane in the same manner as in Example 10.
1H-NMR (CDCl3, 200 MHz) δ 7.7 (d, 2H), 7.0 (d, 2H), 6.6 (s, 1H), 5.2 (s, 2H), 4.8 (brs, 1H), 4.0 (t, 2H), 2.3 (m, 2H), 2.0 (m, 2H)

Example 60

Synthesis of carbamic acid 3-[4-(3-cyano-propoxy)-phenyl]-isoxazol-5-ylmethyl ester The compound was synthesized using 1-cyano-4-bromobutane in the same manner as in Example 10.
1H-NMR (CDCl3, 200 MHz) δ 7.7 (d, 2H), 7.0 (d, 2H), 6.6 (s, 1H), 5.2 (s, 2H), 4.8 (brs, 1H), 4.1 (t, 2H), 2.6 (t, 2H), 2.1 (m, 2H)

Example 61

Synthesis of carbamic acid 3-[4-(2-imidazol-1-yl-ethoxy)-phenyl]-isoxazol-5-ylmethyl ester {3-[4-(2-chloro-ethoxy)-phenyl]-isoxazol-5-yl}-methanol was synthesized using 4-(5-hydroxymethyl-isoxazol-3-yl)-phenol and 2-bromo-1-chloroethane in the same manner as in Example 10, and then 2 equivalents of imidazole and 3 equivalents of potassium carbonate were added to the compound and refluxed with acetonitrile. After 12 hours of the reaction, the solvent was dried under reduced pressure and purified by column chromatography to obtain {3-[4-(2-imidazol-1-yl-ethoxy)-phenyl]-isoxazol-5-yl}-methanol. A carbamoylation of the compound was performed in the same manner as in Example 1-3 to obtain carbamic acid 3-[4-(2-imidazol-1-yl-ethoxy)-phenyl]-isoxazol-5-ylmethyl ester as a desired compound.

1H-NMR (DMSO-d6, 200 MHz) δ 7.8 (d, 2H), 7.7 (s, 1H), 7.25 (s, 1H), 7.05 (d, 2H), 7.0 (s, 1H), 6.9 (s, 1H), 6.8 (brs, 2H), 5.1 (s, 2H), 4.3 (t, 2H), 4.4 (t, 2H)

Example 62

Carbamic acid 3-[4-(5-chloro-thiophen-2-ylmethoxy)-phenyl]-isoxazol-5-ylmethyl ester The compound was synthesized using 2-chloro-5-(chloromethyl)thiophene in the same manner as in Example 10.

1H-NMR (CDCl3, 200 MHz) δ 7.70 (d, 2H), 7.0 (d, 2H), 6.83 (d, 2H), 6.56 (s, 1H), 5.17 (s, 2H), 5.13 (s, 2H)

Example 63

Carbamic acid 3-[4-(naphthalen-2-ylmethoxy)-phenyl]-isoxazol-5-ylmethyl ester

The compound was synthesized using 2-bromomethyl-naphthalene in the same manner as in Example 10.

1H-NMR (CDCl3, 200 MHz) δ 7.91 (m, 5H), 7.53 (m, 2H), 7.15 (d, 2H), 6.59 (s, 1H), 5.30 (s, 2H), 5.22 (s, 2H)

Example 64

Carbamic acid 3-[4-(benzothiazol-2-ylmethoxy)-phenyl]-isoxazol-5-ylmethyl ester

The compound was synthesized using 2-bromomethyl-1,3-benzothiazole in the same manner as in Example 10.

1H-NMR (CDCl3, 200 MHz) δ 8.0 (d, 1H), 7.8 (d, 1H), 7.7 (d, 2H), 7.4 (m, 2H), 7.1 (d, 2H), 6.6 (s, 2H), 5.5 (s, 2H)

Example 65

Carbamic acid 3-[4-(pyridin-2-ylmethoxy)-phenyl]-isoxazol-5-ylmethyl ester

The compound was synthesized using 2-bromomethylpyridine in the same manner as in Example 10.

1H-NMR (CDCl3, 200 MHz) δ 8.6 (s, 1H), 7.7 (d, 3H), 7.5 (d, 1H), 7.2 (d, 1H), 7.1 (d, 2H), 6.6 (s, 1H), 5.3 (s, 2H), 5.2 (s, 2H), 4.8 (brs, 2H)

Example 66

Carbamic acid 3-[4-(pyridin-3-ylmethoxy)-phenyl]-isoxazol-5-ylmethyl ester

The compound was synthesized using 3-bromomethylpyridine in the same manner as in Example 10.

1H-NMR (CDCl3, 200 MHz) δ 8.7 (s, 1H), 8.6 (s, 1H), 8.0 (d, 1H), 7.7 (d, 2H), 7.5 (s, 1H), 7.0 (d, 2H), 5.2 (s, 4H), 4.7 (brs, 2H)

Example 67

Carbamic acid 3-[4-(pyridin-4-ylmethoxy)-phenyl]-isoxazol-5-ylmethyl ester

The compound was synthesized using 4-bromomethylpyridine in the same manner as in Example 10.

1H-NMR (CDCl3, 200 MHz) δ 8.6 (s, 2H), 8.7 (d, 2H), 7.4 (d, 2H), 6.9 (d, 2H), 5.1 (s, 4H), 4.7 (brs, 2H)

Example 68

Carbamic acid 3-[4-(5-methoxy-4,6-dimethyl-pyridin-2-ylmethoxy)-phenyl]-isoxazol-5-ylmethyl ester The compound was synthesized using 2-chloromethyl-4-methyl-3,5-dimethylpyridine hydrochloride in the same manner as in Example 10.

1H-NMR (DMSO, 200 MHz) δ 8.7 (s, 1H), 7.9 (d, 2H), 7.4 (d, 2H), 7.1 (s, 1H), 6.8 (brs, 2H), 5.6 (s, 2H), 5.2 (s, 2H), 4.1 (s, 3H), 2.5 (s, 3H), 2.4 (s, 3H)

Example 69

Carbamic acid 3-[4-(3,5-dichloro-pyridin-4-ylmethoxy)-phenyl]-isoxazol-5-ylmethyl ester The compound was synthesized using 2,6-dichloro-4-chloromethylpyridine in the same manner as in Example 10.

1H-NMR (CDCl3, 200 MHz) δ 7.8 (s, 2H), 7.3 (s, 2H), 7.0 (d, 2H), 7.7 (d, 2H), 7.5 (s, 1H), 7.0 (d, 2H), 6.5 (s, 1H), 5.2 (s, 2H), 4.8 (s, 2H)

Example 70

Carbamic acid 3-[4-(quinolin-2-ylmethoxy)-phenyl]-isoxazol-5-ylmethyl ester

The compound was synthesized using 2-chloromethylquinoline monohydrochloride in the same manner as in Example 10.

1H-NMR (CDCl3, 200 MHz) δ 8.3 (d, 1H), 8.2 (d, 1H), 7.7 (m, 6H), 7.1 (d, 2H), 6.5 (s, 1H), 5.4 (s, 2H), 5.1 (s, 2H)

Example 71

Carbamic acid 3-[4-(benzotriazol-1-ylmethoxy)-phenyl]-isoxazol-5-ylmethyl ester

The compound was synthesized using 1-chloromethyl-1H-benzotriazole in the same manner as in Example 10.

1H-NMR (CDCl3, 200 MHz) δ 8.0 (d, 1H), 7.7 (d, 2H), 7.6 (d, 1H), 7.5 (d, 1H), 7.1 (d, 2H), 6.6 (s, 2H), 6.51 (s, 1H), 5.1 (s, 2H)

Example 72

Synthesis of carbamic acid 3-[4-(3,5-dimethyl-isoxazol-4-ylmethoxy)-phenyl]-isoxazol-5-ylmethyl ester The compound was synthesized using 4-chloromethyl-3,5-dimethylisoxazole in the same manner as in Example 10.

1H-NMR (CDCl3, 200 MHz) 7.7 (d, 2H), 7.0 (d, 2H), 6.6 (s, 2H), 5.1 (s, 2H), 4.8 (s, 2H), 2.4 (s, 3H), 2.25 (s, 3H)

Example 73

Synthesis of 5-[4-(5-carbamoyloxymethyl-isoxazol-3-yl)-phenoxymethyl]-furan-2-carboxylic acid methyl ester The compound was synthesized using methyl 5-(chloromethyl)-2-furoate in the same manner as in Example 10.

1H-NMR (CDCl3, 200 MHz) 7.7 (d, 2H), 7.1 (d, 1H), 7.0 (d, 2H), 6.5 (s, 2H), 6.5 (d, 1H), 5.1 (s, 2H), 5.0 (s, 2H), 3.8 (s, 3H)

Example 74

Carbamic acid 3-(4-benzylamino-phenyl)-isoxazol-5-ylmethyl ester 74.1 Synthesis of 4-nitro-benzaldehyde oxime 4-nitroaldehyde (3 g, 19.9 mmol) was dissolved with stirring in a mixture of ethanol and H2O (3:1 100 ml). To the solution were added NH2OH.HCl (2.78 g, 40 mmol) and pyridine (1.92 ml, 23.8 mmol) and refluxed for about 2 hours. The completion of the reaction was confirmed by liquid chromatography, and then water and ethanol were distilled under reduced pressure to obtain a pale yellow solid compound. The compound was washed with HCl, and was recrystallized from ethyl acetate/hexane (1:9) to obtain 4-nitro-benzaldehyde oxime which has a white color.

74.2 Synthesis of [3-(4-nitro-phenyl)-isoxazol-5-yl]-methanol 4-nitro-benzaldehyde oxime (2.40 g, 14.4 mmol) was dissolved in methylene chloride (70 ml, 0.2 M), and then propargyl alcohol (2.51 ml, 43.2 mmol) was added to the solution. To the resulting solution was slowly added dropwise 10% NaOCl (17.8 ml, 28.8 mmol) using a dropping funnel. After the addition of NaOCl was completed, the mixture was stirred for about 5 hours while increasing the temperature slowly to room temperature. The completion of the reaction was confirmed by liquid chromatography, and then the mixture was distilled under reduced pressure to remove methylene chloride. Water (200 ml) was added to the residue and the resulting solid was filtered off. The filtered compound was washed with excess of water and finally washed with diethyl ether. The thus-obtained solid compound was recrystallized from ethyl acetate/hexane (1:2) to obtain [3-(4-nitro-phenyl)-isoxazol-5-yl]-methanol in a white sold phase.

74.3 Synthesis of [3-(4-amino-phenyl)-isoxazol-5-yl]-methanol

[3-(4-nitro-phenyl)-isoxazol-5-yl]-methanol (300 mg, 1.58 mmol) was placed in a 250-ml Parr reactor flask, to which were added 50 ml of ethanol and 10 wt % Pd/C. The mixture was reacted under 40 psi of hydrogen in the Parr reactor for about 1 hour. The completion of the reaction was confirmed by TLC, and then a filtrate by means of a celite placed was distilled under reduced pressure to obtain a yellow solid compound. This was recrystallized from ethyl acetate/hexane (1:2) to obtain [3-(4-amino-phenyl)-isoxazol-5-yl]-methanol in a yellow solid state.

74.4 Synthesis of [3-(4-benzylamino-phenyl)-isoxazol-5-yl]-methanol

[3-(4-amino-phenyl)-isoxazol-5-yl]-methanol (185 mg, 0.97 mmol) and benzaldehyde (118 μl, 1.16 mmol) were dissolved in 20 ml of methanol, to which solution was added 2 to 3 drops of acetic acid. The reaction was performed at room temperature for about 1 hour. Sodium cyano borohydride (91 mg, 1.45 mmol) was slowly added to the mixture at 0° C., a reaction was performed for 12 hours while increasing the temperature to room temperature, and then methanol was distilled under reduced pressure to obtain a pale yellow solid compound. The solid compound was extracted three times with water and ethyl acetate, the organic solvent layer was separated and distilled under reduced pressure, and then a crude compound was purified by column chromatography on silica gel using ethyl acetate/hexane (1:2) to obtain [3-(4-(benzylamino-phenyl)-isoxazol-5-yl]-methanol as a white solid.

74.5 Synthesis of carbamic acid 3-(4-benzylamino-phenyl)-isoxazol-5-ylmethyl ester

[3-(4-benzylamino-phenyl)-isoxazol-5-yl]-methanol (178 mg, 0.63 mmol) was dissolved in THF (20 ml, 0.03 M), to which was added CDI (154 mg, 0.95 mmol). After the mixture was stirred at room temperature for about 1 hour, 1 ml of ammonium hydroxide was added and the resulting mixture was stirred for another 3 hours. The completion of the reaction was confirmed by liquid chromatography, and the THF was distilled under reduced pressure to obtain a pale yellow solid compound. The solid compound was extracted three times with water and ethyl acetate, the organic solvent layer was dried under reduced pressure, and then a crude compound was purified by column chromatography on silica gel using ethyl acetate/hexane (1:3) to obtain carbamic acid 3-(4-benzylamino-phenyl)-isoxazol-5-ylmethyl ester as a white solid.

1H-NMR (CDCl3, 200 MHz) δ 7.6 (d, 2H), 7.3 (m, 5H), 6.7 (d, 2H), 6.5 (s, 1H), 5.2 (s, 2H), 4.8 (brs, 2H), 4.3 (s, 2H)

Example 75

Carbamic acid 3-[4-(benzyl-methyl-amino)-phenyl]-isoxazol-5-ylmethyl ester

An experiment was performed using carbamic acid 3-(4-benzylamino-phenyl)-isoxazol-5-ylmethyl ester (150 mg, 0.46 mmol) in Example 74 as a starting material and formaldehyde (20 μl, 0.70 mmol) in the same manner as in Example 74.4 to obtain carbamic acid 3-[4-(benzyl-methyl-amino)-phenyl]-isoxazol-5-ylmethyl ester.

1H-NMR (CDCl3, 200 MHz) δ 7.6 (d, 2H), 7.2 (m, 5H), 6.7 (d, 2H), 6.5 (s, 1H), 5.2 (s, 2H), 5.1 (brs, 2H), 4.6 (s, 2H), 3.1 (s, 3H)

Example 76

Carbamic acid 3-[4-(4-fluoro-benzylamino)-phenyl]-isoxazol-5-ylmethyl ester 76.1 Synthesis of carbamic acid 3-(4-amino-phenyl)-isoxazol-5-ylmethyl ester Carbamic acid 3-(4-amino-phenyl)-isoxazol-5-ylmethyl ester was synthesized in the same manners as in Examples 74.1, 74.2, 74.3, and 74.5 in Example 74.

76.2 Synthesis of carbamic acid 3-[4-(1-phenyl-ethoxy)-phenyl]-isoxazol-5-ylmethyl ester An experiment was performed using the above-obtained carbamic acid 3-(4-amino-phenyl)-isoxazol-5-ylmethyl ester (150 mg, 0.64 mmol) as a starting material and 4-fluorobenzaldehyde (82 μl, 0.77 mmol) in the same manner as in Example 74.4 to obtain carbamic acid 3-[4-(4-fluoro-benzylamino)-phenyl]-isoxazol-5-ylmethyl ester.

1H-NMR (CDCl3, 200 MHz) δ 7.6 (d, 2H), 7.3 (m, 2H), 7.1 (t, 2H), 6.7 (d, 2H), 6.5 (s, 1H), 5.2 (s, 2H), 4.9 (brs, 2H), 4.4 (s, 2H)

Example 77

Carbamic acid 3-[4-(3-fluoro-benzylamino)-phenyl]-isoxazol-5-ylmethyl ester

The compound was synthesized using 3-fluorobenzaldehyde in the same manner as in Example 76.
1H-NMR (CDCl3, 200 MHz) δ 7.6 (d, 2H), 7.3 (m, 2H), 7.1 (m, 2H), 6.7 (d, 2H), 6.6 (s, 1H), 5.2 (s, 2H), 4.9 (brs, 2H), 4.4 (s, 2H)

Example 78

Carbamic acid 3-[4-(2-fluoro-benzylamino)-phenyl]-isoxazol-5-ylmethyl ester

The compound was synthesized using 2-fluorobenzaldehyde in the same manner as in Example 76.
1H-NMR (CDCl3, 200 MHz) δ 7.6 (d, 2H), 7.3 (m, 2H), 7.1 (m, 2H), 6.7 (d, 2H), 6.5 (s, 1H), 5.2 (s, 2H), 4.9 (brs, 2H), 4.4 (s, 2H)

Example 79

Carbamic acid 3-[4-(2,6-difluoro-benzylamino)-phenyl]-isoxazol-5-ylmethyl ester

The compound was synthesized using 2,6-difluorobenzaldehyde in the same manner as in Example 76.
1H-NMR (CDCl3, 200 MHz) δ 7.6 (d, 2H), 7.2 (m, 2H), 6.9 (t, 1H), 6.8 (d, 2H), 6.5 (s, 1H), 5.2 (s, 2H), 4.8 (brs, 2H), 4.5 (s, 2H)

Example 80

Carbamic acid 3-[4-(2,3-difluoro-benzylamino)-phenyl]-isoxazol-5-ylmethyl ester

The compound was synthesized using 2,3-difluorobenzaldehyde in the same manner as in Example 76.
1H-NMR (CDCl3, 200 MHz) δ 7.6 (d, 2H), 7.1 (m, 3H), 6.7 (d, 2H), 6.6 (s, 1H), 5.2 (s, 2H), 4.8 (brs, 2H), 4.5 (s, 2H)

Example 81

Carbamic acid 3-[4-(2,4-difluoro-benzylamino)-phenyl]-isoxazol-5-ylmethyl ester

The compound was synthesized using 2,4-difluorobenzaldehyde in the same manner as in Example 76.
1H-NMR (CDCl3, 200 MHz) δ 7.6 (d, 2H), 7.4 (t, 3H), 6.9 (t, 1H), 6.7 (d, 2H), 6.6 (s, 1H), 5.2 (s, 2H), 4.8 (brs, 2H), 4.4 (s, 2H)

Example 82

Carbamic acid 3-[4-(3,5-difluoro-benzylamino)-phenyl]-isoxazol-5-ylmethyl ester

The compound was synthesized using 3,5-difluorobenzaldehyde in the same manner as in Example 76.

1H-NMR (CDCl3, 200 MHz) δ 7.6 (d, 2H), 6.9 (d, 2H), 6.7 (t, 1H), 6.6 (d, 2H), 6.5 (s, 1H), 5.2 (s, 2H), 4.8 (brs, 2H), 4.4 (s, 2H)

Example 83

Carbamic acid 3-[4-(2,5-difluoro-benzylamino)-phenyl]-isoxazol-5-ylmethyl ester

The compound was synthesized using 2,5-difluorobenzaldehyde in the same manner as in Example 76.
1H-NMR (CDCl3, 200 MHz) δ 7.7 (d, 2H), 7.1 (m, 2H), 7.0 (m, 1H), 6.7 (d, 2H), 6.6 (s, 1H), 5.2 (s, 2H), 4.8 (brs, 2H), 4.5 (s, 2H)

Example 84

Carbamic acid 3-[4-(3,4-difluoro-benzylamino)-phenyl]-isoxazol-5-ylmethyl ester

The compound was synthesized using 3,4-difluorobenzaldehyde in the same manner as in Example 76.
1H-NMR (CDCl3, 200 MHz) δ 7.6 (d, 2H), 7.2 (m, 3H), 6.7 (d, 2H), 6.6 (s, 1H), 5.2 (s, 2H), 4.8 (brs, 2H), 4.4 (s, 2H)

Example 85

Carbamic acid 3-[4-(4-chloro-benzylamino)-phenyl]-isoxazol-5-ylmethyl ester

The compound was synthesized using 4-chlorobenzaldehyde in the same manner as in Example 76.
1H-NMR (CDCl3, 200 MHz) δ 7.6 (d, 2H), 7.3 (d, 4H), 6.6 (d, 2H), 6.5 (s, 1H), 5.2 (s, 2H), 4.8 (brs, 2H), 4.3 (s, 2H)

Example 86

Carbamic acid 3-[4-(2-chloro-benzylamino)-phenyl]-isoxazol-5-ylmethyl ester

The compound was synthesized using 2-chlorobenzaldehyde in the same manner as in Example 76.
1H-NMR (CDCl3, 200 MHz) δ 7.6 (d, 2H), 7.4 (m, 2H), 7.2 (m, 2H), 6.7 (d, 2H), 6.5 (s, 1H), 5.2 (s, 2H), 4.8 (brs, 2H), 4.5 (s, 2H)

Example 87

Carbamic acid 3-[4-(3-chloro-benzylamino)-phenyl]-isoxazol-5-ylmethyl ester

The compound was synthesized using 3-chlorobenzaldehyde in the same manner as in Example 76.
1H-NMR (CDCl3, 200 MHz) δ 7.6 (d, 2H), 7.4 (s, 1H), 7.2 (m, 3H), 6.5 (d, 2H), 6.5 (s, 1H), 5.2 (s, 2H), 4.8 (brs, 2H), 4.4 (s, 2H)

Example 88

Synthesis of carbamic acid 3-[4-(2,3-dichloro-benzylamino)-phenyl]-isoxazol-5-ylmethyl ester The compound was synthesized using 2,3-dichlorobenzaldehyde in the same manner as in Example 76.
1H-NMR (CDCl3, 500 MHz) δ 7.6 (d, 2H), 7.4 (d, 1H), 7.3 (d, 1H), 7.2 (t, 1H), 6.6 (d, 2H), 6.5 (s, 1H), 5.2 (s, 2H), 4.8 (brs, 2H), 4.5 (s, 2H)

Example 89

Synthesis of carbamic acid 3-[4-(2,4-dichloro-benzylamino)-phenyl]-isoxazol-5-ylmethyl ester The compound was synthesized using 2,4-dichlorobenzaldehyde in the same manner as in Example 76.

1H-NMR (CDCl3, 500 MHz) δ 7.6 (d, 2H), 7.4 (d, 1H), 7.3 (s, 1H), 7.2 (t, 1H), 6.6 (d, 2H), 6.5 (s, 1H), 5.2 (s, 2H), 4.8 (brs, 2H), 4.5 (s, 2H)

Example 90

Synthesis of carbamic acid 3-[4-(2,5-dichloro-benzylamino)-phenyl]-isoxazol-5-ylmethyl ester The compound was synthesized using 2,5-dichlorobenzaldehyde in the same manner as in Example 76.

1H-NMR (CDCl3, 500 MHz) δ 7.6 (d, 2H), 7.4 (s, 1H), 7.3 (d, 1H), 7.2 (d, 1H), 6.6 (d, 2H), 6.5 (s, 1H), 5.2 (s, 2H), 4.8 (brs, 2H), 4.4 (s, 2H)

Example 91

Synthesis of carbamic acid 3-[4-(2,6-dichloro-benzylamino)-phenyl]-isoxazol-5-ylmethyl ester The compound was synthesized using 2,6-dichlorobenzaldehyde in the same manner as in Example 76.

1H-NMR (CDCl3, 500 MHz) δ 7.6 (d, 2H), 7.4 (m, 2H), 7.2 (d, 1H), 6.8 (d, 2H), 6.5 (s, 1H), 5.2 (s, 2H), 4.8 (brs, 2H), 4.6 (s, 2H)

Example 92

Synthesis of carbamic acid 3-[4-(3,4-dichloro-benzylamino)-phenyl]-isoxazol-5-ylmethyl ester The compound was synthesized using 3,4-dichlorobenzaldehyde in the same manner as in Example 76.

1H-NMR (CDCl3, 500 MHz) δ 7.6 (d, 2H), 7.45 (s, 1H), 7.4 (d, 1H), 7.2 (d, 1H), 6.6 (d, 2H), 6.5 (s, 1H), 5.2 (s, 2H), 4.8 (brs, 2H), 4.4 (s, 2H)

Example 93

Synthesis of carbamic acid 3-[4-(3,5-dichloro-benzylamino)-phenyl]-isoxazol-5-ylmethyl ester The compound was synthesized using 3,5-dichlorobenzaldehyde in the same manner as in Example 76.

1H-NMR (CDCl3, 500 MHz) δ 7.6 (d, 2H), 7.3 (s, 3H), 6.7 (d, 2H), 6.6 (s, 1H), 5.2 (s, 2H), 4.8 (brs, 2H), 4.4 (s, 2H)

Example 94

Synthesis of carbamic acid 3-[4-(2,3,5-trichloro-benzylamino)-phenyl]-isoxazol-5-ylmethyl ester The compound was synthesized using 2,3,5-trichlorobenzaldehyde in the same manner as in Example 76.

1H-NMR (CDCl3, 500 MHz) δ 7.6 (d, 2H), 7.4 (s, 1H), 7.3 (s, 1H), 6.6 (d, 2H), 6.55 (s, 1H), 5.2 (s, 2H), 4.8 (brs, 2H), 4.5 (s, 2H)

Example 95

Synthesis of carbamic acid 3-[4-(2,3,6-trichloro-benzylamino)-phenyl]-isoxazol-5-ylmethyl ester The compound was synthesized using 2,3,6-trichlorobenzaldehyde in the same manner as in Example 76.

1H-NMR (CDCl3, 500 MHz) δ 7.6 (d, 2H), 7.4 (d, 1H), 7.3 (d, 1H), 6.8 (d, 2H), 6.6 (s, 1H), 5.2 (s, 2H), 4.8 (brs, 2H), 4.7 (s, 2H)

Example 96

Carbamic acid 3-[4-(3-trifluoromethyl-benzylamino)-phenyl]-isoxazol-5-ylmethyl ester The compound was synthesized using 2-(trifluoromethyl)benzaldehyde in the same manner as in Example 76.

1H-NMR (CDCl3, 200 MHz) δ 7.6 (d, 2H), 7.5 (m, 4H), 6.7 (d, 2H), 6.5 (s, 1H), 5.2 (s, 2H), 4.9 (brs, 2H), 4.5 (s, 2H)

Example 97

Carbamic acid 3-[4-(4-trifluoromethyl-benzylamino)-phenyl]-isoxazol-5-ylmethyl ester The compound was synthesized using 4-(trifluoromethyl)benzaldehyde in the same manner as in Example 76.

1H-NMR (CDCl3, 200 MHz) δ 8.0 (d, 4H), 7.8 (d, 2H), 6.9 (d, 2H), 6.6 (s, 1H), 5.2 (s, 2H), 4.7 (brs, 2H), 4.5 (s, 2H)

Example 98

Carbamic acid 3-[4-(3,5-bis-trifluoromethyl-benzylamino)-phenyl]-isoxazol-5-ylmethyl ester The compound was synthesized using 3,5-bis-(trifluoromethyl)benzaldehyde in the same manner as in Example 76.

1H-NMR (CDCl3, 200 MHz) δ 7.8 (m, 3H), 7.7 (d, 2H), 6.7 (d, 2H), 6.6 (s, 1H), 5.2 (s, 2H), 4.8 (brs, 2H), 4.1 (s, 2H)

Example 99

Carbamic acid 3-[4-(2-methyl-benzylamino)-phenyl]-isoxazol-5-ylmethyl ester

The compound was synthesized using 2-methylbenzaldehyde in the same manner as in Example 76.

1H-NMR (CDCl3, 200 MHz) δ 7.6 (d, 2H), 7.2 (m, 4H), 6.9 (d, 2H), 6.5 (s, 1H), 5.2 (s, 2H), 4.8 (brs, 2H), 4.3 (s, 2H), 2.4 (s, 3H)

Example 100

Carbamic acid 3-[4-(4-methyl-benzylamino)-phenyl]-isoxazol-5-ylmethyl ester

The compound was synthesized using 4-methylbenzaldehyde in the same manner as in Example 76.

1H-NMR (CDCl3, 200 MHz) δ 7.6 (d, 2H), 7.2 (m, 4H), 6.7 (d, 2H), 6.5 (s, 1H), 5.2 (s, 2H), 4.8 (brs, 2H), 4.3 (s, 2H), 2.3 (s, 3H)

Example 101

Carbamic acid 3-[4-(3-methyl-benzylamino)-phenyl]-isoxazol-5-ylmethyl ester

The compound was synthesized using 3-methylbenzaldehyde in the same manner as in Example 76.
1H-NMR (CDCl3, 200 MHz) δ 7.6 (d, 2H), 7.2 (m, 4H), 6.7 (d, 2H), 6.5 (s, 1H), 5.2 (s, 2H), 4.9 (brs, 2H), 4.4 (s, 2H), 2.4 (s, 3H)

Example 102

Carbamic acid 3-[4-(4-isopropyl-benzylamino)-phenyl]-isoxazol-5-ylmethyl ester

The compound was synthesized using 4-isopropylbenzaldehyde in the same manner as in Example 76.
1H-NMR (CDCl3, 200 MHz) δ 7.6 (d, 2H), 7.2 (m, 4H), 6.7 (d, 2H), 6.5 (s, 1H), 5.2 (s, 2H), 4.7 (brs, 2H), 4.3 (s, 2H), 1.5 (brs, 1H), 1.2 (s, 6H)

Example 103

Carbamic acid 3-[4-(2,4-dimethyl-benzylamino)-phenyl]-isoxazol-5-ylmethyl ester

The compound was synthesized using 2,4-dimethylbenzaldehyde in the same manner as in Example 76.
1H-NMR (CDCl3, 200 MHz) δ 7.6 (d, 2H), 7.1 (m, 3H), 6.7 (d, 2H), 6.5 (s, 1H), 5.2 (s, 2H), 5.0 (brs, 2H), 4.3 (s, 2H), 2.4 (s, 6H)

Example 104

Carbamic acid 3-[4-(2-methoxy-benzylamino)-phenyl]-isoxazol-5-ylmethyl ester

The compound was synthesized using 2-methoxybenzaldehyde in the same manner as in Example 76.
1H-NMR (CDCl3, 200 MHz) δ 7.8 (d, 2H), 7.6 (t, 2H), 7.0 (m, 2H), 6.7 (d, 2H), 6.5 (s, 1H), 5.2 (s, 2H), 4.7 (brs, 2H), 4.4 (s, 2H), 3.9 (s, 3H)

Example 105

Carbamic acid 3-[4-(3-methoxy-benzylamino)-phenyl]-isoxazol-5-ylmethyl ester

The compound was synthesized using 3-methoxybenzaldehyde in the same manner as in Example 76.
1H-NMR (CDCl3, 200 MHz) δ 7.6 (d, 2H), 7.5 (d, 1H), 7.3 (m, 2H), 6.9 (d, 1H), 6.7 (d, 2H), 6.5 (s, 1H), 5.2 (s, 2H), 4.8 (brs, 2H), 4.4 (s, 2H), 3.9 (s, 3H)

Example 106

Carbamic acid 3-[4-(4-methoxy-benzylamino)-phenyl]-isoxazol-5-ylmethyl ester

The compound was synthesized using 4-methoxybenzaldehyde in the same manner as in Example 76.
1H-NMR (CDCl3, 200 MHz) δ 7.6 (d, 2H), 7.3 (m, 2H), 6.9 (m, 4H), 6.5 (d, 1H), 5.2 (s, 2H), 4.8 (brs, 2H), 4.3 (s, 2H), 4.0 (s, 3H)

Example 107

Synthesis of carbamic acid 3-[4-(4-phenoxy-benzylamino)-phenyl]-isoxazol-5-ylmethyl ester The compound was synthesized using 4-phenoxybenzaldehyde in the same manner as in Example 76.
1H-NMR (CDCl3, 200 MHz) δ 7.6 (d, 2H), 7.3 (dd, 4H), 7.1 (m, 5H), 6.7 (d, 2H), 6.5 (s, 1H), 5.2 (s, 2H), 4.8 (brs, 2H), 4.4 (s, 2H)

Example 108

Synthesis of carbamic acid 3-[4-(4-benzyloxy-benzylamino)-phenyl]-isoxazol-5-ylmethyl ester The compound was synthesized using 4-benzyloxybenzaldehyde in the same manner as in Example 76.
1H-NMR (CDCl3, 200 MHz) δ 7.6 (d, 2H), 7.4-7.2 (m, 7H), 6.9 (d, 2H), 6.7 (d, 2H), 6.5 (s, 1H), 5.2 (s, 2H), 5.1 (s, 2H), 4.8 (brs, 2H), 4.3 (s, 2H)

Example 109

Synthesis of carbamic acid 3-{4-[(5-phenyl-isoxazol-3-ylmethyl)-amino]-phenyl}-isoxazol-5-ylmethyl ester The compound was synthesized using 5-phenyl-isoxazol-3-carbaldehyde in the same manner as in Example 76.
1H-NMR (CDCl3, 500 MHz) δ 7.8 (d, 2H), 7.7 (d, 1H), 7.5 (m, 3H), 6.8 (d, 2H), 6.75 (d, 1H), 6.55 (s, 1H), 6.5 (s, 1H), 5.2 (s, 2H), 54.8 (brs, 2H), 4.5 (s, 2H)

Example 110

Synthesis of carbamic acid 3-{4-[(thiophen-2-ylmethyl)-amino]-phenyl}-isoxazol-5-ylmethyl ester The compound was synthesized using thiophene-3-carbaldehyde in the same manner as in Example 76.
1H-NMR (CDCl3, 500 MHz) δ 7.6 (d, 2H), 7.25 (d, 1H), 7.05 (s, 1H), 7.0 (d, 1H), 6.7 (d, 2H), 6.55 (s, 1H), 5.2 (s, 2H), 4.8 (brs, 2H), 4.6 (s, 2H)

Example 111

Synthesis of carbamic acid 3-{4-[(furan-3-ylmethyl)-amino]-phenyl}-isoxazol-5-ylmethyl ester The compound was synthesized using 3-furaldehyde in the same manner as in Example 76.
1H-NMR (CDCl3, 500 MHz) δ 7.6 (d, 2H), 7.4 (d, 2H), 6.7 (d, 2H), 6.5 (s, 1H), 6.4 (s, 1H), 5.2 (s, 2H), 4.8 (brs, 2H), 4.2 (s, 2H)

Example 112

Synthesis of carbamic acid 3-{4-[(3,5-dimethyl-isoxazol-4-ylmethyl)-amino]-phenyl}-isoxazol-5-ylmethyl ester The compound was synthesized using 3,5-dimethyl-isoxazolecarbaldehyde in the same manner as in Example 76.
1H-NMR (CDCl3, 200 MHz) δ 7.6 (d, 2H), 6.7 (d, 2H), 6.5 (s, 1H), 5.2 (s, 2H), 4.8 (brs, 2H), 4.5 (s, 2H), 2.4 (s, 3H), 2.2 (s, 3H)

Example 113

Synthesis of carbamic acid 3-[4-(3,5-di-tert-butyl-4-hydroxy-benzylamino)-phenyl]-isoxazol-5-ylmethyl ester The compound was synthesized using 3,5-di-t-butyl-4-hydroxybenzaldehyde in the same manner as in Example 76.
1H-NMR (CDCl3, 500 MHz) δ 7.6 (d, 2H), 7.2 (s, 2H), 6.7 (d, 2H), 6.57 (s, 1H), 5.2 (s, 2H), 4.8 (brs, 2H), 4.2 (s, 2H), 1.45 (s, 18H)

Example 114

Synthesis of carbamic acid 3-[4-(3,5-dimethyl-4-hydroxy-benzylamino)-phenyl]-isoxazol-5-ylmethyl ester The compound was synthesized using 3,5-di-methyl-4-hydroxybenzaldehyde in the same manner as in Example 76.
1H-NMR (CDCl3, 200 MHz) δ 7.6 (d, 2H), 7.0 (s, 2H), 6.7 (d, 2H), 6.57 (s, 1H), 5.2 (s, 2H), 4.8 (brs, 2H), 4.2 (s, 2H), 2.2 (s, 6H)

Example 115

Synthesis of carbamic acid 3-[4-(3,5-di-tert-butyl-benzylamino)-phenyl]-isoxazol-5-ylmethyl ester The compound was synthesized using 3,5-di-t-butyl-benzaldehyde in the same manner as in Example 76.
1H-NMR (CDCl3, 500 MHz) δ 7.6 (d, 2H), 7.4 (s, 1H), 7.2 (s, 2H), 6.7 (d, 2H), 6.57 (s, 1H), 5.2 (s, 2H), 4.8 (brs, 2H), 4.3 (s, 2H), 1.3 (s, 18H)

Example 116

Synthesis of carbamic acid 3-[4-(3,4,5-trihydroxy-benzylamino)-phenyl]-isoxazol-5-ylmethyl ester

[3-(4-amino-phenyl)-isoxazol-5-yl]-methanol was reacted with 3,4,5-trihydroxybenzaldehyde in a MeOH solvent to form an imine, and then Si—BH3CN was added to the reaction solution and stirred at room temperature for 48 hours. A solution obtained by filtration of the reactant was distilled off under reduced pressure and column chromatography was used to obtain carbamic acid 3-[4-(3,4,5-trihydroxy-benzylamino)-phenyl]-isoxazol-5-ylmethyl ester as a desired compound.
1H-NMR (CD3OD, 200 MHz) δ 7.5 (d, 2H), 6.65 (s, 1H), 6.6 (d, 2H), 6.4 (s, 2H), 5.2 (s, 2H), 4.2 (s, 2H)

Example 117

Synthesis of carbamic acid 1-[3-(4-benzyloxy-phenyl)-isoxazol-5-yl]-ethyl ester

The compound was synthesized using 3-butyn-2-ol instead of propargyl alcohol in the same manner as in Example 1.
1H-NMR (CD3OD, 200 MHz) δ 7.6 (d, 2H), 7.3 (m, 5H), 7.0 (d, 2H), 6.4 (s, 1H), 5.8 (q, 1H), 5.0 (s, 2H), 1.5 (d, 3H)

Example 118

Synthesis of carbamic acid 2-[3-(4-benzyloxy-phenyl)-isoxazol-5-yl]-ethyl ester

The compound was synthesized using 3-butyn-1-ol instead of propargyl alcohol in the same manner as in Example 1.
1H-NMR (CDCl3, 200 MHz) δ 7.7 (d, 2H), 7.4 (m, 5H), 7.1 (d, 2H), 6.35 (s, 1H), 5.1 (s, 2H), 4.6 (brs, 2H), 4.4 (t, 2H), 3.1 (t, 2H)

Example 119

[3-(4-benzyloxy-phenyl)-isoxazol-5-ylmethyl]-prop-2-ynyl-amine

119.1 Synthesis of 3-(4-benzyloxy-phenyl)-isoxazol-5-carbaldehyde

[3-(4-benzyloxy-phenyl)-isoxazol-5-yl]-methanol (1.0 g, 3.5 mmol) was dissolved in 60 ml of DMSO/methylene chloride (1:2), to which solution were added dropwise sulfur trioxide.pyridine complex (1.6 g, 10.5 mmol) and triethylamine (2.44 ml, 17.5 mmol), and stirred at 0° C. for about 2 hours. The completion of the reaction was confirmed by TLC, and 10 ml of NH4Cl was added to the solution. The residual solvent was distilled under reduced pressure, and then extracted three times with water and methylene chloride. An organic layer was washed with saline solution. The obtained organic layer was distilled under reduced pressure, followed by column chromatography (ethyl acetate/Hexane=1:2) to obtain 3-(4-benzyloxy-phenyl)-isoxazol-5-carbaldehyde as a desired solid compound.

119.2 Synthesis of [3-(4-benzyloxy-phenyl)-isoxazol-5-ylmethyl]-prop-2-ynyl-amine 3-(4-benzyloxy-phenyl)-isoxazol-5-carbaldehyde (150 mg, 0.53 mmol) and propargyl amine (51 µl, 0.8 mmol) were dissolved in MeOH and stirred at room temperature for about 2 hours. The production of an imine was confirmed by TLC, NaBH3CN (50 mg, 0.8 mmol) was placed to the mixture at 0° C., the temperature was increased to room temperature, and the mixture was stirred for 12 hours. The MeOH was distilled off under reduced pressure and 10 ml of a NaHCO3 aqueous solution was added to the mixture, followed by extraction three times with water and ethyl acetate. The obtained organic layer was distilled under reduced pressure, followed by column chromatography to obtain 3-(4-benzyloxy-phenyl)-isoxazol-5-ylmethyl]-prop-2-ynyl-amine as a desired solid compound.
1H-NMR (CDCl3, 200 MHz) δ 7.7 (d, 2H), 7.4 (m, 5H), 7.1 (d, 2H), 6.5 (s, 1H), 5.1 (s, 2H), 4.1 (s, 2H), 3.5 (s, 2H), 2.3 (m, 1H)

Example 120

Imidazole-1-carboxylic acid 3-(4-benzyloxy-phenyl)-isoxazol-5-ylmethyl ester

120.1 Synthesis of 3-(4-benzyloxy-phenyl)-isoxazol-5-yl]-methanol

[3-(4-benzyloxy-phenyl)-isoxazol-5-yl]-methanol was synthesized in the same manners as in Examples 1.1 and 1.2.

120.2 Imidazole-1-carboxylic acid 3-(4-benzyloxy-phenyl)-isoxazol-5-ylmethyl ester

[3-(4-benzyloxy-phenyl)-isoxazol-5-yl]-methanol (500 mg, 1.77 mmol) was dissolved in 10 ml of THF, to which solution was added 1,1'-carbonyldiimidazole (576 mg, 3.55 mmol), and stirred at room temperature for 1 hour. The THF was distilled off under reduced pressure and extracted three times with water and ethyl acetate. An obtained organic layer was distilled under reduced pressure and recrystallized from hexane/ethyl acetate (1/4) conditions to obtain imidazole-1-carboxylic acid 3-(4-benzyloxy-phenyl)-isoxazol-5-ylmethyl ester as a desired solid compound.

1H-NMR (CDCl3, 200 MHz) δ 8.3 (brs, 1H), 7.7 (d, 2H), 7.5 (m, 6H), 7.1 (d, 3H), 6.7 (s, 1H), 5.6 (s, 2H), 5.1 (s, 2H)

Example 121

Synthesis of methyl-carbamic acid 3-(4-benzyloxy-phenyl)-isoxazol-5-ylmethyl ester 0.5 g of the compound [3-(4-benzyloxy-phenyl)-isoxazol-5-yl]-methanol in Example 1 was dissolved in 10 ml of THF, to which solution was added 0.49 g (1.7 equivalents) of 1,1'-carbonyldiimidazole. The consumption of all the reactants was confirmed by TLC, and 2 equivalents of methyl amine were added to the reaction solution. 2 hours later, the solvent was distilled off under reduced pressure, 50 ml of a 1N—HCl aqueous solution was placed in the reactants, and the mixture was extracted three times with 30 ml of ethyl acetate. An obtained organic layer was distilled under reduced pressure, followed by column chromatography to obtain methyl-carbamic acid 3-(4-benzyloxy-phenyl)-isoxazol-5-ylmethyl ester as a desired compound.

1H-NMR (CDCl3, 200 MHz) δ 7.7 (d, 2H), 7.4 (m, 5H), 7.0 (d, 2H), 6.6 (s, 1H), 5.2 (s, 2H), 5.1 (s, 2H), 4.8 (brs, 1H), 2.8 (d, 3H)

Example 122

Synthesis of dimethyl-carbamic acid 3-(4-benzyloxy-phenyl)-isoxazol-5-ylmethyl ester The compound was synthesized using diethyl amine in the same manner as in Example 121.

1H-NMR (CDCl3, 200 MHz) δ 7.7 (d, 2H), 7.4 (m, 5H), 7.0 (d, 2H), 6.6 (s, 1H), 5.2 (s, 2H), 5.1 (s, 2H), 3.0 (s, 6H)

Example 123

Synthesis of diethyl-carbamic acid 3-(4-benzyloxy-phenyl)-isoxazol-5-ylmethyl ester The compound was synthesized using diethyl amine in the same manner as in Example 121.

1H-NMR (CDCl3, 200 MHz) δ 7.7 (d, 2H), 7.4 (m, 5H), 7.0 (d, 2H), 6.6 (s, 1H), 5.2 (s, 2H), 5.1 (s, 2H), 3.3 (q, 4H), 1.2 (t, 6H)

Example 124

Synthesis of ethyl-methyl-carbamic acid 3-(4-benzyloxy-phenyl)-isoxazol-5-ylmethyl ester The compound was synthesized using N-ethylmethylamine amine in the same manner as in Example 121.

1H-NMR (CDCl3, 200 MHz) δ 7.7 (d, 2H), 7.4 (m, 5H), 7.0 (d, 2H), 6.6 (s, 1H), 5.2 (s, 2H), 5.1 (s, 2H), 3.3 (q, 2H), 2.9 (s, 3H), 1.15 (t, 3H)

Example 125

Synthesis of pyrrolidine-1-carboxylic acid 3-(4-benzyloxy-phenyl)-isoxazol-5-ylmethyl ester The compound was synthesized using pyrrolidine in the same manner as in Example 121.

1H-NMR (CDCl3, 200 MHz) δ 7.7 (d, 2H), 7.4 (m, 5H), 7.0 (d, 2H), 6.6 (s, 1H), 5.2 (s, 2H), 5.1 (s, 2H), 3.4 (m, 4H), 1.9 (m, 2H), 1.6 (m, 2H)

Example 126

Synthesis of piperidine-1-carboxylic acid 3-(4-benzyloxy-phenyl)-isoxazol-5-ylmethyl ester The compound was synthesized using piperidine in the same manner as in Example 121.

1H-NMR (CDCl3, 200 MHz) δ 7.7 (d, 2H), 7.4 (m, 5H), 7.0 (d, 2H), 6.6 (s, 1H), 5.2 (s, 2H), 5.1 (s, 2H), 3.5 (m, 4H), 1.6 (m, 6H)

Example 127

Synthesis of morpholine-4-carboxylic acid 3-(4-benzyloxy-phenyl)-isoxazol-5-ylmethyl ester The compound was synthesized using morpholine in the same manner as in Example 121.

1H-NMR (CDCl3, 200 MHz) δ 7.7 (d, 2H), 7.4 (m, 5H), 7.0 (d, 2H), 6.6 (s, 1H), 5.2 (s, 2H), 5.1 (s, 2H), 3.7 (m, 2H), 3.5 (m, 4H), 1.6 (m, 2H)

Example 128

Piperazine-1-carboxylic acid 3-(4-benzyloxy-phenyl)-isoxazol-5-ylmethyl ester

N-boc-piperazin-1-carboxylic acid 3-(4-benzyloxy-phenyl)-isoxazol-5-ylmethyl ester was obtained using N-boc piperazine in the same manner as in Example 121. The compound was dissolved in methylene chloride (5 ml), to which solution was added 5 ml of 0.2 N HCl (in ether), and stirred for 3 hours or more. The thus-obtained white solid compound was filtered to obtain piperazine-1-carboxylic acid 3-(4-benzyloxy-phenyl)-isoxazol-5-ylmethyl ester hydrochloride.

1H-NMR (CDCl3, 200 MHz) δ 7.7 (d, 2H), 7.4 (m, 4H), 7.0 (d, 2H), 6.6 (d, 1H), 5.3 (s, 2H), 5.1 (s, 2H), 3.9 (brs, 4H), 3.2 (brs, 4H)—NMR solvent confirmation Example 129

Synthesis of N',N'-dimethyl-hydrazinecarboxylic acid 3-(4-benzyloxy-phenyl)-isoxazol-5-ylmethyl ester The compound was synthesized using 1,1'-dimethylhydrazine in the same manner as in Example 121.

1H-NMR (CDCl3, 200 MHz) δ 7.8 (d, 2H), 7.4 (m, 5H), 7.0 (d, 2H), 6.6 (s, 1H), 5.2 (s, 2H), 5.1 (s, 2H), 3.0 (s, 6H)

Example 130

(3-amino-propyl)-carbamic acid 3-(4-benzyloxy-phenyl)-isoxazol-5-ylmethyl ester

{3-[3-(4-benzyloxy-phenyl)-isoxazol-5-ylmethoxycarbonylamino]-propyl}-carbamic acid tert-butyl ester was synthesized using t-butyl N-(3-aminopropyl)carbamate in the same manner as in Example 121, and then a boc-deprotection of the compound was performed to synthesize (3-amino-propyl)-carbamic acid 3-(4-benzyloxy-phenyl)-isoxazol-5-ylmethyl ester as a desired compound.

1H-NMR (CDCl3, 200 MHz) δ 7.8 (m, 2H), 7.4 (m, 5H), 7.1 (d, 2H), 6.6 (s, 1H), 5.2 (s, 2H), 5.1 (s, 2H), 3.2 (m, 4H), 1.7 (m, 2H)

Example 131

(2-amino-ethyl)-carbamic acid 3-(4-benzyloxy-phenyl)-isoxazol-5-ylmethyl ester

The compound was synthesized using t-butyl N-(2-amino-ethyl)carbamate in the same manner as in Example 130.
1H-NMR (CDCl3, 200 MHz) δ 7.7 (d, 2H), 7.4 (m, 5H), 7.0 (d, 2H), 6.6 (s, 1H), 5.7 (brs, 1H), 5.2 (s, 2H), 5.1 (s, 2H), 3.3 (brs, 4H)

Example 132

Synthesis of piperidine-1-yl-carbamic acid 3-(4-benzyloxy-phenyl)-isoxazol-5-ylmethyl ester The compound was synthesized using 1-aminopiperidine in the same manner as in Example 121.
1H-NMR (CDCl3, 200 MHz) δ 7.8 (d, 2H), 7.4 (m, 5H), 7.0 (d, 2H), 6.6 (s, 1H), 5.2 (s, 2H), 5.1 (s, 2H), 3.5 (m, 4H), 1.6 (m, 6H)

Example 133

Synthesis of (4-methyl-piperazin-1-yl)-carbamic acid 3-(4-benzyloxy-phenyl)-isoxazol-5-ylmethyl ester The compound was synthesized using 1-amino 4-methylpiperazine in the same manner as in Example 121.
1H-NMR (CDCl3, 200 MHz) δ 7.8 (d, 2H), 7.4 (m, 5H), 7.1 (d, 2H), 6.6 (s, 1H), 5.3 (s, 2H), 5.1 (s, 2H), 3.6 (m, 4H), 2.5 (m, 4H), 2.4 (s, 3H)

Example 134

4-methyl-piperazin-1-carboxylic acid 3-(4-benzyloxy-phenyl)-isoxazol-5-ylmethyl ester An experiment was performed using 1-methylpiperazine in the same manner as in Example 121.
1H-NMR (CDCl3, 200 MHz) δ 7.7 (d, 2H), 7.4 (m, 5H), 7.0 (d, 2H), 6.6 (s, 1H), 5.3 (brs, 2H), 5.2 (s, 2H), 4.2 (brs, 2H), 3.8 (brs, 2H), 3.4 (brs, 2H), 2.8 (s, 3H)

Example 135

Piperidine-4-yl-carbamic acid 3-(4-benzyloxy-phenyl)-isoxazol-5-ylmethyl ester

An experiment was performed using 4-amino-1-boc-piperidine in the same manner as in Example 130.
1H-NMR (CDCl3, 200 MHz) δ 7.7 (d, 2H), 7.3 (m, 5H), 7.0 (d, 2H), 6.5 (s, 1H), 5.1 (s, 2H), 5.0 (s, 2H), 3.6 (brs, 2H), 2.9 (brs, 2H), 2.1 (brs, 2H), 1.8 (brs, 2H)

Example 136

4-[3-(4-benzyloxy-phenyl)-isoxazol-5-ylmethoxycarbonyl]-[1,4]diazepan-1-ium chloride An experiment was performed using 1-boc-homopiperazine in the same manner as in Example 130.

1H-NMR (CDCl3, 200 MHz) δ 7.7 (d, 2H), 7.4 (m, 5H), 7.0 (d, 2H), 6.5 (s, 1H), 5.2 (s, 2H), 5.1 (s, 2H), 4.4 (s, 2H), 3.6 (m, 4H), 2.9 (m, 4H), 1.8 (m, 2H)

Example 137

1-[3-(4-benzyloxy-phenyl)-isoxazol-5-ylmethyl]-piperidin-4-ol

137.1 Synthesis of methanesulfonic acid 3-(4-benzyloxy-phenyl)-isoxazol-5-ylmethyl ester

[3-(4-benzyloxy-phenyl)-isoxazol-5-yl]-methanol (3.0 g, 10.6 mmol) was dissolved in methylene chloride (50 ml, 0.2 M), to which solution were added dropwise MsCl (1.23 ml, 15.9 mmol) and triethylamine (2.23 ml, 16 mmol-), and a reaction was performed at room temperature for 4 hours. The completion of the reaction was confirmed by liquid chromatography, 5 ml of water was added to the mixture, and the resulting solution was extracted with water and methylene chloride. The organic solvent layer was distilled under reduced pressure to obtain a crude solid compound. This was recrystallized from hexane:ethyl acetate (5:1) to obtain methanesulfonic acid 3-(4-benzyloxy-phenyl)-isoxazol-5-ylmethyl ester as a white solid compound.

137.2 Synthesis of 1-[3-(4-benzyloxy-phenyl)-isoxazol-5-ylmethyl]-piperidin-4-ol Methanesulfonic acid-3-(4-benzyloxy-phenyl)-isoxazol-5-ylmethyl ester (150 mg, 0.42 mmol), 4-hydroxypiperidine (64 mg, 0.63 mmol), potassium carbonate (87 mg, 0.63 mmol), and TBAI (96 mg, 0.26 mmol) were placed in 10 ml of DMF and stirred at room temperature overnight. The completion of the reaction was confirmed by LC, and then a crude solid compound obtained from distillation of the DMF under reduced pressure was extracted with ethyl acetate and water. The ethyl acetate was distilled off under reduced pressure to obtain a white solid compound. The compound was recrystallized from methylene chloride:MeOH (9:1) to obtain 1-[3-(4-benzyloxy-phenyl)-isoxazol-5-ylmethyl]-piperidin-4-ol as a white solid compound.
1H-NMR (CDCl3, 200 MHz) δ 7.65 (d, 2H), 7.35 (m, 5H), 6.94 (d, 2H), 6.53 (d, 2H), 5.38 (s, 1H), 5.19 (s, 2H), 4.84 (brs, 2H), 1.67 (s, 3H)

Example 138

Carbamic acid 1-[3-(4-benzyloxy-phenyl)-isoxazol-5-ylmethyl]-piperidin-4-yl ester An experiment was performed using the compound in Example 137 as a starting material in the same manner as in Example 74.5.
1H-NMR (CDCl3, 200 MHz) δ 7.7 (d, 2H), 7.4 (m, 5H), 7.0 (d, 2H), 6.5 (s, 1H), 5.1 (s, 2H), 4.6 (brs, 2H), 3.8 (s, 2H), 2.8 (brs, 2H), 2.4 (brs, 2H), 2.0 (brs, 2H), 1.8 (brs, 2H)

Example 139

3-(4-benzyloxy-phenyl)-5-imidazol-1-ylmethyl-isoxazole

139.1 Synthesis of methanesulfonic acid 3-(4-benzyloxy-phenyl)-isoxazol-5-ylmethyl ester Methanesulfonic acid 3-(4-benzyloxy-phenyl)-isoxazol-5-ylmethyl ester was synthesized in the same manner as in Example 137.1.

139.2 Synthesis of 3-(4-benzyloxy-phenyl)-5-imidazol-1-ylmethyl-isoxazole

Methanesulfonic acid-3-(4-benzyloxy-phenyl)-isoxazol-5-ylmethyl ester (600 mg, 1.67 mmol), imidazole (170 mg, 2.50 mmol), potassium carbonate (460 mg, 3.34 mmol), and TBAI (200 mg, 0.54 mmol) were placed in 20 ml of DMF and stirred for 2 hours. The completion of the reaction was confirmed by LC, and then a crude solid compound obtained from distillation of the DMF under reduced pressure was extracted with ethyl acetate and water. The ethyl acetate was distilled off under reduced pressure to obtain a white solid compound. The compound was purified by silica chromatography (methylene chloride:MeOH=20:1) to obtain 3-(4-benzyloxy-phenyl)-5-imidazol-1-ylmethyl-isoxazole as a white solid compound.

1H-NMR (DMSO, 200 MHz) δ 9.36 (s, 1H), 7.82 (m, 4H), 7.40 (m, 5H), 7.12 (t, 3H), 5.80 (s, 2H), 5.17 (s, 2H)

Example 140

3-(4-benzyloxy-phenyl)-5-(2-methyl-imidazol-1-ylmethyl)-isoxazole

An experiment was performed using 2-methylimidazole in the same manner as in Example 139.

1H-NMR (CDCl3, 200 MHz) δ 7.67 (d, 2H), 7.38 (m, 5H), 7.01 (m, 4H), 6.26 (s, 1H), 5.16 (s, 2H), 5.08 (s, 2H), 2.45 (s, 3H)

Example 141

3-(4-benzyloxy-phenyl)-5-(4-methyl-imidazol-1-ylmethyl)-isoxazole

An experiment was performed using 4-methylimidazole in the same manner as in Example 139.

1H-NMR (DMSO, 200 MHz) δ 9.25 (s, 1H), 7.80 (d, 2H), 7.56 (m, 6H), 7.12 (t, 3H), 5.75 (s, 2H), 5.17 (s, 2H), 2.28 (s, 3H)

Example 142

3-[4-(3-fluoro-benzyloxy)-phenyl]-5-imidazol-1-ylmethyl-isoxazole

142.1 Synthesis of 4-(5-imidazol-1-ylmethyl-isoxazol-3-yl)-phenol 3-(4-benzyloxy-phenyl)-5-imidazol-1-ylmethyl-isoxazol was obtained in the same manners as in Examples 139-1 and 139-2 in Example 139. The compound was dissolved in MeOH, and a hydrogenation of the resulting solution was performed using 10 wt % Pd/C to synthesize 4-(5-imidazol-1-ylmethyl-isoxazol-3-yl)-phenol as a debenzyl compound.

142.2 Synthesis of 3-[4-(3-fluoro-benzyloxy)-phenyl]-5-imidazol-1-ylmethyl-isoxazole 4-(5-imidazol-1-ylmethyl-isoxazol-3-yl)-phenol (150 mg, 0.62 mmol) and potassium carbonate (172 mg, 1.25 mmol) were placed in 10 ml of DMF, to which solution was added dropwise 3-fluorobenzyl bromide (89 μl, 0.75 mmol), and the mixture was stirred at room temperature for 4 hours. The completion of the reaction was confirmed by LC, and then DMF was distilled off under reduced pressure. A crude solid compound was extracted with ethyl acetate and water, and the organic solvent was distilled off under reduced pressure to obtain a white solid compound. The compound was purified by silica chromatography (methylene chloride:MeOH=20:1) to obtain 3-[4-(3-fluoro-benzyloxy)-phenyl]-5-imidazol-1-ylmethyl-isoxazole as a desired white solid compound.

1H-NMR (DMSO, 200 MHz) δ 9.37 (s, 1H), 7.85 (m, 4H), 7.33 (m, 7H), 5.80 (s, 2H), 5.21 (s, 2H)

Example 143

3-[4-(2,6-difluoro-benzyloxy)-phenyl]-5-imidazol-1-ylmethyl-isoxazole

An experiment was performed using 2,6-difluorobenzyl bromide in the same manner as in Example 142.

1H-NMR (DMSO, 200 MHz) δ 9.32 (s, 1H), 7.85 (q, 4H), 7.56 (m, 1H), 7.20 (m, 5H), 5.79 (s, 2H), 5.19 (s, 2H)

Example 144

1-[3-(4-benzyloxy-phenyl)-isoxazol-5-ylmethyl]-1H-[1,2,4]triazole

An experiment was performed using 1,2,4-triazole in the same manner as in Example 139.

1H-NMR (CDCl3, 200 MHz) δ 8.26 (s, 1H), 8.02 (s, 1H), 7.68 (d, 2H), 7.36 (m, 5H), 7.02 (d, 2H), 6.50 (s, 1H), 5.50 (s, 2H), 5.09 (s, 2H)

Example 145

1-[3-(4-benzyloxy-phenyl)-isoxazol-5-ylmethyl]-1H-[1,2,3]triazole

An experiment was performed using 1,2,3-triazole in the same manner as in Example 139.

1H-NMR (CDCl3, 200 MHz) δ 7.78 (q, 4H), 7.40 (m, 5H), 7.03 (d, 2H), 6.51 (s, 1H), 5.75 (s, 2H), 5.11 (s, 2H)

Example 146

2-[3-(4-benzyloxy-phenyl)-isoxazol-5-ylmethyl]-2H-tetrazole

A separation of the upper spot in the two compounds obtained by reaction using tetrazole in the same manner as in Example 139 was performed by column chromatography to obtain 2-[3-(4-benzyloxy-phenyl)-isoxazol-5-ylmethyl]-2H-tetrazole as a desired compound.

1H-NMR (CDCl3, 200 MHz) δ 8.6 (s, 1H), 7.7 (d, 2H), 7.5 (m, 5H), 7.1 (d, 2H), 6.6 (s, 1H), 6.0 (s, 2H), 5.2 (s, 2H), 5.11 (s, 2H)

Example 147

1-[3-(4-benzyloxy-phenyl)-isoxazol-5-ylmethyl]-2H-tetrazole

The lower compound in Example 146 was separated by column chromatography to obtain 1-[3-(4-benzyloxy-phenyl)-isoxazol-5-ylmethyl]-2H-tetrazole as a desired compound.

1H-NMR (CDCl3, 200 MHz) δ 8.6 (s, 1H), 7.7 (d, 2H), 6.6 (s, 1H), 5.8 (s, 2H), 5.1 (s, 2H), 5.11 (s, 2H)

Example 148

3-(4-benzyloxy-phenyl)-5-pyrrolidin-1-ylmethyl-isoxazole

An experiment was performed using pyrrolidine in the same manner as in Example 139.
1H-NMR (CDCl3, 200 MHz) δ 7.76 (d, 2H), 7.39 (m, 5H), 7.02 (d, 2H), 6.45 (s, 1H), 5.10 (s, 2H), 3.82 (s, 2H), 2.64 (s, 4H), 1.82 (s, 4H)

Example 149

1-[3-(4-benzyloxy-phenyl)-isoxazol-5-ylmethyl]-piperidine

An experiment was performed using piperidine in the same manner as in Example 139.
1H-NMR (CDCl3, 200 MHz) δ 7.7 (d, 2H), 7.4 (m, 5H), 7.0 (d, 2H), 6.4 (s, 1H), 5.3 (s, 2H), 5.1 (s, 2H), 4.6 (s, 2H), 2.5 (d, 4H), 1.6 (d, 4H)

Example 150

[3-(4-benzyloxy-phenyl)-isoxazol-5-ylmethyl]-dimethyl-amine

An experiment was performed using dimethylamine in the same manner as in Example 139.
1H-NMR (CDCl3, 200 MHz) δ 7.76 (d, 2H), 7.42 (m, 5H), 7.02 (d, 2H), 6.45 (s, 1H), 5.11 (s, 2H), 3.66 (s, 2H), 2.34 (s, 6H)

Example 151

[3-(4-benzyloxy-phenyl)-isoxazol-5-ylmethyl]-diethyl-amine

An experiment was performed using diethylamine in the same manner as in Example 139.
1H-NMR (CDCl3, 200 MHz) δ 7.79 (d, 2H), 7.43 (m, 5H), 7.05 (d, 2H), 6.46 (s, 1H), 5.12 (s, 2H), 3.87 (s, 2H), 2.63 (q, 4H), 1.45 (t, 6H)

Example 152

Synthesis of [3-(4-benzyloxy-phenyl)-isoxazol-5-ylmethyl]-urea

152.1
3-(4-benzyloxy-phenyl)-5-chloromethyl-isoxazole 0.3 g of [3-(4-benzyloxy-phenyl)-isoxazol-5-yl]-methanol in Example 1 was dissolved in 10 ml of benzene, to which solution was added 0.15 ml (2 equivalents) of SOCl2, and the mixture was refluxed for 4 hours.
3-(4-benzyloxy-phenyl)-5-chloromethyl-isoxazole obtained after drying and removal of the solvent under reduced pressure was used in the next reaction without further purification.

152.2 C-[3-(4-benzyloxy-phenyl)-isoxazol-5-yl]-methylamine 0.13 g of 3-(4-benzyloxy-phenyl)-5-chloromethyl-isoxazole was dissolved in 10 ml of DMF, to which solution was added 85 mg (3 equivalents) of NaN3, and the mixture was stirred for 12 hours. The solvent was dried off under reduced pressure and removed, followed by column chromatography to obtain 5-azidomethyl-3-(4-benzyloxy-phenyl)-isoxazole. A reduction of the compound was performed under NaBH4 conditions to obtain C-[3-(4-benzyloxy-phenyl)-isoxazol-5-yl]-methylamine as a desired compound.

152.3
[3-(4-benzyloxy-phenyl)-isoxazol-5-ylmethyl]-urea

C-[3-(4-benzyloxy-phenyl)-isoxazol-5-yl]-methylamine was dissolved in 10 ml of
THF, to which solution was added 1.7 equivalents of 1,1-carbonyldiimidazole. The consumption of all the reactants was confirmed by TLC, followed by addition of 2 equivalents of aqueous ammonia to the reaction solution. 2 hours later, the solvent was distilled off under reduced pressure and 50 me of 1N—HCl aqueous solution was added to the reactants, followed by extraction three times with 30 ml of ethyl acetate. The obtained organic layer was distilled under reduced pressure, followed by column chromatography to obtain [3-(4-benzyloxy-phenyl)-isoxazol-5-ylmethyl]-urea as a desired compound.
1H-NMR (CD3OD, 200 MHz) δ 7.7 (d, 2H), 7.4 (m, 5H), 7.1 (d, 2H), 6.6 (s, 1H), 5.1 (s, 2H), 4.5 (s, 2H), 2.63

Example 153

N-[3-(4-benzyloxy-phenyl)-isoxazol-5-ylmethyl]-guanidine

153.1 N-[3-(4-benzyloxy-phenyl)-isoxazol-5-ylmethyl]-N,N'-di-BOC-guanidine 0.52 g of di-BOC-guanidine and 0.393 g of triphenylphosphine were dissolved in 5 ml of THF, to which solution was slowly added a solution of 0.281 g (1 mmol) of [3-(4-benzyloxy-phenyl)-isoxazol-5-yl]-methanol dissolved in 5 ml of THF. The temperature of the reactants was reduced to 0° C., 0.3 me of diisopropyl azodicarboxylate was slowly added to the solution, and the resulting mixture was stirred at room temperature for another 3 hours. Subsequently, the reactants were distilled under reduced pressure to remove the solvent, followed by column chromatography to obtain N-[3-(benzyloxy-phenyl)-isoxazol-5-ylmethyl]-N,N'-di-BOC-guanidine as a desired compound.

153.2 N-[3-(4-benzyloxy-phenyl)-isoxazol-5-ylmethyl]-guanidine

The compound N-[3-(4-benzyloxy-phenyl)-isoxazol-5-ylmethyl]-N,N'-di-BOC-guanidine obtained above was dissolved in 10 ml of methylene chloride, to which solution was added 5 ml of trifluoroacetic acid, and the mixture was stirred at room temperature for 5 hours. The reactants were distilled under reduced pressure to remove the solvent and pH of the reactants was regulated to 8 with aqueous ammonia, followed by extraction three times with 20 ml of chloroform. The organic layer was dried and distilled under reduced pressure to obtain N-[3-(4-benzyloxy-phenyl)-isoxazol-5-ylmethyl]-guanidine as a desired compound.
1H-NMR (CD3OD, 200 MHz) δ 7.8 (d, 2H), 7.4 (m, 5H), 7.1 (d, 2H), 6.8 (s, 1H), 5.2 (s, 2H), 4.6 (s, 2H)

Example 154

3-[4-(2,4-difluoro-benzyloxy)-phenyl]-5-imidazol-1-ylmethyl-isoxazole

The compound was synthesized using 2,4-difluorobenzyl bromide in the same manner as in Example 142.
1H-NMR (CDCl3, 200 MHz) δ 7.67 (m, 3H), 7.43 (m, 1H), 6.85-7.13 (m, 6H), 6.34 (s, 1H), 5.28 (s, 2H), 5.10 (s, 2H)

Example 155

5-imidazol-1-ylmethyl-3-[4-(2,4,6-trifluoro-benzyloxy)-phenyl]-isoxazole

The compound was synthesized using 2,4,6-trifluorobenzyl bromide in the same manner as in Example 142.
1H-NMR (CDCl3, 200 MHz) δ 7.67 (t, 3H), 7.27 (m, 4H), 7.00 (t, 2H), 6.35 (s, 1H), 5.28 (s, 2H), 5.09 (s, 2H)

Example 156

3-[4-(4-fluoro-benzyloxy)-phenyl]-5-imidazol-1-ylmethyl-isoxazole

The compound was synthesized using 4-fluorobenzyl bromide in the same manner as in Example 142.
1H-NMR (CDCl3, 200 MHz) δ 7.69 (t, 3H), 7.62 (m, 1H), 7.39 (m, 2H), 7.03 (m, 6H), 5.27 (s, 2H), 5.05 (s, 2H)

Example 157

3-[4-(4-chloro-benzyloxy)-phenyl]-5-imidazol-1-ylmethyl-isoxazole

The compound was synthesized using 4-chlorobenzyl bromide in the same manner as in Example 142.
1H-NMR (CDCl3, 200 MHz) δ 7.66 (t, 3H), 7.62 (m, 1H), 7.36 (m, 4H), 7.14 (s, 1H), 7.03 (d, 2H), 5.28 (s, 2H), 5.07 (s, 2H)

Example 158

3-[4-(4-fluoro-benzyloxy)-phenyl]-5-(4-methyl-imidazol-1-ylmethyl)-isoxazole

An experiment was performed in the same manner as in Example 139 to synthesize 4-[5-(4-methyl-imidazol-1-ylmethyl)-isoxazol-3-yl]-phenol as an intermediate, and then a synthesis was performed using 4-fluorobenzyl bromide in the same manner as in Example 142.
1H-NMR (CDCl3, 200 MHz) δ 7.73 (d, 2H), 7.60 (s, 1H), 7.43 (m, 2H), 7.06 (m, 4H), 6.77 (s, 1H), 6.37 (s, 1H), 5.23 (s, 2H), 5.08 (s, 2H), 2.63 (s, 3H)

Example 159

3-[4-(3-fluoro-benzyloxy)-phenyl]-5-(4-methyl-imidazol-1-ylmethyl)-isoxazole

The compound was synthesized using 3-fluorobenzyl bromide in the same manner as in Example 158.
1H-NMR (CDCl3, 200 MHz) δ 7.73 (d, 2H), 7.61 (s, 1H), 7.38 (m, 2H), 7.22 (m, 4H), 6.77 (s, 1H), 6.37 (s, 1H), 5.22 (s, 2H), 5.11 (s, 2H), 2.26 (s, 3H)

Example 160

3-[4-(2,4-difluoro-benzyloxy)-phenyl]-5-(4-methyl-imidazol-1-ylmethyl)-isoxazole The compound was synthesized using 2,4-difluorobenzyl bromide in the same manner as in Example 158.
1H-NMR (CDCl3, 200 MHz) δ 7.96 (s, 1H), 7.73 (d, 2H), 7.29 (m, 1H), 7.06 (d, 2H), 6.96 (m, 2H), 6.82 (s, 2H), 6.49 (s, 2H), 5.33 (s, 2H), 5.17 (s, 2H), 2.28 (s, 3H)

Example 161

Carbamic acid 3-[4-(1-oxy-pyridin-2-ylmethoxy)-phenyl]-isoxazol-5-ylmethyl ester 0.28 g of carbamic acid 3-[4-(pyridin-2-ylmethoxy)-phenyl]-isoxazol-5-ylmethyl ester in Example 65 was dissolved in 10 ml of dichloromethane, to which solution was added 0.22 g of m-chloroperbenzoic acid, and the mixture was stirred at room temperature for 12 hours. The completion of the reaction was confirmed by TLC and 10 ml of water was added to the reactants to separate an organic layer. A crude material obtained after drying and distillation of the organic layer under reduced pressure was separated by column chromatography to synthesize carbamic acid 3-[4-(1-oxy-pyridin-2-ylmethoxy)-phenyl]-isoxazol-5-ylmethyl ester as a desired compound.
1H-NMR (DMSO-d6, 200 MHz) δ 8.35 (d, 1H), 7.8 (d, 2H), 7.6 (d, 1H), 7.4 (d, 2H), 7.2 (d, 2H), 7.0 (s, 1H), 6.8 (brs, 2H), 5.3 (s, 2H), 5.1 (s, 2H)

Example 162

2-{[3-(4-benzyloxy-phenyl)-isoxazol-5-ylmethyl]-amino}-acetamide

The compound was synthesized using glycinamide instead of propargyl amine in the same manner as in Example 119.
1H-NMR (CDCl3, 200 MHz) δ 7.75 (d, 2H), 7.42 (m, 5H), 7.05 (d, 2H), 6.96 (brs, 1H), 6.45 (s, 1H), 5.5 (brs, 1H), 5.17 (s, 2H), 4.0 (s, 2H), 3.39 (s, 2H)

Example 163

2-{[3-(4-benzyloxy-phenyl)-isoxazol-5-ylmethyl]-amino}-propionamide

The compound was synthesized using alaninamide in the same manner as in Example 119.
1H-NMR (CDCl3, 200 MHz) δ 7.75 (d, 2H), 7.42 (m, 5H), 7.04 (d, 2H), 6.99 (brs, 1H), 6.43 (s, 1H), 5.6 (brs, 1H), 5.13 (s, 2H), 3.96 (s, 2H), 3.3 (q, 1H), 1.38 (d, 3H)

Example 164

2-{[3-(4-benzyloxy-phenyl)-isoxazol-5-ylmethyl]-amino}-2-methyl-propionamide

The compound was synthesized using 2-amino-2-methyl-propionamide in the same manner as in Example 119.

1H-NMR (CDCl3, 200 MHz) δ 7.75 (d, 2H), 7.43 (m, 5H), 7.2 (brs, 1H), 7.05 (d, 2H), 6.44 (s, 1H), 5.2 (brs, 1H), 5.14 (s, 2H), 3.9 (s, 2H), 1.45 (s, 6H)

Example 165

Synthesis of carbamic acid 1-[3-(4-benzyloxy-phenyl)-isoxazol-5-yl]-1-methyl-ethyl ester The compound was synthesized using 2-methyl-but-3-yn-2-ol instead of propargyl alcohol in the same manner as in Example 1.
1H-NMR (CD3OD, 200 MHz) δ 7.75 (d, 2H), 7.45 (m, 5H), 7.0 (d, 2H), 6.4 (s, 1H), 5.12 (s, 2H), 4.6 (brs, 2H), 1.87 (s, 6H)

Example 166

Carbamic acid 2-{[3-(4-benzyloxy-phenyl)-isoxazol-5-ylmethyl]-amino}-propyl ester hydrochloride The compound was synthesized using carbamic acid 2-amino-propyl ester in the same manner as in Example 119.
1H-NMR (DMSO-d6, 200 MHz) δ 9.9 (brs, 2H), 7.8 (d, 2H), 7.44 (m, 5H), 7.2 (d, 2H), 6.7 (s, 2H), 5.17 (s, 2H), 4.5 (s, 2H), 4.17 (s, 2H), 3.5 (m, 1H), 1.3 (s, 3H)

Example 167

2-{[3-(4-benzyloxy-phenyl)-isoxazol-5-ylmethyl]-amino}-3-hydroxy-propionamide

The compound was synthesized using L-serinamide in the same manner as in Example 119.
1H-NMR (CDCl3, 200 MHz) δ 7.72 (d, 2H), 7.4 (m, 5H), 7.1 (d, 2H), 6.46 (s, 1H), 5.1 (s, 2H), 4.01 (s, 2H), 3.86 (brs, 1H), 3.4 (m, 1H)

Example 168

2-{[3-(4-benzyloxy-phenyl)-isoxazol-5-ylmethyl]-amino}-ethanol

The compound was synthesized using 2-aminoethanol in the same manner as in Example 119.
1H-NMR (CDCl3, 200 MHz) 7.75 (d, 2H), 7.4 (m, 5H), 7.05 (d, 2H), 6.44 (s, 2H), 5.13 (s, 2H), 4.0 (s, 2H), 3.71 (t, 2H), 2.9 (t, 2H)

Example 169

2-{[3-(4-benzyloxy-phenyl)-isoxazol-5-ylmethyl]-amino}-propan-1-ol

The compound was synthesized using 2-aminopropanol in the same manner as in Example 119.
1H-NMR (CDCl3, 200 MHz) 7.75 (d, 2H), 7.4 (m, 5H), 7.05 (d, 2H), 6.45 (s, 2H), 5.13 (s, 2H), 4.0 (dd, 2H), 3.6 (dd, 1H), 3.4 (dd, 1H), 2.9 (m, 1H), 2.1 (brs, 1H), 1.1 (d, 3H)

Example 170

2-{[3-(4-benzyloxy-phenyl)-isoxazol-5-ylmethyl]-amino}-butan-1-ol

The compound was synthesized using 2-aminobutanol in the same manner as in Example 119.
1H-NMR (CDCl3, 200 MHz) 7.75 (d, 2H), 7.42 (m, 5H), 7.05 (d, 2H), 6.45 (s, 2H), 5.13 (s, 2H), 4.0 (dd, 2H), 3.7 (dd, 1H), 3.4 (dd, 1H), 2.7 (m, 1H), 1.5 (m, 2H), 0.95 (t, 3H)

Example 171

2-{[3-(4-benzyloxy-phenyl)-isoxazol-5-ylmethyl]-amino}-2-methyl-propan-1-ol

The compound was synthesized using 2-amino2-methyl-propanol in the same manner as in Example 119.
1H-NMR (CDCl3, 200 MHz) 7.75 (d, 2H), 7.42 (m, 5H), 7.05 (d, 2H), 6.45 (s, 2H), 5.13 (s, 2H), 3.9 (s, 2H), 3.4 (s, 2H), 1.16 (s, 6H)

Example 172

2-{[3-(4-benzyloxy-phenyl)-isoxazol-5-ylmethyl]-amino}-3-methyl-butan-1-ol

The compound was synthesized using 2-amino3-methylbutanol in the same manner as in Example 119.
1H-NMR (CDCl3, 200 MHz) 7.75 (d, 2H), 7.4 (m, 5H), 7.05 (d, 2H), 6.45 (s, 2H), 5.12 (s, 2H), 4.0 (dd, 2H), 3.7 (dd, 1H), 3.4 (dd, 1H), 2.5 (m, 1H), 2.2 (brs, 1H), 1.8 (m, 1H), 0.95 (dd, 6H)

Example 173

2-{[3-(4-benzyloxy-phenyl)-isoxazol-5-ylmethyl]-amino}-propan-1,3-diol

The compound was synthesized using L-serinol in the same manner as in Example 119.
1H-NMR (CDCl3, 200 MHz) 7.72 (d, 2H), 7.45 (m, 5H), 7.04 (d, 2H), 6.48 (s, 2H), 5.13 (s, 2H), 4.04 (dd, 2H), 3.67 (m, 4H), 2.9 (m, 1H), 2.2 (brs, 1H)

Example 174

[3-(4-benzyloxy-phenyl)-isoxazol-5-ylmethyl]-(2-methoxy-ethyl)-amine

The compound was synthesized using 2-methoxy-ethalamine in the same manner as in Example 119.
1H-NMR (CDCl3, 200 MHz) 7.75 (d, 2H), 7.4 (m, 5H), 7.05 (d, 2H), 6.44 (s, 2H), 5.12 (s, 2H), 4.0 (s, 2H), 3.53 (t, 2H), 3.38 (s, 3H), 2.9 (t, 2H)

Example 175

Carbamic acid 1-{3-[4-(pyridin-2-ylmethoxy)-phenyl]-isoxazol-5-yl}-ethyl ester

The compound was synthesized using carbamic acid 1-[3-(4-benzyloxy-phenyl)-isoxazol-5-yl]-ethyl ester of example 117 in the same manner as in Example 10 by debenzylation following reaction with 2-bromomethylpyridine.
1H-NMR (CDCl3, 200 MHz) δ 8.63 (d, 1H), 7.74 (d, 3H), 7.5 (d, 1H), 7.2 (d, 1H), 7.1 (d, 2H), 6.5 (s, 1H), 6.0 (q, 1H), 5.3 (s, 2H), 4.8 (brs, 2H), 1.68 (d, 3H)

Example 176

Allyl-[3-(4-benzyloxy-phenyl)-isoxazol-5-ylmethyl]-amine

A side product obtained after reaction in the same manner as in Example 119 was separated by column chromatography using a solvent of ethyl acetate:hexane (1:2) as a mobile phase to obtain a desired compound.

1H-NMR (CDCl3, 200 MHz) δ 7.77 (d, 2H), 7.45 (m, 5H), 7.05 (d, 2H), 6.44 (s, 1H), 5.9 (m, 1H), 5.2 (dd, 2H), 5.1 (s, 2H), 3.9 (s, 2H), 3.35 (d, 2H)

Example 177

Carbamic acid 2-{[3-(4-benzyloxy-phenyl)-isoxazol-5-ylmethyl]-amino}-ethyl ester The compound was synthesized using carbamic acid 2-amino-ethyl ester in the same manner as in Example 119.

1H-NMR (DMSO-d6, 200 MHz) 9.83 (brs, 2H), 7.81 (d, 2H), 7.47 (m, 5H), 7.2 (s, 1H), 7.15 (d, 2H), 6.68 (s, 2H), 5.19 (s, 2H), 4.5 (t, 2H), 4.23 (t, 2H)

Example 178

[3-(4-benzyloxy-phenyl)-isoxazol-5-ylmethyl]-methyl-prop-2-ynyl-amine

The compound was synthesized using N-methylpropargylamine in the same manner as in Example 139.

1H-NMR (CDCl3, 200 MHz) δ 7.75 (d, 2H), 7.4 (m, 5H), 7.05 (d, 2H), 6.49 (s, 1H), 5.13 (s, 2H), 3.82 (s, 2H), 3.43 (d, 2H), 2.44 (s, 3H), 2.33 (d, 1H)

Example 179

3-(4-benzyloxy-phenyl)-5-(2-isopropyl-imidazol-1-ylmethyl)-isoxazole

The compound was synthesized using 2-isopropylimidazole in the same manner as in Example 139.

1H-NMR (CDCl3, 200 MHz) δ 7.7 (d, 2H), 7.4 (m, 5H), 7.05 (m, 4H), 6.2 (s, 1H), 5.2 (s, 2H), 5.1 (s, 2H), 3.0 (m, 1H), 1.3 (d, 6H)

Example 180

3-(4-benzyloxy-phenyl)-5-(4-bromo-imidazol-1-ylmethyl)-isoxazole

The compound was synthesized using 4-bromoimidazole in the same manner as in Example 139.

1H-NMR (CDCl3, 200 MHz) δ 7.7 (d, 2H), 7.4 (m, 6H), 7.0 (m, 3H), 6.4 (s, 1H), 5.2 (s, 2H), 5.1 (s, 2H)

Example 181

3-(4-benzyloxy-phenyl)-5-(4,5-dichloro-imidazol-1-ylmethyl)-isoxazole

An experiment was performed using 4,5-dichloroimidazole in the same manner as in Example 139.

1H-NMR (CDCl3, 200 MHz) δ 7.7 (d, 2H), 7.5 (m, 6H), 7.0 (m, 2H), 6.5 (s, 1H), 5.2 (s, 2H), 5.1 (s, 2H)

Example 182

3-(4-benzyloxy-phenyl)-5-(2-methyl-4,5-dichloro-imidazol-1-ylmethyl)-isoxazole

An experiment was performed using 2-methyl-4,5-dichloroimidazole in the same manner as in Example 139.

1H-NMR (CDCl3, 200 MHz) δ 7.7 (d, 2H), 7.4 (m, 6H), 7.05 (m, 2H), 6.35 (s, 1H), 5.18 (s, 2H), 5.12 (s, 2H), 2.48 (s, 3H)

Example 183

3-(4-benzyloxy-phenyl)-5-(2-nitro-imidazol-1-ylmethyl)-isoxazole

An experiment was performed using 2-nitroimidazole in the same manner as in Example 139.

1H-NMR (CDCl3, 200 MHz) δ 7.7 (d, 2H), 7.4 (m, 5H), 7.2 (dd, 2H), 7.05 (m, 2H), 6.6 (s, 1H), 5.78 (s, 2H), 5.12 (s, 2H)

Example 184

3-(4-benzyloxy-phenyl)-5-(4-phenyl-imidazol-1-ylmethyl)-isoxazole

An experiment was performed using 4-phenylimidazole in the same manner as in Example 139.

1H-NMR (CDCl3, 200 MHz) δ 7.7 (m, 5H), 7.4 (m, 9H), 7.2 (dd, 2H), 7.05 (m, 2H), 6.4 (s, 1H), 5.3 (s, 2H), 5.12 (s, 2H)

Example 185

3-(4-benzyloxy-phenyl)-5-(4-nitro-imidazol-1-ylmethyl)-isoxazole

An experiment was performed using 4-nitroimidazole in the same manner as in Example 139.

1H-NMR (CDCl3, 200 MHz) δ 7.92 (s, 1H), 7.7 (d, 2H), 7.4 (m, 5H), 7.05 (d, 2H), 6.56 (s, 1H), 5.37 (s, 2H), 5.13 (s, 2H)

Example 186

3-(4-benzyloxy-phenyl)-5-(2-ethyl-4-methyl-imidazol-1-ylmethyl)-isoxazole

An experiment was performed using 2-ethyl-4-methylimidazole in the same manner as in Example 139.

1H-NMR (CDCl3, 200 MHz) δ 7.7 (d, 2H), 7.4 (m, 5H), 7.05 (d, 2H), 6.64 (s, 1H), 6.23 (s, 1H), 5.12 (s, 4H), 2.7 (q, 2H), 2.22 (s, 3h), 1.3 (t, 3H)

Example 187

3-(4-benzyloxy-phenyl)-5-(2-chloroimidazol-1-ylmethyl)-isoxazole

An experiment was performed using 2-chloroimidazole in the same manner as in Example 139.

1H-NMR (CDCl3, 200 MHz) δ 7.7 (d, 2H), 7.4 (m, 5H), 7.05 (m, 4H), 6.4 (s, 1H), 5.26 (s, 2H), 5.12 (s, 2H)

Example 188

3-(4-benzyloxy-phenyl)-5-(2-bromoimidazol-1-ylmethyl)-isoxazole

An experiment was performed using 2-bromoimidazole in the same manner as in Example 139.

1H-NMR (CDCl3, 200 MHz) δ 7.71 (d, 2H), 7.4 (m, 5H), 7.1 (m, 4H), 6.38 (s, 1H), 5.26 (s, 2H), 5.12 (s, 2H)

Example 189

3-(4-benzyloxy-phenyl)-5-(2-bromo-4,5-dichlor-oimidazol-1-ylmethyl)-isoxazole

An experiment was performed using 2-bromo-4,5-dichloroimidazole in the same manner as in Example 139.

1H-NMR (CDCl3, 200 MHz) δ 7.7 (d, 2H), 7.4 (m, 5H), 7.05 (d, 2H), 6.43 (s, 1H), 5.3 (s, 2H), 5.13 (s, 2H)

Example 190

3-(4-benzyloxy-phenyl)-5-(2,4,5-tribromo-imidazol-1-ylmethyl)-isoxazole

An experiment was performed using 2,4,5-tribromoimidazole in the same manner as in Example 139.

1H-NMR (CDCl3, 200 MHz) δ 7.7 (d, 2H), 7.4 (m, 5H), 7.05 (d, 2H), 6.41 (s, 1H), 5.35 (s, 2H), 5.13 (s, 2H)

Example 191

3-(4-benzyloxy-phenyl)-5-(2-ethyl-imidazol-1-ylmethyl)-isoxazole

An experiment was performed using 2-ethylimidazole in the same manner as in Example 139.

1H-NMR (CDCl3, 200 MHz) δ 7.69 (d, 2H), 7.38 (m, 5H), 7.02 (m, 4H), 6.241 (s, 1H), 5.19 (s, 2H), 5.11 (s, 2H), 2.81 (q, 2H), 1.33 (t, 3H)

Example 192

2-[4-(5-carbamoyloxymethyl-isoxazol-3-yl)-phenoxymethyl]-1-methyl-pyridinium iodide 2 ml of iodomethane was added to 0.3 g of the compound carbamic acid 3-[4-(pyridin-2-ylmethoxy)-phenyl]-isoxazol-5-ylmethyl ester in Example 65 and stirred at 80° C. for 10 hours. A crude solid compound obtained after distillation of the solution under reduced pressure to remove an excess of MeI was recrystallized from ethyl acetate/hexane/methylene chloride to obtain 2-[4-(5-carbamoyloxymethyl-isoxazol-3-yl)-phenoxymethyl]-1-methyl-pyridinium iodide as a desired compound.

1H-NMR (DMSO-d6, 200 MHz) δ 9.1 (d, 2H), 8.63 (t, 1H), 8.26 (d, 1H), 8.14 (t, 1H), 7.9 (d, 2H), 7.36 (d, 2H), 7.06 (s, 1H), 6.8 (brs, 1H), 5.68 (s, 2H), 5.14 (s, 2H), 4.36 (s, 3H)

Example 193

Carbamic acid 3-(4-cyclopentylmethoxy-phenyl)-isoxazol-5-ylmethyl ester

[3-(4-cyclopentylmethoxy-phenyl)-isoxazol-5-yl]-methanol was synthesized using 4-(5-hydroxymethyl-isoxazol-3-yl)-phenol and toluene-4-sulfonic acid cyclopentylmethyl ester in the same manner as in Example 10, and then a carbamoylation of the compound was performed to obtain carbamic acid 3-(4-cyclopentylmethoxy-phenyl)-isoxazol-5-ylmethyl ester as a desired compound.

1H-NMR (CdCl3, 200 MHz) δ 7.7 (d, 2H), 6.95 (d, 2H), 6.6 (s, 1H), 5.25 (s, 2H), 4.8 (brs, 2H), 3.88 (d, 2H), 2.4 (m, 1H), 1.87 (m, 2H), 1.63 (m, 4H), 1.35 (m, 2H)

Example 194

Carbamic acid 3-[4-(benzyl-ethyl-amino)-phenyl]-isoxazol-5-ylmethyl ester

An experiment was performed using carbamic acid 3-(4-benzylamino-phenyl)-isoxazol-5-ylmethyl ester in Example 74 as a starting material and acetaldehyde in the same manner as in Example 74.4 to obtain carbamic acid 3-[4-(benzyl-ethyl-amino)-phenyl]-isoxazol-5-ylmethyl ester.

1H-NMR (CDCl3, 200 MHz) δ 7.63 (d, 2H), 7.3 (m, 5H), 6.7 (d, 2H), 6.5 (s, 1H), 5.2 (s, 2H), 4.9 (brs, 2H), 4.6 (s, 2H), 3.6 (q, 2H), 1.25 (t, 3H)

Example 195

Carbamic acid 3-[4-(benzyl-propyl-amino)-phenyl]-isoxazol-5-ylmethyl ester

An experiment was performed using the compound carbamic acid 3-(4-benzylamino-phenyl)-isoxazol-5-ylmethyl ester in Example 74 as a starting material and propionaldehyde in the same manner as in Example 74.4 to obtain carbamic acid 3-[4-(benzyl-propyl-amino)-phenyl]-isoxazol-5-ylmethyl ester.

1H-NMR (CDCl3, 200 MHz) δ 7.6 (d, 2H), 7.34 (m, 5H), 6.7 (d, 2H), 6.52 (s, 1H), 5.22 (s, 2H), 4.8 (brs, 2H), 4.6 (s, 2H), 3.43 (t, 2H), 1.75 (m, 2H), 0.98 (t, 3H)

Example 196

Synthesis of carbamic acid 3-[4-(2,4-difluoro-benzyloxy)-phenyl]-isoxazol-5-ylmethyl ester The compound was synthesized using 2,4-di-fluorobenzyl bromide in the same manner as in Example 10.

1H-NMR (CDCl3, 200 MHz) δ 7.77 (d, 2H), 7.47 (q, 1H), 7.06 (d, 2H), 6.91 (dd, 2H), 6.59 (s, 1H), 5.21 (s, 2H), 5.12 (s, 2H), 4.81 (brs, 2H)

Example 197

Synthesis of carbamic acid 3-[4-(2,5-difluoro-benzyloxy)-phenyl]-isoxazol-5-ylmethyl ester The compound was synthesized using 2,5-di-fluorobenzyl bromide in the same manner as in Example 10.

1H-NMR (CDCl3, 200 MHz) δδ 7.76 (d, 2H), 7.26 (s, 1H), 7.10 (m, 4H), 6.59 (s, 1H), 5.21 (s, 2H), 5.16 (s, 2H), 4.78 (brs, 2H)

Example 198

Synthesis of carbamic acid 3-[4-(2,4-dichlorobenzyloxy)-phenyl]-isoxazol-5-ylmethyl ester The compound was synthesized using 2,4-chlorobenzyl-bromide in the same manner as in Example 10.

1H-NMR (CDCl3, 200 MHz) δ 7.78 (d, 2H), 7.53 (m, 2H), 7.45 (d, 1H), 7.04 (d, 2H), 6.59 (s, 1H), 5.22 (s, 2H), 5.17 (s, 2H), 4.89 (brs, 2H)

Example 199

Carbamic acid 3-[4-(2-chloro-6-fluorobenzyloxy)-phenyl]-isoxazol-5-ylmethyl ester The compound was synthesized using 2-chloro-6-fluorobenzyl bromide in the same manner as in Example 10.
1H-NMR (CDCl3, 200 MHz) δ 7.78 (d, 2H), 7.29 (m, 2H), 7.12 (m, 3H), 6.60 (s, 1H), 5.24 (s, 4H), 4.89 (brs, 2H)

Example 200

Synthesis of carbamic acid 3-[4-(3-methyl-benzyloxy)-phenyl]-isoxazol-5-ylmethyl ester The compound was synthesized using 3-methylbenzyl bromide in the same manner as in Example 10.
1H-NMR (DMSO-d6, 200 MHz) δ 7.8 (d, 2H), 7.28 (m, 3H), 7.18 (d, 3H), 6.99 (s, 1H), 6.8 (brs, 2H), 5.13 (s, 4H), 2.33 (s, 3H)

Example 201

Synthesis of carbamic acid 3-[4-(2-trifluoromethyl-benzyloxy)-phenyl]-isoxazol-5-ylmethyl ester The compound was synthesized using 2-trifluoromethyl-benzyl bromide in the same manner as in Example 10.
1H-NMR (CDCl3, 200 MHz) δ 7.7-7.4 (m, 6H), 7.07 (d, 2H), 6.59 (s, 1H), 5.33 (s, 2H), 5.22 (s, 2H), 4.8 (brs, 2H)

Example 202

Synthesis of carbamic acid 3-[4-(4-trifluoromethyl-benzyloxy)-phenyl]-isoxazol-5-ylmethyl ester The compound was synthesized using 4-trifluoromethyl-benzyl bromide in the same manner as in Example 10.
1H-NMR (CDCl3, 200 MHz) δ 7.79 (d, 2H), 7.68 (d, 2H), 7.58 (d, 2H), 7.05 (d, 2H), 6.60 (s, 1H), 5.23 (s, 2H), 5.20 (s, 2H), 4.8 (brs, 2H)

Example 203

Synthesis of carbamic acid 3-[4-(benzo[1,3]dioxol-5-ylmethoxy)-phenyl]-isoxazol-5-ylmethyl ester The compound was synthesized using 5-bromomethyl-benzo[1,3]dioxole in the same manner as in Example 10.
1H-NMR (CDCl3, 200 MHz) δ 7.76 (d, 2H), 7.05 (d, 2H), 6.89 (m, 3H), 6.59 (s, 1H), 6.0 (s, 2H), 5.22 (s, 2H), 5.01 (s, 2H), 4.8 (brs, 2H)

Example 204

Synthesis of carbamic acid 3-{4-[3-(t-butylnitronyl)-benzyloxy]-phenyl}-isoxazol-5-ylmethyl ester An oxime reaction of the 4-carbamic acid 3-[4-(3-formyl-benzyloxy)-phenyl]-isoxazol-5-ylmethyl ester obtained above with N-t-butyl hydroxylamine was performed in the same manner as in Example 1-1 to obtain carbamic acid 3-{4-[3-(t-butylnitronyl)-benzyloxy]-phenyl}-isoxazol-5-ylmethyl ester as a desired compound.
1H-NMR (CDCl3, 200 MHz) δ 8.58 (s, 1H), 8.2 (d, 1H), 7.7 (d, 2H), 7.6 (s, 1H), 7.5 (m, 2H), 7.0 (d, 2H), 6.58 (s, 1H), 5.21 (s, 2H), 5.16 (s, 2H), 4.8 (brs, 2H), 1.94 (s, 9H)

Analyses of behavioral changes, brain tissue lesions, dopamine concentrations, etc. were performed using MAO-B inhibitory effects and the MPTP mouse model and 6-OHDA rat model as an animal model of Parkinson's disease in order to verify the efficacy of the compound for treatment of Parkinson's disease.

Hereinafter, what is mentioned above will be described in more detail.

In the following Examples, IP refers to intraperitoneal administration, PO to oral administration, IC50 to concentration at which 50% of the disease is inhibited, ED50 to the dose at which 50% of efficacy is shown, MAO-A to MonoamineOxidase A, and MAO-B to MonoamineOxidase B.

Example 205

Inhibitory Effects of a Composition Containing the Azole Derivative of Formula (I) on the Activities of Monoamineoxidases A and B (1) Materials and Methods Monoamineoxidase A or B type human-derived enzyme (5 mg/ml) was each diluted with 0.05 M sodium phosphate buffer (pH 7.4) to yield a dilution of 1:200, and then 100 μl of an enzyme buffer containing 2 μl of a compound 1 solution at the corresponding concentration was placed in a test plate (flat-bottom) and incubated for 30 minutes.

100 μl of a working buffer containing 400 μM of Amplex Red reagent, 2 U/ml horseradish peroxidase, and 2 mM substrate (tyramine for MAO-A and benzylamine for MAO-B) in 0.05 M sodium phosphate buffer (pH 7.4) was mixed with a pre-incubated enzyme buffer at 1:1 and measured using fluorescence (EX: 563 nm & EM: 587 nm) for 30 minutes.

Because MAO-A has high homology with MAO-B and is different from MAO-B in function, the selectivity of MAO-A/B has an influence on the safety of a drug, playing an important role in evaluation of the drug.

(2) Results

1) MAO-B

The following Table 1 shows MAO-B inhibitory effects according to treatment concentrations of each compound in Examples in the same manner as in the methods described above

TABLE 1

| Inhibitory effects on the activity of MAO-B | | | | | | | | |
| --- | --- | --- | --- | --- | --- | --- | --- | --- |
| No. of Compound | Treatment concentration | Inhibitory effects (%) | No. of Compound | Treatment concentration | Inhibitory effects (%) | No. of Compound | Treatment concentration | Inhibitory effects (%) |
| 1 | 10 nM | 96.6 | 2 | 10 nM | 95.0 | 3 | 10 nM | 95.2 |
| 4 | 10 nM | 92.0 | 5 | 10 nM | 88.3 | 6 | 10 nM | 90.7 |

TABLE 1-continued

Inhibitory effects on the activity of MAO-B

| No. of Compound | Treatment concentration | Inhibitory effects (%) | No. of Compound | Treatment concentration | Inhibitory effects (%) | No. of Compound | Treatment concentration | Inhibitory effects (%) |
|---|---|---|---|---|---|---|---|---|
| 7 | 10 nM | 75.9 | 8 | 10 nM | 72.7 | 10 | 10 nM | 98.2 |
| 11 | 10 nM | 101.1 | 12 | 10 nM | 94.1 | 13 | 10 nM | 102.1 |
| 14 | 10 nM | 96.0 | 15 | 10 nM | 96.2 | 16 | 10 nM | 96.5 |
| 17 | 10 nM | 96.8 | 18 | 10 nM | 91.5 | 19 | 10 nM | 94.2 |
| 20 | 10 nM | 96.2 | 21 | 10 nM | 92.9 | 22 | 10 nM | 86.0 |
| 23 | 10 nM | 92.7 | 24 | 10 nM | 83.3 | 25 | 10 nM | 83.2 |
| 26 | 10 nM | 87.3 | 27 | 10 nM | 75.2 | 28 | 10 nM | 87.4 |
| 29 | 10 nM | 80.3 | 30 | 10 nM | 90.2 | 31 | 100 nM | 96.2 |
| 32 | 10 nM | 84.4 | 35 | 10 nM | 90.4 | 36 | 10 nM | 90.1 |
| 37 | 10 nM | 92.3 | 38 | 10 nM | 91.7 | 42 | 10 nM | 85.3 |
| 43 | 10 nM | 96.8 | 44 | 10 nM | 74.3 | 45 | 10 nM | 87.6 |
| 47 | 10 nM | 41.2 | 48 | 10 nM | 48.4 | 52 | 10 nM | 26.6 |
| 57 | 10 nM | 25.0 | 58 | 10 nM | 88.1 | 59 | 10 nM | 97.4 |
| 62 | 10 nM | 98.6 | 64 | 10 nM | 32.8 | 65 | 10 nM | 89.9 |
| 66 | 10 nM | 87.3 | 67 | 10 nM | 94.2 | 68 | 10 nM | 63.4 |
| 69 | 10 nM | 83.6 | 70 | 10 nM | 27.1 | 71 | 10 nM | 56.0 |
| 72 | 10 nM | 87.9 | 73 | 10 nM | 58.1 | 74 | 10 nM | 84.5 |
| 76 | 10 nM | 87.0 | 77 | 10 nM | 77.1 | 78 | 10 nM | 84.7 |
| 79 | 10 nM | 84.6 | 80 | 10 nM | 74.5 | 81 | 10 nM | 91.4 |
| 82 | 10 nM | 56.5 | 83 | 10 nM | 54.9 | 84 | 10 nM | 88.5 |
| 85 | 10 nM | 50.1 | 86 | 10 nM | 83.3 | 87 | 10 nM | 78.6 |
| 88 | 10 nM | 60.0 | 89 | 10 nM | 54.7 | 90 | 10 nM | 20.3 |
| 91 | 10 nM | 73.1 | 92 | 10 nM | 75.2 | 93 | 10 nM | 24.1 |
| 95 | 10 nM | 24.3 | 96 | 10 nM | 40.9 | 99 | 10 nM | 79.7 |
| 100 | 10 nM | 23.7 | 101 | 10 nM | 80.5 | 103 | 10 nM | 20.7 |
| 104 | 10 nM | 89.1 | 105 | 10 nM | 53.7 | 110 | 10 nM | 80.8 |
| 111 | 10 nM | 69.0 | 112 | 10 nM | 26.0 | 117 | 10 nM | 68.5 |
| 118 | 10 nM | 25.7 | 119 | 10 nM | 81.7 | 120 | 10 nM | 87.8 |
| 121 | 10 nM | 82.8 | 125 | 10 nM | 65.8 | 126 | 10 nM | 48.7 |
| 127 | 10 nM | 45.3 | 129 | 10 nM | 22.0 | 130 | 10 nM | 52.9 |
| 137 | 10 nM | 43.5 | 138 | 10 nM | 39.1 | 139 | 10 nM | 84.6 |
| 140 | 10 nM | 91.7 | 141 | 10 nM | 92.2 | 142 | 10 nM | 89.5 |
| 143 | 10 nM | 98.1 | 144 | 10 nM | 97.3 | 145 | 10 nM | 39.2 |
| 146 | 10 nM | 86.0 | 148 | 10 nM | 79.0 | 150 | 10 nM | 97.4 |
| 151 | 10 nM | 96.8 | 152 | 10 nM | 96.1 | 154 | 10 nM | 82.71 |
| 155 | 10 nM | 70.69 | 156 | 10 nM | 74.48 | 157 | 10 nM | 37.23 |
| 162 | 10 nM | 66.11 | 167 | 10 nM | 21.77 | 168 | 10 nM | 44.66 |
| 174 | 10 nM | 52.73 | 176 | 10 nM | 71.5 | 177 | 10 nM | 31.7 |
| 178 | 10 nM | 64.0 | 179 | 10 nM | 26.74 | 186 | 10 nM | 51.18 |
| 193 | 10 nM | 88.1 | 196 | 100 nM | 97.1 | 197 | 100 nM | 96.7 |
| 198 | 100 nM | 95.7 | 199 | 10 nM | 83.2 | 200 | 10 nM | 87.6 |
| 201 | 10 nM | 72.4 | 202 | 100 nM | 95.5 | 203 | 10 nM | 93.0 |
| 204 | 10 nM | 98.8 | | | | | | |

It was confirmed that the azole derivatives to be subjected to experiments as above had potent inhibitory effects on the activity of MAO-B at the treatment concentration of 10 nM or 100 nM, showing the availability as a therapeutic agent for Parkinson's disease.

2) MAO-A

All the compounds described in Examples, etc. showed 30% or less inhibitory effects of MAO-A at 10 μM or 100 nM. Thus, it was confirmed that the azole derivatives had high MAO-A/B selectivity, compared to potent inhibitory effects of MAO-B, which the compounds of the present invention showed.

Example 206

Confirmation of Effects of the Azle Derivative Composition in a MPTP-Induced Mouse Model as an Animal Model of Parkinson's Disease It was confirmed that the azole derivative of Formula (I) exhibited protective effects against dopamine neuronal damage by administration of MPTP (1-methyl-4-phenyl-1,2,3,6-tetrahydropyridine) in an animal model of Parkinson's disease.

An acute administration model of MPTP generally used was constructed by administration of MPTP (free base) at 15~25 mg/kg four times at the interval of 2 hours for a day (Breidert et al., 2002), and it was known that at 3 to 7 days after administration of MPTP, the administration model showed 70~80% in brain damage, 40~50% in behavioral dysfunction, and a decrease in dopamine concentration in the brain by 70% or more, respectively compared to a control group (Sham) in which MPTP was not administered, and was gradually recovered at 7 to 8 days after MPTP treatment (Khaldy et al., 2003; Bezard et al., 2000; Muramatsu et al., 2002).

(1) Materials and Methods

A. MPTP (1-methyl-4-phenyl-1,2,3,6-tetrahydropyridine) and drug treatment MPTP (20 mg/kg, free base; Sigma, St. louis, Mo.) was administered to an 8 week old (20-25 g) male C57BL/6 test mouse intraperitoneally three times a day at the interval of 2 hours to construct a model (Breidert et al., 2002; Lichuan Yang, Shuei Sugama, Jason W. Chirichigno, Jason Gregorio, Stefan Lorenzl, Dong H. Shin, Susan E. Browne, Yoshinori Shimizu, Tong H. Joh, M. Flint Beal, l and David S. Alber. (2003) Minocycline Enhances MPTP Toxicity to Dopaminergic Neurons. J Neurosci Res. 74:278-285). In order to observe the protective effects of the compound as a candidate drug, the compound was dissolved in a solution containing 10% dimethylsulfoxide (DMSO), 10% Cremophor, and 40% polyethyleneglycol (PEG), and the resulting solution was orally administered at doses of 5 mg/kg, 0.5 mg/kg, 0.1 mg/kg, and 0.05 mg/kg 1 hour before and after MPTP treatment. Rasagiline as a control drug was also dissolved in the same solution, and the resulting solution was administered at the same doses in the same manner as above. A control group (Sham) in which MPTP was not administered was constructed by intraperitoneally administering saline solution to the group instead of MPTP in the same manner as above and orally administering the same solution 1 hour before and after PBS treatment.

B. Behavior Analysis Through a Tail Suspension Test

A tail suspension test was performed in order to measure the induction degree of behavioral dysfunctions in accordance with administration of MPTP and a drug. At 7 days after administration of the drug, a round stainless steel rod (width: 1 cm) was affixed to a cage (width: 16 cm, height: 40 cm) 35 cm above from the surface shielded by black wooden structures in the left and right sides to perform experiments. The time for which the animal moved for a total period of 6 minutes was measured in seconds to evaluate the drug action.

C. Measurement of Contents of Dopamine in the Striatum and Metabolites Thereof

The changes of contents of dopamine and dopamine metabolites in the striatum in accordance with administrations of MPTP and the drug were measured by high performance liquid chromatography (HPLC). At 7 days after administration of the drug, the animal was sacrificed by cervical vertebra dislocation and the brain tissues were immediately isolated from the animal. 0.5 ml of iced solution for HPLC analysis (0.1 M perchloric acid and 0.1 mM EDTA) was added to a striatum obtained from the isolated brain tissues, and an ultrasonic grinder was used to prepare a tissue homogenate. The tissue homogenate was centrifuged at 12,000 rpm for 15 minutes, and its supernatant was filtered through nitrocellulose membrane filter (0.2 um, Millipore). For HPLC analysis, uBondapak™ C18 column (4.6×150 mm, particle size 10 μm: Shisheido, Japan) was used, the flow rate of the mobile phase (0.07 M monobasic sodium phosphate), 1 mM sodium octasulfonic acid, 0.1 uM EDTA, 5% acetonitrile, pH 3.2) was maintained at 0.7 ml/min, and the electrode potential of the electrochemical detector (ICA-5000, Japan) was set at 700 mV.

D. Statistical Analysis

In order to confirm the damage and protective effects of dopamine neuron cells in accordance with administrations of MPTP and the drug, results from experiments performed five times or more were used and experimental data were expressed as the mean±standard error mean (SEM). Statistical analysis showed that the data were significant when the p value was 0.05 or less by a Student's t-test after a 1-way ANOVA test.

(2) Results

A. Behavior Analysis Through a Tail Suspension Test

A tail suspension test was performed at 7 days after administration of MPTP in order to review the behavioral dysfunction preventive effects of a drug against the MPTP toxicity, and the results were shown in the following Table 2.

TABLE 2

Tail suspension tests for the azole derivatives

| No. of Compound | Administration concentration | Mobility (%) |
|---|---|---|
| 1 | 10 | 112.79 |
| 3 | 10 | 70.3 |
| 6 | 10 | 82.9 |
| 11 | 10 | 82.2 |
| 12 | 10 | 85.3 |
| 14 | 10 | 75.3 |
| 37 | 10 | 77.5 |
| 38 | 10 | 73 |
| 43 | 10 | 71 |
| 45 | 10 | 114 |
| 48 | 10 | 74.6 |
| 58 | 10 | 98.9 |
| 62 | 10 | 97.3 |
| 65 | 10 | 94.1 |
| 66 | 10 | 74.9 |
| 67 | 10 | 88.9 |
| 69 | 10 | 97.4 |
| 72 | 10 | 91.4 |
| 74 | 10 | 96.9 |
| 79 | 10 | 99.4 |
| 81 | 10 | 72.6 |
| 84 | 10 | 97.7 |
| 101 | 10 | 78.3 |
| 104 | 10 | 82.0 |
| 110 | 10 | 80.7 |
| 111 | 10 | 78.8 |
| 121 | 10 | 91.2 |
| 141 | 10 | 94.6 |
| 142 | 10 | 101.1 |
| 143 | 10 | 98.9 |
| 148 | 10 | 95.9 |

Mobility refers to an expression of the measurement of the time for which the animal moved with its tail hung high as a percentage compared to the measurement of a control group. A MPTP single administration group exhibited about 50~70% in mobility against a control group (Sham) in which MPTP was not administered because the group showed 70 to 80% in brain damage, 40 to 50% in behavioral dysfunction, and a decrease in dopamine concentration in the brain by 70% or more, respectively compared to the control group (Sham), at 3 to 7 days after administration of MPTP.

As confirmed from the above results, it can be recognized that a group to which the azole derivative of Formula (I) was administered showed a mobility of 70.3~114 against a control group at an administration concentration of 10 mg/kg, compared to the MPTP single administration group showing behavioral dysfunctions against the control group.

B. Changes of Contents of Dopamine and its Metabolites in the Striatum

In order to review protective effects of the drug against MPTP toxicity, changes of contents of dopamine and its metabolites in the striatum were measured at 7 days after administration of MPTP.

TABLE 3

Levels of dopamine (DA) in the striata of MPTP-treated mice (% compared to a control group)

| No. of Compound in Example | Administration concentration | Compared to a control group % |
|---|---|---|
| 1 | 10 mpk | 111.5 |
| 6 | 10 mpk | 111.6 |
| 12 | 10 mpk | 78.8 |

TABLE 3-continued

Levels of dopamine (DA) in the striata of MPTP-
treated mice (% compared to a control group)

| No. of Compound in Example | Administration concentration | Compared to a control group % |
|---|---|---|
| 37 | 10 mpk | 79.2 |
| 38 | 10 mpk | 52.9 |
| 45 | 10 mpk | 41.1 |
| 62 | 10 mpk | 99.1 |
| 65 | 10 mpk | 74.9 |
| 67 | 10 mpk | 80.7 |
| 69 | 10 mpk | 100.47 |
| 71 | 10 mpk | 41.1 |
| 121 | 10 mpk | 97.86 |
| 141 | 10 mpk | 51.2 |
| 143 | 10 mpk | 46.1 |

The protective effects by the azole derivatives of Formula (I) against dopamine neuronal cell damage using an acute administration model of MPTP were observed. The observation showed that the MPTP single administration group exhibited a dopamine level in the striatum at 20 to 40% compared to the control group while a group to which the azole derivative of Formula (I) was administered showed a recovery of dopamine level at an administration concentration of 10 mg/kg to the level of the control group.

That is, for reduction in dopamine level in the striatum by MPTP and dopamine neuronal cell damage by MPTP, it was determined that the azole derivatives had neuron protective effects from the results of a dopamine level at an administration concentration of 10 mpk at up to 111.5% compared to the control group. The dopamine level reduced by MPTP was concentration-dependently recovered to show inhibitory effects against MAO-B. It can be confirmed that the azole derivatives substituted as above show inhibitory effects against dopamine neuronal cell damage, and are useful as a therapeutic agent for treating Parkinson's disease.

Example 207

Effects of the Combined Administration of a Composition Containing the Azole Derivative of the Present Invention and Levodopa (L-dopa) in a MPTP-Induced Mouse Model as an Animal Model of Parkinson's Disease An acute administration model of MPTP generally used was constructed by administration of MPTP (free base) at 15~25 mg/kg four times at the interval of 2 hours for a day (Breidert et al., 2002), and it was known that at 3 to 7 days after administration of MPTP, the administration model showed 70~80% in brain damage, 40~50% in behavioral dysfunction, and a decrease in dopamine concentration in the brain by 70% or more, respectively compared to a control group (Sham) in which MPTP was not administered, and was gradually recovered at 7 to 8 days after MPTP treatment (Khaldy et al., 2003; Bezard et al., 2000; Muramatsu et al., 2002).

In the case of Levodopa which is a gold standard of a drug for treating Parkinson's disease, various side effects have been reported after prolonged use of the drug, and the duration time of efficacy decreases. In order to prevent the limitations, co-administration therapies using MAO-B or COMT inhibitors, etc. have been widely used.

In the present invention, it is intended to know whether a composition containing the azole derivative of the present invention when co-administered with L-dopa is available as a drug for treating Parkinson's disease by using an animal mode in which Parkinson's disease was induced by administration of MPTP (1-methyl-4-phenyl-1,2,3,6-tetrahydropyridine).

(1) Materials and Methods

A. MPTP (1-methyl-4-phenyl-1,2,3,6-tetrahydropyridine) and Drug Treatment

MPTP (20 mg/kg, free base; Sigma, St. louis, Mo.) was administered to an 8 week old (20-25 g) male C57BL/6 test mouse intraperitoneally at the interval of 2 hours to construct a model.

In order to observe the effects of combined administration of a compound of the present invention and Levodopa, the compound of the present invention was dissolved in a solution containing 0.02 ml of dimethylsulfoxide (DMSO), 0.02 ml of Cremophor, 0.08 ml of polyethyleneglycol (PEG), and 0.08 ml of physiological saline. The resulting solution was orally administered at doses of 1 mg/kg one week after the MPTP treatment, and a Levodopa group containing Levodopa at 50 mg/kg and Benzerazide at 25 mg/kg was intraperitoneally administered 1 hour later.

Instead of MPTP, physiological saline was intraperitoneally administered in the same manner as above and the same solution was orally administered 1 hour before Phosphate Buffered Saline (PBS) treatment to construct a control group (Sham) in which MPTP was not administered.

A single administration of the Levodopa group in the following Table 4 indicates values resulting from a MPTP (toxin) treatment followed by an administration of the Levodopa group compared to the treatment results of a Levodopa single administration group of Levodopa and Benzerazide.

B. Measurement of Contents of Dopamine in the Striatum and Metabolites Thereof

The changes of contents of dopamine and dopamine metabolites in the striatum in accordance with administrations of MPTP and the drug were measured by high performance liquid chromatography (HPLC).

At 1 hour and 3 hours after administration of Levodopa, the animals were sacrificed by cervical vertebra dislocation and the brain tissues were immediately isolated from the animals. 0.5 me of iced solution for HPLC analysis (0.1 M perchloric acid and 0.1 mM EDTA) was added to a striatum obtained from the isolated brain tissues, and an ultrasonic grinder was used to prepare a tissue homogenate. The tissue homogenate was centrifuged at 12,000 rpm for 15 minutes, and its supernatant was filtered through nitrocellulose membrane filter (0.2 um, Millipore). For HPLC analysis, uBondapak™ C18 column (4.6×150 mm, particle size 10 μm: Shisheido, Japan) was used, the flow rate of the mobile phase (0.07 M monobasic sodium phosphate, 1 mM sodium octasulfonic acid, 0.1 uM EDTA, 5% acetonitrile, pH 3.2) was maintained at 0.5 me/min, and the electrode potential of the electrochemical detector (CouloChem III, ESA, Japan) was set at 350 mV.

(2) Results

A. The Changes of Contents of Dopamine and Dopamine Metabolites in the Striatum

In order to review the effects of combined administration of Levodopa group, the changes of contents of dopamine and metabolites thereof in the striatum were measured at 1 hour and 3 hours after administration of a Levodopa group. The results are summarized in the following Table 4.

TABLE 4

Concentration of dopamine (DA) in the striatum of a MPTP-treated mouse

| Example | Administration concentration | Concentration of dopamine compared to a control group % | |
|---|---|---|---|
| | | 1 hr | 3 hr |
| 1 | 1 mg/kg | 129.5 | 90.8 |
| 2 | 1 mg/kg | 106.12 | 43.6 |
| 3 | 1 mg/kg | 173.43 | 39.3 |
| 6 | 1 mg/kg | 220.87 | 59.8 |
| 62 | 1 mg/kg | 204.8 | 65.4 |
| 69 | 1 mg/kg | 205.2 | 200.4 |
| 74 | 1 mg/kg | 153.7 | 74.7 |
| 79 | 1 mg/kg | 87.6 | 115.2 |
| 84 | 1 mg/kg | 153.7 | 144.3 |
| 120 | 1 mg/kg | 148.5 | 53.9 |
| 121 | 1 mg/kg | 144.6 | 89.2 |
| 127 | 1 mg/kg | 140.7 | 60.4 |
| 130 | 1 mg/kg | 131.9 | 77.0 |
| 142 | 1 mg/kg | 174.5 | 65.5 |
| 152 | 1 mg/kg | 87.0 | 77.0 |
| 162 | 1 mg/kg | 148.3 | 100.1 |
| Single administration of Levodopa group | | 96.3 | 54.0 |

After observing whether a composition containing the azole derivative of the present invention when co-administered with L-dopa is available as a drug for treating Parkinson's disease by using an animal mode in which Parkinson's disease was induced by administration of MPTP (1-methyl-4-phenyl-1,2,3,6-tetrahydropyridine), it can be confirmed that a composition containing the azole derivative of the present invention at 1 mg/kg was co-administered at 1 hour and 3 hours, respectively, after administration of the Levodopa group to increase the amounts of dopamine in the striatum compared to a single administration of the Levodopa group.

When a compound of the present invention was administered in combination with Levodopa at 1 mg/kg, the amount of dopamine in the striatum to be reduced by MPTP administration exhibits an increase much more than that to be recovered by a single administration of Levodopa. Thus, it can be confirmed that a compound containing the azole derivative as substituted above has therapeutic effect of Parkinson's disease when it is administered in combination with Levodopa.

The invention claimed is:
1. A compound of Formula (I):

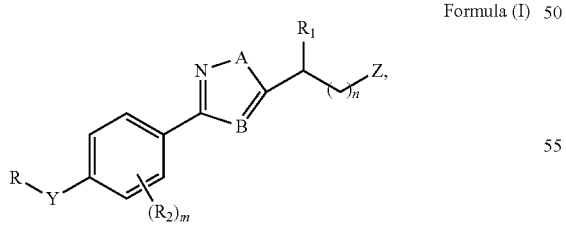

Formula (I)

or pharmaceutically acceptable salt thereof, wherein:
R is selected from the group consisting of $C_4$-$C_{15}$ arylalkyl optionally substituted with one or more groups selected from the group consisting of halo, trifluoromethyl, trifluoroalkoxy, —$NO_2$, —C(=O)$OCH_3$, $C_1$-$C_6$ alkyl, $C_1$-$C_6$ alkoxy, phenyl, phenyloxy, benzyloxy, —C(=O)H, —OH, and —CH(=N—OH); $C_4$-$C_{15}$ heteroarylalkyl optionally substituted with one or more groups selected from the group consisting of halo, —C(=O)$OCH_3$, $C_1$-$C_6$ alkyl, $C_1$-$C_6$ alkoxy, phenyl, phenyloxy and benzyloxy; and $C_1$-$C_{10}$ alkyl substituted with one or more groups selected from the group consisting of $C_1$-$C_3$ alkoxy, $C_1$-$C_3$ alkylthio, carbamate, tert-butyl-OC(=O)NH—, —$NH_3^+$, —$NH_2$, —OH, —C(=O)$OCH_2CH_3$, —NHC(=O)$NH_2$, trifluoromethylsulfanyl, trifluoromethyl and —CN;

Y is —O— or —$NR_1$—;

$R_1$ is —H or $C_1$-$C_3$ alkyl;

$R_2$ is halo;

A is —O— or —S—;

B is —CH= or —N=;

Z is selected from the group consisting of imidazolyl, tetrazolyl, —OC(=O)$NR_3R_4$, —$NR_5R_6$, —NHC(=NH)$NH_2$, and —NHC(=O)$NH_2$, wherein imidazolyl or tetrazolyl is optionally substituted with one or more groups selected from the group consisting of —OH, carbamate, $C_1$-$C_4$ alkyl, halo, —$NO_2$, —$NH_2$, —$CF_3$, —CN and phenyl;

each of $R_3$ and $R_4$ is independently selected from the group consisting of —H, $C_1$-$C_5$ alkyl optionally substituted with —$NH_2$, —$NR_7R_8$ or a heterocyclic ring optionally substituted with $C_1$-$C_3$ alkyl, or $R_3$ and $R_4$ are taken together to form a 5- or 7-membered heterocyclic ring optionally substituted with $C_1$-$C_3$ alkyl;

each of $R_5$ and $R_6$ is independently selected from the group consisting of —H, $C_2$-$C_3$ alkenyl, $C_2$-$C_3$ alkynyl and $C_1$-$C_7$ alkyl substituted with one or more groups selected from the group consisting of —OH, —C(=O)$NH_2$, $C_1$-$C_3$ alkoxy and carbamate, wherein at least one of $R_5$ and $R_6$ is other than —H;

each of $R_7$ and $R_8$ is independently selected from the group consisting of —H and $C_1$-$C_3$ alkyl;

m is 0, 1, 2, 3 or 4; and n is 0, 1, 2, 3, 4 or 5.

2. The compound of claim 1 which is selected from the group consisting of:
carbamic acid 3-(4-benzyloxy-phenyl)-isoxazole-5-ylmethyl ester;
carbamic acid 3-(4-benzyloxy-phenyl)-[1,2,4]oxadiazol-5-ylmethyl ester;
carbamic acid 3-(4-benzyloxy-phenyl)-isothiazol-5-ylmethyl ester;
carbamic acid 3-(4-benzyloxy-phenyl)-[1,2,4]thiadiazol-5-ylmethyl ester;
carbamic acid 3-(4-benzyloxy-2-chloro-phenyl)-isoxazol-5-ylmethyl ester;
carbamic acid 3-(4-benzyloxy-3-bromo-phenyl)-isoxazol-5-ylmethyl ester;
carbamic acid 3-(4-benzyloxy-3-chloro-phenyl)-isoxazol-5-ylmethyl ester;
carbamic acid 3-(4-benzyloxy-3-fluoro-phenyl)-isoxazol-5-ylmethyl ester;
carbamic acid 3-[4-(1-phenyl-ethoxy)-phenyl]- isoxazol-5-ylmethyl ester;
carbamic acid 3-[4-(2-fluoro-benzyloxy)-phenyl]-isoxazol-5-ylmethyl ester;
carbamic acid 3-[4-(3-fluoro-benzyloxy)-phenyl]-isoxazol-5-ylmethyl ester;
carbamic acid 3-[4-(4-fluoro-benzyloxy)-phenyl]-isoxazol-5-ylmethyl ester;
carbamic acid 3-[4-(2,6-difluoro-benzyloxy)-phenyl]-isoxazol-5-ylmethyl ester;
carbamic acid 3-[4-(2,3-difluoro-benzyloxy)-phenyl]-isoxazol-5-ylmethyl ester;

carbamic acid 3-[4-(3,5-difluoro-benzyloxy)-phenyl]-isoxazol-5-ylmethyl ester;
carbamic acid 3-[4-(3,4-difluoro-benzyloxy)-phenyl]-isoxazol-5-ylmethyl ester;
carbamic acid 3-[4-(2,4,6-trifluoro-benzyloxy)-phenyl]-isoxazol-5-ylmethyl ester;
carbamic acid 3-[4-(3-trifluoromethyl-benzyloxy)-phenyl]-isoxazol-5-ylmethyl ester;
carbamic acid 3-[4-(3-chloro-benzyloxy)-phenyl]-isoxazol-5-ylmethyl ester;
carbamic acid 3-[4-(2-chloro-benzyloxy)-phenyl]-isoxazol-5-ylmethyl ester;
carbamic acid 3-[4-(4-chloro-benzyloxy)-phenyl]-isoxazol-5-ylmethyl ester;
carbamic acid 3-[4-(2,6-dichlorobenzyloxy)-phenyl]-isoxazol-5-ylmethyl ester;
carbamic acid 3-[4-(2,5-di-chloro-benzyloxy)-phenyl]-isoxazol-5-ylmethyl ester;
carbamic acid 3-[4-(2-chloro-5-fluoro-benzyloxy)-phenyl]-isoxazol-5-ylmethyl ester;
carbamic acid 3-[4-(3-nitro-benzyloxy)-phenyl]-isoxazol-5-ylmethyl ester;
4-[4-(5-carbamoyloxymethyl-isoxazol-3-yl)-phenoxymethyl]-benzoic acid methyl ester;
3-[4-(4-methyl-benzyloxy)-phenyl]-isoxazol-5-ylmethyl ester;
carbamic acid 3-[4-(2-methyl-benzyloxy)-phenyl]-isoxazol-5-ylmethyl ester;
carbamic acid 3-[4-(3-methoxy-benzyloxy)-phenyl]-isoxazol-5-ylmethyl ester;
carbamic acid 3-[4-(3-trifluoromethyl-benzyloxy)-phenyl]-isoxazol-5-ylmethyl ester;
carbamic acid 3-[4-(4-isopropyl-benzyloxy)-phenyl]-isoxazol-5-ylmethyl ester;
carbamic acid 3-[4-(4-tert-butyl-benzyloxy)-phenyl]-isoxazol-5-ylmethyl ester;
carbamic acid 3-[4-(biphenyl-4-ylmethoxy)-phenyl]-isoxazol-5-ylmethyl ester;
carbamic acid 3-[4-(3-formyl-benzyloxy)-phenyl]-isoxazol-5-ylmethyl ester;
carbamic acid 3-[4-(4-formyl-benzyloxy)-phenyl]-isoxazol-5-ylmethyl ester;
carbamic acid 3-{4-[4-(hydroxyimino-methyl)-benzyloxy]-phenyl}-isoxazol-5-ylmethyl ester;
carbamic acid 3-{4-[3-(hydroxyimino-methyl)-benzyloxy]-phenyl}-isoxazol-5-ylmethyl ester;
[4-(5-carbamoyloxymethyl-isoxazol-3-yl)-phenoxy]-acetic acid ethyl ester;
[carbamic acid 3-(4-methylsulfanylmethoxy-phenyl)-isoxazol-5-ylmethyl ethyl ester;
carbamic acid 3-(4-methyoxymethoxy-phenyl)-isoxazol-5-ylmethyl ethyl ester;
carbamic acid {3-[4-(5-carbamoyloxymethyl-isoxazol-3-yl)-phenoxy]-propyl}-carbamic acid tert-butyl ester;
carbamic acid 3-[4-(3-amino-propoxy)-phenyl]-isoxazol-5-ylmethyl ester hydrochloride;
carbamic acid 3-[4-(5-carbamoyloxymethyl-isoxazol-3-yl)-phenoxy]-propyl ester;
4-[4-(5-carbamoyloxymethyl-isoxazol-3-yl)-phenoxy]-butyric acid ethyl ester;
carbamic acid 3-[4-(3-ureido-propoxy)-phenyl]-isoxazol-5-ylmethyl ester;
carbamic acid 3-[4-(2-hydroxy-ethoxy)-phenyl]-isoxazol-5-ylmethyl ester;
carbamic acid 2-[4-(5-carbamoyloxymethyl-isoxazol-3-yl)-phenoxy]-ethyl ester;
carbamic acid 3-[4-(4-hydroxy-butoxy)-phenyl]-isoxazol-5-ylmethyl ester;
carbamic acid 3-(4-trifluoromethylsulfanylmethoxy-phenyl)-isoxazol-5-ylmethyl ester;
carbamic acid 3-[4-(4,4,4-trifluoro-butoxy)-phenyl]-isoxazol-5-ylmethyl ester;
carbamic acid 3-[4-(3-cyano-propoxy)-phenyl]-isoxazol-5-ylmethyl ester;
carbamic acid 3-[4-(2-imidazol-1-yl-ethoxy)-phenyl]-isoxazol-5-ylmethyl ester;
carbamic acid 3-[4-(5-chloro-thiophen-2-ylmethyl)-phenyl]-isoxazol-5-ylmethyl ester;
carbamic acid 3-[4-(naphthalen-2-ylmethoxy)-phenyl]-isoxazol-5-ylmethyl ester;
carbamic acid 3-[4-(benzothiazol-2-ylmethoxy)-phenyl]-isoxazol-5-ylmethyl ester;
carbamic acid 3-[4-(pyridin-2-ylmethoxy)-phenyl]-isoxazol-5-ylmethyl ester;
carbamic acid 3-[4-(pyridin-3-ylmethoxy)-phenyl]-isoxazol-5-ylmethyl ester;
carbamic acid 3-[4-(pyridin-4-ylmethoxy)-phenyl]-isoxazol-5-ylmethyl ester;
carbamic acid 3-[4-(5-methoxy-4,6-dimethyl-pyridin-2-ylmethoxy)-phenyl]-isoxazol-5-ylmethyl ester;
carbamic acid 3-[4-(3,5-dichloro-pyridin-4-ylmethoxy)-phenyl]-isoxazol-5-ylmethyl ester;
carbamic acid 3-[4-(quinolin-2-ylmethoxy)-phenyl]-isoxazol-5-ylmethyl ester;
carbamic acid 3-[4-(benzotriazol-1-ylmethoxy)-phenyl]-isoxazol-5-ylmethyl ester;
carbamic acid 3-[4-(3,5-dimethyl-isoxazol-4-ylmethoxy)-phenyl]-isoxazol-5-ylmethyl ester;
5-[4-(5-carbamoyloxymethyl-isoxazol-3-yl)-phenoxymethyl]-furan-2-carboxylic acid methyl ester;
carbamic acid 3-(4-benzylamino-phenyl)-isoxazol-5-ylmethyl ester;
carbamic acid 3-[4-(benzyl-methyl-amino)-phenyl]-isoxazol-5-ylmethyl ester;
carbamic acid 3-[4-(4-fluoro-benzylamino)-phenyl]-isoxazol-5-ylmethyl ester;
carbamic acid 3-[4-(3-fluoro-benzylamino)-phenyl]-isoxazol-5-ylmethyl ester;
carbamic acid 3-[4-(2-fluoro-benzylamino)-phenyl]-isoxazol-5-ylmethyl ester;
carbamic acid 3-[4-(2,6-difluoro-benzylamino)-phenyl]-isoxazol-5-ylmethyl ester;
carbamic acid 3-[4-(2,3-difluoro-benzylamino)-phenyl]-isoxazol-5-ylmethyl ester;
carbamic acid 3-[4-(2,4-difluoro-benzylamino)-phenyl]-isoxazol-5-ylmethyl ester;
carbamic acid 3-[4-(3,5-difluoro-benzylamino)-phenyl]-isoxazol-5-ylmethyl ester;
carbamic acid 3-[4-(2,5-difluoro-benzylamino)-phenyl]-isoxazol-5-ylmethyl ester;
carbamic acid 3-[4-(3,4-difluoro-benzylamino)-phenyl]-isoxazol-5-ylmethyl ester;
carbamic acid 3-[4-(4-chloro-benzylamino)-phenyl]-isoxazol-5-ylmethyl ester;
carbamic acid 3-[4-(2-chloro-benzylamino)-phenyl]-isoxazol-5-ylmethyl ester;
carbamic acid 3-[4-(3-chloro-benzylamino)-phenyl]-isoxazol-5-ylmethyl ester;
carbamic acid 3-[4-(2,3-dichloro-benzylamino)-phenyl]-isoxazol-5-ylmethyl ester;
carbamic acid 3-[4-(2,4-dichloro-benzylamino)-phenyl]-isoxazol-5-ylmethyl ester;

carbamic acid 3-[4-(2,5-dichloro-benzylamino)-phenyl]-isoxazol-5-ylmethyl ester;
carbamic acid 3-[4-(2,6-dichloro-benzylamino)-phenyl]-isoxazol-5-ylmethyl ester;
carbamic acid 3-[4-(3,4-dichloro-benzylamino)-phenyl]-isoxazol-5-ylmethyl ester;
carbamic acid 3-[4-(3,5-dichloro-benzylamino)-phenyl]-isoxazol-5-ylmethyl ester;
carbamic acid 3-[4-(2,3,5-trichloro-benzylamino)-phenyl]-isoxazol-5-ylmethyl ester;
carbamic acid 3-[4-(2,3,6-trichloro-benzylamino)-phenyl]-isoxazol-5-ylmethyl ester;
carbamic acid 3-[4-(3-trifluoromethyl-benzylamino)-phenyl]-isoxazol-5-ylmethyl ester;
carbamic acid 3-[4-(4-trifluoromethyl-benzylamino)-phenyl]-isoxazol-5-ylmethyl ester;
carbamic acid 3-[4-(3,5-bis-trifluoromethyl-benzylamino)-phenyl]-isoxazol-5-ylmethyl ester;
carbamic acid 3-[4-(2-methyl-benzylamino)-phenyl]-isoxazol-5-ylmethyl ester;
carbamic acid 3-[4-(4-methyl-benzylamino)-phenyl]-isoxazol-5-ylmethyl ester;
carbamic acid 3-[4-(3-methyl-benzylamino)-phenyl]-isoxazol-5-ylmethyl ester;
carbamic acid 3-[4-(4-isopropyl-benzylamino)-phenyl]-isoxazol-5-ylmethyl ester;
carbamic acid 3-[4-(2,4-dimethyl-benzylamino)-phenyl]-isoxazol-5-ylmethyl ester;
carbamic acid 3-[4-(2-methoxy-benzylamino)-phenyl]-isoxazol-5-ylmethyl ester;
carbamic acid 3-[4-(3-methoxy-benzylamino)-phenyl]-isoxazol-5-ylmethyl ester;
carbamic acid 3-[4-(4-methoxy-benzylamino)-phenyl]-isoxazol-5-ylmethyl ester;
carbamic acid 3-[4-(4-phenoxy-benzylamino)-phenyl]-isoxazol-5-ylmethyl ester;
carbamic acid 3-[4-(4-benzyloxy-benzylamino)-phenyl]-isoxazol-5-ylmethyl ester;
carbamic acid 3-{4-[(5-phenyl-isoxazol-3-ylmethyl)-amino]-phenyl}-isoxazol-5-ylmethyl ester;
carbamic acid 3-{4-[(thiophen-2-ylmethyl)-amino]-phenyl}-isoxazol-5-ylmethyl ester;
carbamic acid 3-{4-[(furan-3-ylmethyl)-amino]-phenyl}-isoxazol-5-ylmethyl ester;
carbamic acid 3-{4-[(3,5-dimethyl-isoxazol-4-ylmethyl)-amino]-phenyl}-isoxazol-5-ylmethyl ester;
carbamic acid 3-[4-(3,5-di-tert-butyl-4-hydroxy-benzylamino)-phenyl]-isoxazol-5-ylmethyl ester;
carbamic acid 3-[4-(3,5-dimethyl-4-hydroxy-benzylamino)-phenyl]-isoxazol-5-ylmethyl ester;
carbamic acid 3-[4-(3,5-di-tert-butyl-benzylamino)-phenyl]-isoxazol-5-ylmethyl ester;
carbamic acid 3-[4-(3,4,5-trihydroxy-benzylamino)-phenyl]-isoxazol-5-ylmethyl ester;
carbamic acid 1-[3-(4-benzyloxy-phenyl)-isoxazol-5-yl]-ethyl ester;
carbamic acid 2-[3-(4-benzyloxy-phenyl)-isoxazol-5-yl]-ethyl ester;
[3-(4-benzyloxy-phenyl)-isoxazol-5-ylmethyl]-prop-2-ynyl-amine;
Imidazole-1-carboxylic acid 3-(4-benzyloxy-phenyl)-isoxazol-5-ylmethyl ester;
methyl-carbamic acid 3-(4-benzyloxy-phenyl)-isoxazol-5-ylmethyl ester;
dimethyl-carbamic acid 3-(4-benzyloxy-phenyl)-isoxazol-5-ylmethyl ester;
diethyl-carbamic acid 3-(4-benzyloxy-phenyl)-isoxazol-5-ylmethyl ester;
ethyl-methyl-carbamic acid 3-(4-benzyloxy-phenyl)-isoxazol-5-ylmethyl ester;
pyrrolidine-1-carboxylic acid 3-(4-benzyloxy-phenyl)-isoxazol-5-ylmethyl ester;
piperidine-1-carboxylic acid 3-(4-benzyloxy-phenyl)-isoxazol-5-ylmethyl ester;
morpholine-4-carboxylic acid 3-(4-benzyloxy-phenyl)-isoxazol-5-ylmethyl ester;
piperazine-1-carboxylic acid 3-(4-benzyloxy-phenyl)-isoxazol-5-ylmethyl ester;
N',N'dimethyl-hydrazinecarboxylic acid 3-(4-benzyloxy-phenyl)-isoxazol-5-ylmethyl ester;
(3-amino-propyl)-carbamic acid 3-(4-benzyloxy-phenyl)-isoxazol-5-ylmethyl ester;
(2-amino-ethyl)-carbamic acid 3-(4-benzyloxy-phenyl)-isoxazol-5-ylmethyl ester;
piperidine-1-yl-carbamic acid 3-(4-benzyloxy-phenyl)-isoxazol-5-ylmethyl ester;
(4-methyl-piperazin-1-yl)-carbamic acid 3-(4-benzyloxy-phenyl)-isoxazol-5-ylmethyl ester;
4-methyl-piperazin-1-carboxylic acid 3-(4-benzyloxy-phenyl)-isoxazol-5-ylmethyl ester;
piperidine-4-yl-carbamic acid 3-(4-benzyloxy-phenyl)-isoxazol-5-ylmethyl ester;
4-[3-(4-benzyloxy-phenyl)-isoxazol-5-ylmethoxycarbonyl]-[1,4]diazepan-1-ium chloride;
3-(4-benzyloxy-phenyl)-5-imidazol-1-ylmethyl-isoxazole;
3-(4-benzyloxy-phenyl)-5-(2-methyl-imidazol-1-ylmethyl)-isoxazole;
3-(4-benzyloxy-phenyl)-5-(4-methyl-imidazol-1-ylmethyl)-isoxazole;
3-[4-(3-fluoro-benzyloxy)-phenyl]-5-imidazol-1-ylmethyl-isoxazole;
3-[4-(2,6-difluoro-benzyloxy)-phenyl]-5-imidazol-1-ylmethyl-isoxazole;
2-[3-(4-benzyloxy-phenyl)-isoxazol-5-ylmethyl]-2H-tetrazole;
1-[3-(4-benzyloxy-phenyl)-isoxazol-5-ylmethyl]-2H-tetrazole;
[3-(4-benzyloxy-phenyl)-isoxazol-5-ylmethyl]-urea;
N-[3-(4-benzyloxy-phenyl)-isoxazol-5-ylmethyl]-guanidine;
3-[4-(2,4-difluoro-benzyloxy)-phenyl]-5-imidazol-1-ylmethyl-isoxazole;
5-imidazole-1-ylmethyl-3-[4-(2,4,6-trifluoro-benzyloxy)-phenyl]-isoxazole;
3-[4-(4-fluoro-benzyloxy)-phenyl]-5-imidazole-1-ylmethyl-isoxazole;
3-[4-(4-chloro-benzyloxy)-phenyl]-5-imidazol-1-ylmethyl-isoxazole;
3-[4-(4-fluoro-benzyloxy)-phenyl]-5-(4-methyl-imidazol-1-ylmethyl)-isoxazole;
3-[4-(3-fluoro-benzyloxy)-phenyl]-5-(4-methyl-imidazol-1-ylmethyl)-isoxazole;
3-[4-(2,4-difluoro-benzyloxy)-phenyl]-5-(4-methyl-imidazol-1-ylmethyl)-isoxazole;
2-{[3-(4-benzyloxy-phenyl)-isoxazol-5-ylmethyl]-amino}-acetamide;
2-{[3-(4-benzyloxy-phenyl)-isoxazol-5-ylmethyl]-amino}-propionamide;
2-{[3-(4-benzyloxy-phenyl)-isoxazol-5-ylmethyl]-amino}-2-methyl-propionamide;
carbamic acid 2-{[3-(4-benzyloxy-phenyl)-isoxazol-5-ylmethyl]-amino}-propyl ester hydrochloride;

2-{[3-(4-benzyloxy-phenyl)-isoxazol-5-ylmethyl]-amino}-3-hydroxy-propionamide;
2-{[3-(4-benzyloxy-phenyl)-isoxazol-5-ylmethyl]-amino}-ethanol;
2-{[3-(4-benzyloxy-phenyl)-isoxazol-5-ylmethyl]-amino}-propan-1-ol;
2-{[3-(4-benzyloxy-phenyl)-isoxazol-5-ylmethyl]-amino}-butan-1-ol;
2-{[3-(4-benzyloxy-phenyl)-isoxazol-5-ylmethyl]-amino}-2-methyl-propan-1-ol;
2-{[3-(4-benzyloxy-phenyl)-isoxazol-5-ylmethyl]-amino}-3-methyl-butan-1-ol;
2-{[3-(4-benzyloxy-phenyl)-isoxazol-5-ylmethyl]-amino}-propan-1,3-diol;
[3-(4-benzyloxy-phenyl)-isoxazol-5-ylmethyl]-(2-methoxy-ethyl)-amine;
carbamic acid 1-{3-[4-(pyridin-2-ylmethoxy-phenyl]-isoxazol-5-yl}-ethyl ester;
allyl-[3-(4-benzyloxy-phenyl)-isoxazol-5-ylmethyl]-amine;
carbamic acid 2-{[3-(4-benzyloxy-phenyl)-isoxazol-5-ylmethyl]-amino}-ethyl ester;
[3-(4-benzyloxy-phenyl)-isoxazol-5-ylmethyl]-methyl-prop-2-ynyl-amine;
3-(4-benzyloxy-phenyl)-5-(2-isopropyl-imidazol-1-ylmethyl)-isoxazole;
3-(4-benzyloxy-phenyl)-5-(4-bromo-imidazol-1-ylmethyl)-isoxazole;
3-(4-benzyloxy-phenyl)-5-(4,5-dichloro-imidazol-1-ylmethyl)-isoxazole;
3-(4-benzyloxy-phenyl)-5-(2-methyl-4,5-dichloro-imidazol-1-ylmethyl)-isoxazole;
3-(4-benzyloxy-phenyl)-5-(2-nitro-imidazol-1-ylmethyl)-isoxazole;
3-(4-benzyloxy-phenyl)-5-(4-phenyl-imidazol-1-ylmethyl)-isoxazole;
3-(4-benzyloxy-phenyl)-5-(4-nitro-imidazol-1-ylmethyl)-isoxazole;
3-(4-benzyloxy-phenyl)-5-(2-ethyl-4-methyl-imidazol-1-ylmethyl)-isoxazole;
3-(4-benzyloxy-phenyl)-5-(2-chloroimidazol-1-ylmethyl)-isoxazole;
3-(4-benzyloxy-phenyl)-5-(2-bromoimidazol-1-ylmethyl)-isoxazole;
3-(4-benzyloxy-phenyl)-5-(2-bromo-4,5-dichloroimidazol-1-ylmethyl)-isoxazole;
3-(4-benzyloxy-phenyl)-5-(2,4,5-tribromo-imidazol-1-ylmethyl)-isoxazole;
3-(4-benzyloxy-phenyl)-5-(2-ethyl-imidazol-1-ylmethyl)-isoxazole;
2-[4-(5-carbamoyloxymethyl-isoxazol-3-yl)-phenoxymethyl]-1-methyl-pyridinium iodide;
carbamic acid 3-[4-(benzyl-ethyl-amino)-phenyl]-isoxazol-5-ylmethyl ester;
carbamic acid 3-[4-(benzyl-propyl-amino)-phenyl]-isoxazol-5-ylmethyl ester;
carbamic acid 3-[4-(2,4-difluoro-benzyloxy)-phenyl]-isoxazol-5-ylmethyl ester;
carbamic acid 3-[4-(2,5-difluoro-benzyloxy)-phenyl]-isoxazol-5-ylmethyl ester;
carbamic acid 3-[4-(2,4-dichlorobenzyloxy)-phenyl]-isoxazol-5-ylmethyl ester;
carbamic acid 3-[4-(2-chloro-6-fluorobenzyloxy)-phenyl]-isoxazol-5-ylmethyl ester;
carbamic acid 3-[4-(3-methyl-benzyloxy)-phenyl]-isoxazol-5-ylmethyl ester;
carbamic acid 3-[4-(2-trifluoromethyl-benzyloxy)-phenyl]-isoxazol-5-ylmethyl ester;
carbamic acid 3-[4-(4-trifluoromethyl-benzyloxy)-phenyl]-isoxazol-5-ylmethyl ester; and
carbamic acid 3-[4-(benzo[1,3]dioxol-5-ylmethoxy)-phenyl]-isoxazol-5-ylmethyl ester.

3. The compound of claim 1, wherein R is benzyl.

4. The compound of claim 3, wherein Z is —OC(=O)NR$_3$R$_4$ and each of R$_3$ and R$_4$ is —H.

5. The compound of claim 4 which is selected from the group consisting of:
carbamic acid 3-(4-benzyloxy-phenyl)-isoxazole-5-ylmethyl ester;
carbamic acid 3-(4-benzyloxy-phenyl)-[1,2,4]oxadiazol-5-ylmethyl ester;
carbamic acid 3-(4-benzyloxy-phenyl)-isothiazol-5-ylmethyl ester;
carbamic acid 3-(4-benzyloxy-phenyl)-[1,2,4]thiadiazol-5-ylmethyl ester;
carbamic acid 3-(4-benzyloxy-2-chloro-phenyl)-isoxazol-5-ylmethyl ester;
carbamic acid 3-(4-benzyloxy-3-bromo-phenyl)-isoxazol-5-ylmethyl ester;
carbamic acid 3-(4-benzyloxy-3-chloro-phenyl)-isoxazol-5-ylmethyl ester;
carbamic acid 3-(4-benzyloxy-3-fluoro-phenyl)-isoxazol-5-ylmethyl ester;
carbamic acid 3-(4-benzylamino-phenyl)-isoxazole-5-ylmethyl ester;
carbamic acid 3-[4-(benzyl-methyl-amino)-phenyl]-isoxazol-5-ylmethyl ester;
carbamic acid 1-[3-(4-benzyloxy-phenyl)-isoxazol-5-yl]-ethyl ester;
carbamic acid 2-[3-(4-benzyloxy-phenyl)-isoxazol-5-yl]-ethyl ester;
carbamic acid 3-[4-(benzyl-ethyl-amino)-phenyl]-isoxazol-5-ylmethyl ester; and
carbamic acid 3-[4-(benzyl-propyl-amino)-phenyl]-isoxazol-5-ylmethyl ester.

6. The compound of claim 3, wherein Z is selected from the group consisting of imidazolyl, tetrazolyl, —OC(=O)NR$_3$R$_4$, —NR$_5$R$_6$, —NHC(=NH)NH$_2$, and —NHC(=O)NH$_2$, wherein imidazolyl or tetrazolyl is optionally substited with one or more groups selected from the group consisting of —OH, carbamate, C$_1$-C$_4$ alkyl, halo, —NO$_2$, —NH$_2$, —CF$_3$, —CN and phenyl.

7. The compound of claim 6 which is selected from the group consisting of:
[3-(4-benzyloxy-phenyl)-isoxazol-5-ylmethyl]-prop-2-ynyl-amine;
Imidazole-1-carboxylic acid 3-(4-benzyloxy-phenyl)-isoxazol-5-ylmethyl ester;
methyl-carbamic acid 3-(4-benzyloxy-phenyl)-isoxazol-5-ylmethyl ester;
dimethyl-carbamic acid 3-(4-benzyloxy-phenyl)-isoxazol-5-ylmethyl ester;
diethyl-carbamic acid 3-(4-benzyloxy-phenyl)-isoxazol-5-ylmethyl ester;
ethyl-methyl-carbamic acid 3-(4-benzyloxy-phenyl)-isoxazol-5-ylmethyl ester;
pyrrolidine-1-carboxylic acid 3-(4-benzyloxy-phenyl)-isoxazol-5-ylmethyl ester;
piperidine-1-carboxylic acid 3-(4-benzyloxy-phenyl)-isoxazol-5-ylmethyl ester;
morpholine-4-carboxylic acid 3-(4-benzyloxy-phenyl)-isoxazol-5-ylmethyl ester;

piperazine-1-carboxylic acid 3-(4-benzyloxy-phenyl)-isoxazol-5-ylmethyl ester;
N',N'-dimethyl-hydrazinecarboxylic acid 3-(4-benzyloxy-phenyl)-isoxazol-5-ylmethyl ester;
(3-amino-propyl)-carbamic acid 3-(4-benzyloxy-phenyl)-isoxazol-5-ylmethyl ester;
(2-amino-ethyl)-carbamic acid 3-(4-benzyloxy-phenyl)-isoxazol-5-ylmethyl ester;
piperidine-1-yl-carbamic acid 3-(4-benzyloxy-phenyl)-isoxazol-5-ylmethyl ester;
(4-methyl-piperazin-1-yl)-carbamic acid 3-(4-benzyloxy-phenyl)-isoxazol-5-ylmethyl ester;
4-methyl-piperazin-1-carboxylic acid 3-(4-benzyloxy-phenyl)-isoxazol-5-ylmethyl ester;
piperidine-4-yl-carbamic acid 3-(4-benzyloxy-phenyl)-isoxazol-5-ylmethyl ester;
4-[3-(4-benzyloxy-phenyl)-isoxazol-5-ylmethoxycarbonyl]-[1,4]diazepan-1-ium chloride;
3-(4-benzyloxy-phenyl)-5-imidazol-1-ylmethyl-isoxazole;
3-(4-benzyloxy-phenyl)-5-(2-methyl-imidazol-1-ylmethyl)-isoxazole;
3-(4-benzyloxy-phenyl)-5-(4-methyl-imidazol-1-ylmethyl)-isoxazole;
2-[3-(4-benzyloxy-phenyl)-isoxazol-5-ylmethyl]-2H-tetrazole;
1-[3-(4-benzyloxy-phenyl)-isoxazol-5-ylmethyl]-2H-tetrazole;
[3-(4-benzyloxy-phenyl)-isoxazol-5-ylmethyl]-urea;
N-[3-(4-benzyloxy-phenyl)-isoxazol-5-ylmethyl]-guanidine;
2-{[3-(4-benzyloxy-phenyl)-isoxazol-5-ylmethyl]-amino}-acetamide;
2-{[3-(4-benzyloxy-phenyl)-isoxazol-5-ylmethyl]-amino}-propionamide;
2-{[3-(4-benzyloxy-phenyl)-isoxazol-5-ylmethyl]-amino}-2-methyl-propionamide;
carbamic acid 2-{[3-(4-benzyloxy-phenyl)-isoxazol-5-ylmethyl]-amino}-propyl ester hydrochloride;
2-{[3-(4-benzyloxy-phenyl)-isoxazol-5-ylmethyl]-amino}-3-hydroxy-propionamide;
2-{[3-(4-benzyloxy-phenyl)-isoxazol-5-ylmethyl]-amino}-ethanol;
2-{[3-(4-benzyloxy-phenyl)-isoxazol-5-ylmethyl]-amino}-propan-1-ol;
2-{[3-(4-benzyloxy-phenyl)-isoxazol-5-ylmethyl]-amino}-butan-1-ol;
2-{[3-(4-benzyloxy-phenyl)-isoxazol-5-ylmethyl]-amino}-2-methyl-propan-1-ol;
2-{[3-(4-benzyloxy-phenyl)-isoxazol-5-ylmethyl]-amino}-3-methyl-butan-1-ol;
2-{[3-(4-benzyloxy-phenyl)-isoxazol-5-ylmethyl]-amino}-propan-1,3-diol;
[3-(4-benzyloxy-phenyl)-isoxazol-5-ylmethyl]-(2-methoxy-ethyl)-amine;
allyl-[3-(4-benzyloxy-phenyl)-isoxazol-5-ylmethyl]amine;
carbamic acid 2-{[3-(4-benzyloxy-phenyl)-isoxazol-5-ylmethyl]-amino}-ethyl ester;
[3-(4-benzyloxy-phenyl)-isoxazol-5-ylmethyl]-methyl-prop-2-ynyl-amine;
3-(4-benzyloxy-phenyl)-5-(2-isopropyl-imidazol-1-ylmethyl)-isoxazole;
3-(4-benzyloxy-phenyl)-5-(4-bromo-imidazol-1-ylmethyl)-isoxazole;
3-(4-benzyloxy-phenyl)-5-(4,5-dichloro-imidazol-1-ylmethyl)-isoxazole;
3-(4-benzyloxy-phenyl)-5-(2-methyl-4,5-dichloro-imidazol-1-ylmethyl)-isoxazole;
3-(4-benzyloxy-phenyl)-5-(2-nitro-imidazol-1-ylmethyl)-isoxazole;
3-(4-benzyloxy-phenyl)-5-(4-phenyl-imidazol-1-ylmethyl)-isoxazole;
3-(4-benzyloxy-phenyl)-5-(4-nitro-imidazol-1-ylmethyl)-isoxazole;
3-(4-benzyloxy-phenyl)-5-(2-ethyl-4-methyl-imidazol-1-ylmethyl)-isoxazole;
3-(4-benzyloxy-phenyl)-5-(2-chloroimidazol-1-ylmethyl)-isoxazole;
3-(4-benzyloxy-phenyl)-5-(2-bromoimidazol-1-ylmethyl)-isoxazole;
3-(4-benzyloxy-phenyl)-5-(2-bromo-4,5-dichloroimidazol-1-ylmethyl)-isoxazole;
3-(4-benzyloxy-phenyl)-5-(2,4,5-tribromo-imidazol-1-ylmethyl)-isoxazole; and
3-(4-benzyloxy-phenyl)-5-(2-ethyl-imidazol-1-ylmethyl)-isoxazole.

8. The compound of claim 1, wherein R is benzyl substituted with one or more groups selected from the group consisting of halo, trifluoromethyl, trifluoroalkoxy, —$NO_2$, —C(=O)$OCH_3$, $C_1$-$C_6$ alkyl, $C_1$-$C_6$ alkoxy, phenyl, phenyloxy, benzyloxy, —C(=O)H, —OH, and —CH(=N—OH).

9. The compound of claim 8, wherein Z is —OC(=O)$NR_3R_4$ and each of $R_3$ and $R_4$ is —H.

10. The compound of claim 9 which is selected from the group consisting of:
carbamic acid 3-[4-(2-fluoro-benzyloxy)-phenyl]-isoxazol-5-ylmethyl ester;
carbamic acid 3-[4-(3-fluoro-benzyloxy)-phenyl]-isoxazol-5-ylmethyl ester;
carbamic acid 3-[4-(4-fluoro-benzyloxy)-phenyl]-isoxazol-5-ylmethyl ester;
carbamic acid 3-[4-(2,6-difluoro-benzyloxy)-phenyl]-isoxazol-5-ylmethyl ester;
carbamic acid 3-[4-(2,3-difluoro-benzyloxy)-phenyl]-isoxazol-5-ylmethyl ester;
carbamic acid 3-[4-(3,5-difluoro-benzyloxy)-phenyl]-isoxazol-5-ylmethyl ester;
carbamic acid 3-[4-(3,4-difluoro-benzyloxy)-phenyl]-isoxazol-5-ylmethyl ester;
carbamic acid 3-[4-(2,4,6-trifluoro-benzyloxy)-phenyl]-isoxazol-5-ylmethyl ester;
carbamic acid 3-[4-(3-trifluoromethyl-benzyloxy)-phenyl]-isoxazol-5-ylmethyl ester;
carbamic acid 3-[4-(3-chloro-benzyloxy)-phenyl]-isoxazol-5-ylmethyl ester;
carbamic acid 3-[4-(2-chloro-benzyloxy)-phenyl]-isoxazol-5-ylmethyl ester;
carbamic acid 3-[4-(4-chloro-benzyloxy)-phenyl]-isoxazol-5-ylmethyl ester;
carbamic acid 3-[4-(2,6-dichlorobenzyloxy)-phenyl]-isoxazol-5-ylmethyl ester;
carbamic acid 3-[4-(2,5-di-chloro-benzyloxy)-phenyl]-isoxazol-5-ylmethyl ester;
carbamic acid 3-[4-(2-chloro-5-fluoro-benzyloxy)-phenyl]-isoxazol-5-ylmethyl ester;
carbamic acid 3-[4-(3-nitro-benzyloxy)-phenyl]-isoxazol-5-ylmethyl ester;
4-[4-(5-carbamoyloxymethyl-isoxazol-3-yl)-phenoxymethyl]-benzoic acid methyl ester;
3-[4-(4-methyl-benzyloxy)-phenyl]-isoxazol-5-ylmethyl ester;
carbamic acid 3-[4-(2-methyl-benzyloxy)-phenyl]-isoxazol-5-ylmethyl ester;

carbamic acid 3-[4-(3-methoxy-benzyloxy)-phenyl]-isoxazol-5-ylmethyl ester;
carbamic acid 3-[4-(3-trifluoromethyl-benzyloxy)-phenyl]-isoxazol-5-ylmethyl ester;
carbamic acid 3-[4-(4-isopropyl-benzyloxy)-phenyl]-isoxazol-5-ylmethyl ester;
carbamic acid 3-[4-(4-tert-butyl-benzyloxy)-phenyl]-isoxazol-5-ylmethyl ester;
carbamic acid 3-[4-(biphenyl-4-ylmethoxy)-phenyl]-isoxazol-5-ylmethyl ester;
carbamic acid 3-[4-(3-formyl-benzyloxy)-phenyl]-isoxazol-5-ylmethyl ester;
carbamic acid 3-[4-(4-formyl-benzyloxy)-phenyl]-isoxazol-5-ylmethyl ester;
carbamic acid 3-{4-[4-(hydroxyimino-methyl)-benzyloxy]-phenyl}-isoxazol-5-ylmethyl ester;
carbamic acid 3-[4-(naphthalen-2-ylmethoxy)-phenyl]-isoxazol-5-ylmethyl ester;
carbamic acid 3-{4-[3-(hydroxyimino-methyl)-benzyloxy]-phenyl}-isoxazol-5-ylmethyl ester;
carbamic acid 3-[4-(4-fluoro-benzylamino)-phenyl]-isoxazol-5-ylmethyl ester;
carbamic acid 3-[4-(3-fluoro-benzylamino)-phenyl]-isoxazol-5-ylmethyl ester;
carbamic acid 3-[4-(2-fluoro-benzylamino)-phenyl]-isoxazol-5-ylmethyl ester;
carbamic acid 3-[4-(2,6-difluoro-benzylamino)-phenyl]-isoxazol-5-ylmethyl ester;
carbamic acid 3-[4-(2,3-difluoro-benzylamino)-phenyl]-isoxazol-5-ylmethyl ester;
carbamic acid 3-[4-(2,4-difluoro-benzylamino)-phenyl]-isoxazol-5-ylmethyl ester;
carbamic acid 3-[4-(3,5-difluoro-benzylamino)-phenyl]-isoxazol-5-ylmethyl ester;
carbamic acid 3-[4-(2,5-difluoro-benzylamino)-phenyl]-isoxazol-5-ylmethyl ester;
carbamic acid 3-[4-(3,4-difluoro-benzylamino)-phenyl]-isoxazol-5-ylmethyl ester;
carbamic acid 3-[4-(4-chloro-benzylamino)-phenyl]-isoxazol-5-ylmethyl ester;
carbamic acid 3-[4-(2-chloro-benzylamino)-phenyl]-isoxazol-5-ylmethyl ester;
carbamic acid 3-[4-(3-chloro-benzylamino)-phenyl]-isoxazol-5-ylmethyl ester;
carbamic acid 3-[4-(2,3-dichloro-benzylamino)-phenyl]-isoxazol-5-ylmethyl ester;
carbamic acid 3-[4-(2,4-dichloro-benzylamino)-phenyl]-isoxazol-5-ylmethyl ester;
carbamic acid 3-[4-(2,5-dichloro-benzylamino)-phenyl]-isoxazol-5-ylmethyl ester;
carbamic acid 3-[4-(2,6-dichloro-benzylamino)-phenyl]-isoxazol-5-ylmethyl ester;
carbamic acid 3-[4-(3,4-dichloro-benzylamino)-phenyl]-isoxazol-5-ylmethyl ester;
carbamic acid 3-[4-(3,5-dichloro-benzylamino)-phenyl]-isoxazol-5-ylmethyl ester;
carbamic acid 3-[4-(2,3,5-trichloro-benzylamino)-phenyl]-isoxazol-5-ylmethyl ester;
carbamic acid 3-[4-(2,3,6-trichloro-benzylamino)-phenyl]-isoxazol-5-ylmethyl ester;
carbamic acid 3-[4-(3-trifluoromethyl-benzylamino)-phenyl]-isoxazol-5-ylmethyl ester;
carbamic acid 3-[4-(4-trifluoromethyl-benzylamino)-phenyl]-isoxazol-5-ylmethyl ester;
carbamic acid 3-[4-(3,5-bis-trifluoromethyl-benzylamino)-phenyl]-isoxazol-5-ylmethyl ester;
carbamic acid 3-[4-(2-methyl-benzylamino)-phenyl]-isoxazol-5-ylmethyl ester;
carbamic acid 3-[4-(4-methyl-benzylamino)-phenyl]-isoxazol-5-ylmethyl ester;
carbamic acid 3-[4-(3-methyl-benzylamino)-phenyl]-isoxazol-5-ylmethyl ester;
carbamic acid 3-[4-(4-isopropyl-benzylamino)-phenyl]-isoxazol-5-ylmethyl ester;
carbamic acid 3-[4-(2,4-dimethyl-benzylamino)-phenyl]-isoxazol-5-ylmethyl ester;
carbamic acid 3-[4-(2-methoxy-benzylamino)-phenyl]-isoxazol-5-ylmethyl ester;
carbamic acid 3-[4-(3-methoxy-benzylamino)-phenyl]-isoxazol-5-ylmethyl ester;
carbamic acid 3-[4-(4-methoxy-benzylamino)-phenyl]-isoxazol-5-ylmethyl ester;
carbamic acid 3-[4-(4-phenoxy-benzylamino)-phenyl]-isoxazol-5-ylmethyl ester;
carbamic acid 3-[4-(4-benzyloxy-benzylamino)-phenyl]-isoxazol-5-ylmethyl ester;
carbamic acid 3-[4-(3,5-di-tert-butyl-4-hydroxy-benzylamino)-phenyl]-isoxazol-5-ylmethyl ester;
carbamic acid 3-[4-(3,5-dimethyl-4-hydroxy-benzylamino)-phenyl]-isoxazol-5-ylmethyl ester;
carbamic acid 3-[4-(3,5-di-tert-butyl-benzylamino)-phenyl]-isoxazol-5-ylmethyl ester;
carbamic acid 3-[4-(3,4,5-trihydroxy-benzylamino)-phenyl]-isoxazol-5-ylmethyl ester;
carbamic acid 3-[4-(2,4-difluoro-benzyloxy)-phenyl]-isoxazol-5-ylmethyl ester;
carbamic acid 3-[4-(2,5-difluoro-benzyloxy)-phenyl]-isoxazol-5-ylmethyl ester;
carbamic acid 3-[4-(2,4-dichlorobenzyloxy)-phenyl]-isoxazol-5-ylmethyl ester;
carbamic acid 3-[4-(2-chloro-6-fluorobenzyloxy)-phenyl]-isoxazol-5-ylmethyl ester;
carbamic acid 3-[4-(3-methyl-benzyloxy)-phenyl]-isoxazol-5-ylmethyl ester;
carbamic acid 3-[4-(2-trifluoromethyl-benzyloxy)-phenyl]-isoxazol-5-ylmethyl ester;
carbamic acid 3-[4-(4-trifluoromethyl-benzyloxy)-phenyl]-isoxazol-5-ylmethyl ester; and
carbamic acid 3-[4-(benzo[1,3]dioxol-5-ylmethoxy)-phenyl]-isoxazol-5-ylmethyl ester.

11. The compound of claim 8, wherein Z is selected from the group consisting of imidazolyl, tetrazolyl, —OC(═O)NR$_3$R$_4$, —NR$_5$R$_6$, —NHC(═NH)NH$_2$, and —NHC(═O)NH$_2$, wherein imidazolyl or tetrazolyl is optionally substituted with one or more groups selected from the group consisting of —OH, carbamate, C$_1$-C$_4$ alkyl, halo, —NO$_2$, —NH$_2$, —CF$_3$, —CN and phenyl.

12. The compound of claim 11 which is selected from the group consisting of:
3-[4-(3-fluoro-benzyloxy)-phenyl]-5-imidazol-1-ylmethyl-isoxazole;
3-[4-(2,6-difluoro-benzyloxy)-phenyl]-5-imidazol-1-ylmethyl-isoxazole;
3-[4-(2,4-difluoro-benzyloxy)-phenyl]-5-imidazol-1-ylmethyl-isoxazole;
5-imidazol-1-ylmethyl-3-[4-(2,4,6-trifluoro-benzyloxy)-phenyl]-isoxazole;
3-[4-(4-fluoro-benzyloxy)-phenyl]-5-imidazol-1-ylmethyl-isoxazole;
3-[4-(4-chloro-benzyloxy)-phenyl]-5-imidazol-1-ylmethyl-isoxazole;
3-[4-(4-fluoro-benzyloxy)-phenyl]-5-(4-methyl-imidazol-1-ylmethyl)-isoxazole;

3-[4-(3-fluoro-benzyloxy)-phenyl]-5-(4-methyl-imidazol-1-ylmethyl)-isoxazole; and
3-[4-(2,4-difluoro-benzyloxy)-phenyl]-5-(4-methyl-imidazol-1-ylmethyl)-isoxazole.

13. The compound of claim 1, wherein R is $C_1$-$C_{10}$ alkyl substituted with one or more groups selected from the group consisting of $C_1$-$C_3$ alkoxy, $C_1$-$C_3$ alkylthio, carbamate, tert-butyl-OC(=O)NH—, —$NH_3^+$, —$NH_2$, —OH, —C(=O)OCH$_2$CH$_3$, —NHC(=O)NH$_2$, trifluoromethylsulfanyl, trifluoromethyl and —CN.

14. The compound of claim 13, which is selected from the group consisting of:
    [4-(5-carbamoyloxymethyl-isoxazol-3-yl)-phenoxy]-acetic acid ethyl ester;
    carbamic acid 3-(4-methylsulfanylmethoxy-phenyl)-isoxazol-5-ylmethyl ethyl ester;
    carbamic acid 3-(4-methoxymethoxy-phenyl)-isoxazol-5-ylmethyl ethyl ester;
    carbamic acid {3-[4-(5-carbamoyloxymethyl-isoxazol-3-yl)-phenoxy]-propyl}-carbamic acid tert-butyl ester;
    carbamic acid 3-[4-(3-amino-propoxy)-phenyl]-isoxazol-5-ylmethyl ester hydrochloride;
    carbamic acid 3-[4-(5-carbamoyloxymethyl-isoxazol-3-yl)-phenoxy]-propyl ester;
    4-[4-(5-carbamoyloxymethyl-isoxazol-3-yl)-phenoxy]-butyric acid ethyl ester;
    carbamic acid 3-[4-(3-ureido-propoxy)-phenyl]-isoxazol-5-ylmethyl ester;
    carbamic acid 3-[4-(2-hydroxy-ethoxy)-phenyl]-isoxazol-5-ylmethyl ester;
    carbamic acid 2-[4-(5-carbamoyloxymethyl-isoxazol-3-yl)-phenoxy]-ethyl ester;
    carbamic acid 3-[4-(4-hydroxy-butoxy)-phenyl]-isoxazol-5-ylmethyl ester;
    carbamic acid 3-(4-trifluoromethylsulfanylmethoxy-phenyl)-isoxazol-5-ylmethyl ester;
    carbamic acid 3-[4-(4,4,4-trifluoro-butoxy)-phenyl]-isoxazol-5-ylmethyl ester; and
    carbamic acid 3-[4-(3-cyano-propoxy)-phenyl]-isoxazol-5-ylmethyl ester.

15. The compound of claim 1, wherein R is $C_4$-$C_{15}$ heteroarylalkyl optionally substituted with one or more groups selected from the group consisting of halo, —C(=O)OCH$_3$, $C_1$-$C_6$ alkyl, $C_1$-$C_6$ alkoxy, phenyl, phyenyloxy and benzyloxy.

16. The compound of claim 15 which is selected from the group consisting of:
    carbamic acid 3-[4-(2-imidazol-1-yl-ethoxy)-phenyl]-isoxazol-5-ylmethyl ester;
    carbamic acid 3-[4-(5-chloro-thiophen-2-ylmethoxy)-phenyl]-isoxazol-5-ylmethyl ester;
    carbamic acid 3-[4-(benzothiazol-2-ylmethoxy)-phenyl]-isoxazol-5-ylmethyl ester;
    carbamic acid 3-[4-(pyridin-2-ylmethoxy)-phenyl]-isoxazol-5-ylmethyl ester;
    carbamic acid 3-[4-(pryidin-3-ylmethoxy)-phenyl]-isoxazol-5-ylmethyl ester;
    carbamic acid 3-[4-(pryidin-4-ylmethoxy)-phenyl]-isoxazol-5-ylmethyl ester;
    carbamic acid 3-[4-(5-methoxy-4,6-dimethyl-pyridin-2-ylmethoxy)-phenyl]-isoxazol-5-ylmethyl ester;
    carbamic acid 3-[4-(3,5-dichloro-pyridin-4-ylmethoxy)-phenyl]-isoxazol-5-ylmethyl ester;
    carbamic acid 3-[4-(quinolin-2-ylmethoxy)-phenyl]-isoxazol-5-ylmethyl ester;
    carbamic acid 3-[4-(benzotriazol-1-ylmethoxy)-phenyl]-isoxazol-5-ylmethyl ester;
    carbamic acid 3-[4-(3,5-dimethyl-isoxazol-4-ylmethoxy)-phenyl]-isoxazol-5-ylmethyl ester;
    5-[4-(5-carbamoyloxymethyl-isoxazol-3-yl)-phenoxymethyl]-furan-2-carboxylic acid methyl ester;
    carbamic acid 3-{4-[(5-phenyl-isoxazol-3-ylmethyl)-amino]-phenyl}-isoxazol-5-ylmethyl ester;
    carbamic acid 3-{4-[(thiophen-2-ylmethyl)-amino]-phenyl}-isoxazol-5-ylmethyl ester;
    carbamic acid 3-{4-[(furan-3-ylmethyl)-amino]-phenyl}-isoxazol-5-ylmethyl ester;
    carbamic acid 3-{4-[(3,5-dimethyl-isoxazol-4-ylmethyl)-amino]-phenyl}-isoxazol-5-ylmethyl ester;
    carbamic acid 1-{3-[4-(pyridin-2-ylmethoxy)-phenyl]-isoxazol-5-yl}-ethyl ester; and
    2-[4-(5-carbamoyloxymethyl-isoxazol-3-yl)-phenoxymethyl]-1-methyl-pyridinium iodide.

17. The compound of claim 1, wherein Z is —OC(=O)NR$_3$R and each of R$_3$ and R$_4$ is —H.

18. The compound of claim 1 which is carbamic acid 3-(4-benzyloxy-phenyl)-isoxazole-5-ylmethyl ester.

19. A new compound which is selected from the group consisting of:
    carbamic acid 3-(4-benzyloxy-3,5-dimethyl-phenyl)-isoxazol-5-ylmethyl ester;
    carbamic acid 3-(4-prop-2-ynyloxy-phenyl)-isoxazol-5-ylmethyl ester;
    carbamic acid 3-(4-cyclohexylmethoxy-phenyl)-isoxazol-5-ylmethyl ester;
    carbamic acid 3-[4-(1-oxy-pyridin-2-ylmethoxy)-phenyl]-isoxazol-5-ylmethyl ester;
    carbamic acid 1-[3-(4-benzyloxy-phenyl)-isoxazol-5-yl]-1-methyl-ethyl ester;
    carbamic acid 3-(4-cycloplentylmethoxy-phenyl)-isoxazol-5-ylmethyl ester; and
    carbamic acid 3-{4-[3-(t-butylnitronyl)-benzyloxy]-phenyl}-isoxazol-5-ylmethyl ester.

20. A pharmaceutical composition comprising an effective amount of the compound of Formula (I) of claim 1 or a pharmaceutically acceptable salt thereof, and a pharmaceutically acceptable carrier.

21. The composition of claim 20, further comprising levodopa.

22. The composition of claim 20, further comprising levodopa and a DOPA decarboxylase inhibitor.

23. The composition of claim 22, wherein the DOPA decarboxylase inhibitor is benserazide or carbidopa.

24. The composition of claim 20, wherein the effective amount is about 0.01 mg to about 100 mg.

25. A method for treating Parkinson's disease, comprising:
    administering to a mammal in need thereof an effective amount of the compound of Formula (I) of claim 1 or a pharmaceutically acceptable salt thereof.

26. The method of claim 24, wherein the compound of Formula (I) of claim 1 or a pharmaceutically acceptable salt thereof is administered in combination with levodopa and a DOPA decarboxylase inhibitor.

27. The method of claim 24, wherein the effective amount is administered as a total daily dosage of 0.1 mg to 10 mg per kg of body weight.

* * * * *